(12) United States Patent
Kinsella et al.

(10) Patent No.: US 10,966,994 B2
(45) Date of Patent: *Apr. 6, 2021

(54) THROMBOXANE RECEPTOR ANTAGONISTS

(71) Applicant: ATXA THERAPEUTICS LIMITED, Dublin (IE)

(72) Inventors: B. Therese Kinsella, Dublin (IE); Helen Reid, Dublin (IE)

(73) Assignee: ATXA THERAPEUTICS LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/517,947

(22) Filed: Jul. 22, 2019

(65) Prior Publication Data
US 2019/0336513 A1    Nov. 7, 2019

Related U.S. Application Data

(63) Continuation of application No. 15/901,503, filed on Feb. 21, 2018, now Pat. No. 10,357,504, which is a continuation of application No. 15/180,805, filed on Jun. 13, 2016, now Pat. No. 9,932,304.

(60) Provisional application No. 62/180,317, filed on Jun. 16, 2015.

(51) Int. Cl.
*A61K 31/64*        (2006.01)
*C07C 311/58*      (2006.01)

(52) U.S. Cl.
CPC ............ *A61K 31/64* (2013.01); *C07C 311/58* (2013.01)

(58) Field of Classification Search
CPC .............................. A61K 31/64; C07C 311/58
See application file for complete search history.

(56) References Cited

U.S. PATENT DOCUMENTS

| | | |
|---|---|---|
| 3,556,764 A | 1/1971 | Hamm |
| 3,714,209 A | 1/1973 | Tung |
| 4,166,452 A | 9/1979 | Generales, Jr. |
| 4,256,108 A | 3/1981 | Theeuwes |
| 4,265,874 A | 5/1981 | Bonsen et al. |
| 5,434,124 A | 7/1995 | Mayer et al. |
| 5,697,967 A | 12/1997 | Dinh et al. |
| 6,136,157 A | 10/2000 | Lindeberg et al. |
| 6,214,841 B1 | 4/2001 | Jackson et al. |
| 6,231,600 B1 | 5/2001 | Zhong |
| 6,352,552 B1 | 3/2002 | Levinson et al. |
| 6,583,307 B2 | 6/2003 | Nolan et al. |
| 6,796,998 B2 | 9/2004 | Schaldach et al. |
| 7,135,038 B1 | 11/2006 | Limon |
| 7,618,949 B2 | 11/2009 | Boyer et al. |
| 7,713,538 B2 | 5/2010 | Lewis et al. |
| 7,833,544 B2 | 11/2010 | Lewis et al. |

(Continued)

FOREIGN PATENT DOCUMENTS

| | | |
|---|---|---|
| WO | 00/42004 A1 | 7/2000 |
| WO | 2009/089098 A1 | 7/2009 |

(Continued)

OTHER PUBLICATIONS

Bambi-Nyanguile, 2013, Synthesis and pharmacological evaluation of 2-aryloxy/aryalmino-5-cyanobenzenesulfonyl ureas as novel thromboxane A2 receptor antagonists, Eur J Med Chem 65:32-40.

(Continued)

*Primary Examiner* — Valerie Rodriguez-Garcia
(74) *Attorney, Agent, or Firm* — Brown Rudnick LLP

(57) ABSTRACT

The invention relates to novel chemical entities that act as thromboxane (TX) $A_2$ receptor, or T prostanoid receptor (TP), antagonists and to their use in the treatment of human diseases in which thromboxane (TX) $A_2$ and of all other agents that act as incidental ligands of TP play a role. Compounds are represented by the formula (I):

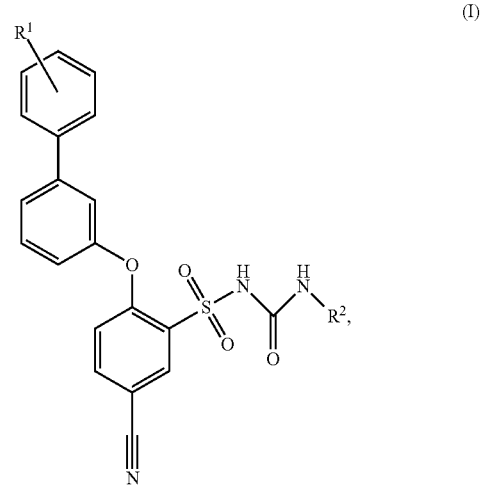

(I)

wherein:

$R^1$ is selected from the group consisting of a difluoromethoxy group, a trifluoromethoxy group, a difluoromethyl group, a primary amide, a secondary amide group, a tertiary amide group, and a nitrile group; and $R^2$ is selected from the group consisting of an alkyl group of 6 or fewer carbons and a halogenated alkyl group of 6 or fewer carbons, wherein $R^2$ is not tert butyl, or a pharmaceutically acceptable salt thereof.

22 Claims, 22 Drawing Sheets

(56) References Cited

U.S. PATENT DOCUMENTS

| | | | |
|---|---|---|---|
| 7,947,302 | B2 | 5/2011 | Falotico et al. |
| 8,486,994 | B2 | 7/2013 | Alberts et al. |
| 8,710,252 | B2 | 4/2014 | Pace-Asciak et al. |
| 9,388,127 | B2 * | 7/2016 | Kinsella ............... C07D 213/53 |
| 9,522,877 | B2 * | 12/2016 | Kinsella ............... A61K 31/216 |
| 9,630,915 | B2 * | 4/2017 | Kinsella ............... C07D 213/71 |
| 9,718,781 | B2 * | 8/2017 | Kinsella ............... A61K 31/216 |
| 9,932,304 | B2 * | 4/2018 | Kinsella ................. A61P 43/00 |
| 10,357,504 | B2 * | 7/2019 | Kinsella .................... A61P 9/12 |
| 2003/0232877 | A1 | 12/2003 | Sikorski et al. |
| 2004/0213818 | A1 | 10/2004 | Kashiwabara et al. |
| 2005/0010279 | A1 | 1/2005 | Tenerz et al. |
| 2005/0015136 | A1 | 1/2005 | Ikeuchi et al. |
| 2005/0025705 | A1 | 2/2005 | Wang |
| 2005/0043788 | A1 | 2/2005 | Luo et al. |
| 2005/0152943 | A1 | 7/2005 | Hezi-Yamit et al. |
| 2006/0122143 | A1 | 6/2006 | Boyer et al. |
| 2007/0168015 | A1 | 7/2007 | Momma et al. |
| 2009/0062904 | A1 | 3/2009 | Furst |
| 2009/0311299 | A1 | 12/2009 | Falotico et al. |
| 2010/0023115 | A1 | 1/2010 | Robaina et al. |
| 2011/0099785 | A1 | 5/2011 | Pacetti |
| 2016/0102051 | A1 | 4/2016 | Kinsella et al. |

FOREIGN PATENT DOCUMENTS

| | | |
|---|---|---|
| WO | 2011/057262 A2 | 5/2011 |
| WO | 2013/156871 A2 | 10/2013 |

OTHER PUBLICATIONS

Born, 1963, The Aggregation of Blood Platelets, J Physiol 168:178-95.

Bousser et al., 2009, Rationale and design of a randomized, double-blind, parallel-group study of terutroban 30; mg/day versus aspirin 100 mg/day in stroke patients: the prevention of cerebrovascular and; cardiovascular events of ischemic origin with terutroban in patients with a history of ischemic; stroke or transient ischemic attack (PERFORM) study, PERFORM Study Investigators. Cerebrovasc Dis. 27(5):509-18.

Bousser et al., 2009, The Prevention of cerebrovascular and cardiovascular events of ischemic origin with terutroban in patients with a history of ischemic stroke or transient ischemic attack (PERFORM) study: baseline characteristics of the population, PERFORM Study Investigators. Cerebrovasc Dis. 27(6):608-13.

Bousser et al., 2011, Terutroban versus aspirin in patients with cerebral ischaemic events (PERFORM): a; randomised, double-blind, parallel-group trial, PERFORM Study Investigators. Lancet. 11;377(9782):2013-22. Epub May 25, 2011. Erratum in: Lancet. Jul. 30, 2011;378(9789):402.

Bousser et al., 2011, The Prevention of cerebrovascular and cardiovascular events of ischemic origin with terutroban in patients with a history of ischemic stroke or transient ischemic attack (PERFORM) study: baseline characteristics of the population, PERFORM Study Investigators. Cerebrovasc Dis. 27(6):608-13.

Cherdon et al., 2011, BM-573 inhibits the development of early atherosclerotic lesions in Apo E deficient mice by; blocking TP receptors and thromboxane synthase, Prostaglandins Other Lipid Mediat. 94:124-32.

Choi et al., 2011, New therapeutic approaches to combat arterial thrombosis: better drugs for old targets,; novel targets, and future prospects, Mol Interv. 11(2):111-23.

Custodi et al., 2012, Fitting the complexity of GPCRs modulation into simple hypotheses of ligand design, Journal of Molecular Graphics and Modelling 38:70-81.

Dogne et al., 2004, Pharmacological Characterization ofN-tert-Butyl-N-[2-(4-methylphenylamino)-5-nitrobenzenesulfonyl]urea (BM-573), a; Novel Thromboxane A2Receptor Antagonist and Thromboxane; Synthase Inhibitor in a Rat Model of Arterial Thrombosis and; Its Effects on Bleeding Time, JPET 309(2):498-505.

Fiessinger et al., 2010, Thromboxane Antagonism with terutroban in Peripheral Arterial Disease: the TAIPAD; study, TAIPAD investigators. J Thromb Haemost. 8(11):2369-76.

Ghuysen et al., 2005, Pharmacological profile and therapeutic potential of BM-573, a combined thromboxane; receptor antagonist and synthase inhibitor, Cardiovasc Drug Rev. 23(1):1-14.

Hanson et al., 2005, In vitro and in vivo pharmacological characterization of BM-613 [N-n-pentyl-N-[2-(4-methylphenylamino)-5-nitrobenzenesulfonyl]urea, a novel dual thromboxane synthase inhibitor and thromboxane receptor antagonist, The Journal of Phramacology and Experimental Therapeutics 313(1):293-301.

Hanson et al., 2006, Synthesis and Pharmacological Evaluation of Novel Nitrobenzenic Thromboxane Modulators as Antiplatelet Agents Acting on Both the Alpha and Beta Isoforms of the Human Thromboxane Receptor, Journal of Medicinal Chemistry 49(12):3701-3709.

Hanson et al., 2007, Design, Synthesis, and SAR study of a Series of N-Alkyl-N'[2-(aryloxy)-5-nitrobenzenesulfonyl]ureas and-cyanoguanidine as Selective Antagonists of the TP[alpha] and TP[beta] Isoforms of the Human Thromboxane A2 Receptor, Journal of Medicinal Chemistry 50(16):3928-3936.

Hirata et al., 2011, Prostanoid receptors, Chemical Reviews 111:6209-6230.

International Search Report and Written Opinion dated Aug. 31, 2016, for International Patent Application PCT/IB2016/000960 with International filing date Jun. 13, 2016 (19 pages).

International Search Report and Written Opinion dated May 9, 2014, for International Patent Application No. PCT/IB2013/001258, filed Apr. 17, 2013 (22 pages).

International Search Report and Written Opinion dated Oct. 11, 2013, for International Patent Application No. PCT/IB2013/001104, filed Apr. 17, 2013 (17 pages).

Jenkins et al., 2005, Bioluminescent human breast cancer cell lines that permit rapid and sensitive in vivo detection of mammary tumors and multiple metastases in immune deficient mice, Breast Cancer Res 7:444-454.

Kassack et al., 2002, Quantitative comparison of functional screening by measuring intracellular Ca2+ with radioligand binding at recombinant human dopamine receptors, AAPS Pharmsci 4(4):102-111.

Kolh et al., 2005, Effects of dobutamine on left ventriculoarterial coupling and mechanical efficiency in; acutely ischemic pigs, J Cardiovasc Pharmacol. 45(2):144-52.

Matsui et al., 2012, Thromboxane A2 receptor signaling facilitates tumor colonization through P-selectin-mediated interaction of tumor cells with platelets and endothelial cells, Cancer Science 103(4):700-707.

Ogletree et al., 1985, Pharmacological actions of SQ 29,548, a novel selective thromboxane antagonist, J. Pharmacol Exp Ther 234:435-441.

Rolin et al, 2001, Activity of a novel dual thromboxane A2receptor antagonist and thromboxane synthase inhibitor (BM-573) on platelet function and isolated smooth muscles, Prostaglandins, Leukotrienes, and Essential Fatty Acids 65(2):67-72.

Rolin et al, 2003, BM-573, a dual 1-5, thromboxane synthase inhibitor and 10-19, thromboxane receptor antagonist, prevents 22-30 pig myocardial infarction induced by coronary thrombosis, The Journal of Phramacology and Experimental Therapeutics 306(1):59-65.

Rolin et al., 2004, Pharmacological evaluation of both enantiomers of (R,S)-BM-591 as thromboxane A2; receptor antagonists and thromboxane synthase inhibitors, Other Lipid Mediat. 74(1-4):75-86.

Ruef et al., 2006, Coronary stent thrombosis related to aspirin resistance: What are the underlying mechanisms?, J Inter. Cardiol. 19:507-509.

Turner et al., 2011, Identification of an interaction between the TPalpha and TPbeta isoforms of the human thromboxane A2 receptor with protein kinase C-related kinase (PRK) 1: implications for prostate cancer.; ; J. Biol. Chem., 29;286(17):15440-57.

* cited by examiner

THROMBOXANE RECEPTOR ANTAGONISTS

CROSS-REFERENCE TO RELATED APPLICATION

This application is a continuation of U.S. patent application Ser. No. 15/901,503, filed Feb. 21, 2018, which application is a continuation of U.S. patent application Ser. No. 15/180,805, filed Jun. 13, 2016, now issued as U.S. Pat. No. 9,932,304, which application claims the benefit and priority of U.S. Provisional Patent Application Ser. No. 62/180,317, filed Jun. 16, 2015, the contents of which are incorporated by reference.

TECHNICAL FIELD

The invention relates to T prostanoid receptor (TP) antagonists and to their uses.

BACKGROUND

The prostanoid thromboxane (TX) $A_2$ is a potent mediator of platelet aggregation and constrictor of various types of smooth muscle (SM) including vascular, renal/kidney, pulmonary/bronchial and prostate SM. $TXA_2$ is also a potent pro-inflammatory mediator and immune modulatory agent, being abundantly produced by platelets, by various types of SM, by endothelial cells and also by inflammatory monocyte-derived macrophages. Hence, $TXA_2$ plays an essential role in the cardiovascular (CV), renal, pulmonary and prostate systems and in immunity and inflammation. Imbalances in signalling and/or alterations in the levels of $TXA_2$ or of its $TXA_2$ receptor, which is also referred to as the T prostanoid receptor or, in short, as the TP, have been implicated in various cardiovascular (e.g thrombosis, atherothrombosis, peripheral arterial disease, myocardial infarction, stroke and transient ischemic attack/TIA, acute coronary syndrome/ACS, systemic and pregnancy induced hypertension), renal (including glomerular nephritis and renal hypertension), pulmonary (including asthma and pulmonary arterial hypertension/PAH) and prostate (e.g benign prostate hyperplasia/BPH) diseases, and in the several inflammatory diseases associated with those systems and conditions. More recently, the role for $TXA_2$, $TXA_2$ synthase (TXAS) and its receptor, the TP, in neoplastic disease has been firmly established, including in cancers of the bladder, prostate, breast and lung where $TXA_2$ can promote tumour cell proliferation, migration, invasion, angiogenesis, inflammation and immunity, amongst other tumour-promoting actions. In humans, $TXA_2$ actually signals through two distinct receptor (iso)forms termed TPα and TPβ that are encoded by the same gene and which differ exclusively in their intracellular carboxyl-terminal (C)-tail domains. The TPs (TPα and TPβ) are expressed in a range of cells throughout the body including in platelets, in various types of SM, in endothelial cells and in macrophages, for example.

Due to the roles of $TXA_2$ in the CV, renal, pulmonary and prostate systems, there is significant clinical interest in the development of TP antagonists, not least for the treatment of atherothrombosis and other CV, renal and pulmonary disorders. TP antagonists also have potential applications in the treatment of various pro-inflammatory (including but not limited to inflammatory CVD, CVD associated with types 1 and 2 diabetes mellitus, renal and pulmonary diseases, post-viral/microbial infection), neoplastic and prostate (such as benign prostate hyperplasia/BPH) diseases. Other traditional therapeutic approaches currently used as alternatives to TP antagonists aim to inhibit the biosynthesis of $TXA_2$. Amongst these are the class of cyclooxygenase (COX) inhibitors referred to as the non-steroidal anti-inflammatory drugs (NSAIDs), which includes Aspirin and related COX 1 and/or COX 2 inhibitors. These COX inhibitors act by inhibiting the conversion of arachidonic acid into the endoperoxide prostaglandin (PG) $G_2/PGH_2$, the first enzymatic step in the synthesis of $TXA_2$ and of the related prostanoids which includes $PGD_2$, $PGE_2$, $PGF_{2\alpha}$ and $PGI_2$/prostacyclin. As one of the major sites of $TXA_2$ synthesis is the anucleated platelet, which mainly express COX 1 as opposed to COX 2, low-dose Aspirin is widely used to reduce/inhibit the synthesis of $TXA_2$ within platelets while not substantially affecting the synthesis of the other prostanoids by COX 1 or COX 2 in other nucleated cells. Hence, low-dose Aspirin is widely used to prevent excessive thrombosis in patients at risk of CV episodes by inhibiting $TXA_2$ generation in the anucleated platelet.

Recognition for a need to develop TP antagonists has increased in recent years mainly due to the fact that such traditional approaches involving the use of low-dose Aspirin are not sufficiently efficacious, e.g., in reducing thrombosis in at-risk patients, and/or due to its associated side-effects due to its indiscriminate inhibition of the synthesis of the other prostanoids ($PGD_2$, $PGE_2$, $PGF_{2\alpha}$ and $PGI_2$/prostacyclin). Lack of efficacy can also occur due to the fact that a relatively high percentage of the general population displays "Aspirin-resistance", a failure to lower $TXA_2$ levels in response to Aspirin therapy. Furthermore, increased incidence of adverse CV episodes can occur in patients receiving COXIB (COX 2 selective inhibitors) therapy, suggesting that more targeted TP receptor antagonism, rather than COX1/2 inhibition, may be a more a clinically beneficial way to inhibit the adverse effects of $TXA_2$. Moreover, TP antagonists, but not Aspirin or other NSAIDS or COXIBs, will inhibit the actions of $TXA_2$ and of the free-radical derived isoprostane 8-iso-prostaglandin (PG) $F_{2\alpha}$ and of all other incidental TP ligands (e.g., the endoperoxide $PGG_2/PGH_2$, 20-hydroxyeicosatetraenoic acid/20-HETE) that also act as full or partial agonists of the TP.

SUMMARY

The invention generally provides compounds that bind to thromboxane (TX) $A_2$ receptors (the TP) and inhibit thrombosis and other events within the cardiovascular, renal, pulmonary, or other systems where the TP is expressed including, but not limited to, platelets, various types of smooth muscle (SM) cells, endothelial cells, monocytes/macrophages and certain cells of the immune system. Compounds of the invention antagonize $TXA_2$, and other incidental TP ligands including the endoperoxide $PGG_2/H_2$, 20-HETE and isoprostanes (e.g., 8-iso-$PGF_{2\alpha}$) binding to the TP and stimulating platelet activation and aggregation, thereby decreasing the risk of a clinically significant thrombus or embolus, or antagonize the TPα and/or TPβ isoforms expressed in cells of the cardiovascular, renal, pulmonary or other systems. Thus, the TP antagonists of the invention provide beneficial pharmaceutical properties for treating thrombosis and other events within the cardiovascular, renal, pulmonary or other systems where the TP is expressed and/or where its ligands are dysregulated.

Compounds of the invention as TP antagonists should act as therapeutic drugs for pulmonary arterial hypertension (PAH), not only inhibiting the excessive vasoconstriction but also preventing the micro-thrombosis and, potentially, limit the pulmonary artery remodeling, right ventricular (RV) hypertrophy, endothelial cell dysfunction and local inflammation found in PAH. Compounds of the invention may also directly suppress inflammation or proliferation pathways implicated in PAH. Added to this, as the TP also mediates the actions of 8-iso-PGF$_{2α}$, a free-radical derived isoprostane generated in abundance in the clinical setting of PAH, as well as in other diseases involving oxidative stress or injury and which mediates similar actions to TXA$_2$, compounds of the invention will also antagonize these effects in PAH. In addition, as TXA$_2$ is a potent pro-inflammatory and mitogenic agent promoting vascular remodeling, restenosis and/or hypertrophy and is the main cyclo-oxygenase (COX)-derived constrictor prostanoid within the lung, compounds of the invention will antagonize these effects.

Hence, compounds of the invention would have added advantage over other PAH therapeutic agents used in that such compounds would not only inhibit TXA$_2$, the main vaso-constricting prostaglandin produced in the lung but also inhibit the adverse actions of the oxidative-stress derived isoprostane 8-iso-PGF2α, in addition to those of TXA$_2$ itself. Besides PAH, in other diseases such as athero-thrombosis replacing the standard-of-care Aspirin with compounds of the invention will offer several advantages as they will: (i) not only block the action of TXA$_2$, PGG$_2$/PGH$_2$ and 20-HETE but also of Aspirin-insensitive TP agonists (e.g., 8-iso-PGF$_{2α}$, generated in abundance by free-radicals during oxidative injury); (ii) also (unlike Aspirin), will inhibit the TP expressed in cells of the vascular bed and in circulating macrophages/monocytes, present during the inflammatory atherothrombosis; (iii) overcome Aspirin-resistance, estimated to occur in ~33% of the population.

Compounds of the invention preferably include a benzenesulfonyl urea in which the benzene is substituted by a substituted biphenylyloxy group (e.g., at the 2 position) and by a nitrile group (e.g., at the 5 position), which compounds show promising results as TP-isoform selective TP antagonists.

In certain aspects, the invention provides a compound that includes a benzenesulfonyl urea in which the benzene is substituted at the 2 position by a substituted biphenylyloxy group and at the 5 position by a nitrile group and the urea is substituted by a halogen, an alkyl group, a halogenated alkyl group, an aryl group, or a halogenated aryl group, or a pharmaceutically acceptable salt thereof. In some embodiments, the biphenylyloxy group is substituted by a halogenated alkyl group, a halogenated methoxy group, a primary amide, a secondary amide, a tertiary amide, or a nitrile group.

In some embodiments, the compound is represented by formula (I):

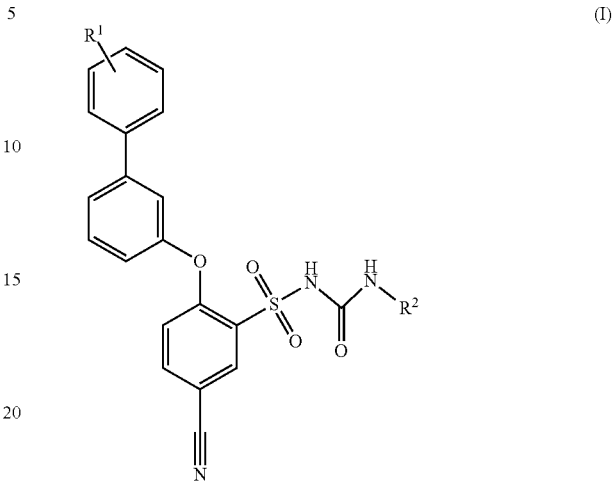

where R$^1$ is selected from the group consisting of: a halogen, an alkyl group, a cycloalkyl group, an aryl group, a heterocycloalkyl group, a halogenated alkyl group, a halogenated cycloalkyl group, a halogenated aryl group, a halogenated heterocycloalkyl group, a halogenated methoxy group, an ethoxy group, an isopropoxy group, a tert-butoxy group, a halogenated ethoxy group, a halogenated isopropoxy group, a halogenated tert-butoxy group, a primary amide, a secondary amide, a tertiary amide, OH, a halogen, CO$_2$H, methyl ketone, a nitrile group, a methyl ester group, an ethyl ester group, an isopropyl ester group, a tert-butyl ester group, a halogenated methyl ester group, a halogenated ethyl ester group, a halogenated isopropyl ester group, and a halogenated tert-butyl ester group; and R$^2$ is selected from the group consisting of a halogen, an alkyl group, a halogenated alkyl group, an aryl group, and a halogenated aryl group, or a pharmaceutically acceptable salt thereof. In a preferred embodiment, R$^1$ is selected from the group consisting of: a halogen, an alkyl group, a halogenated alkyl group, a halogenated cycloalkyl group, a halogenated aryl group, a halogenated heterocycloalkyl group, a methoxy group, an ethoxy group, an isopropoxy group, a tert-butoxy group, a halogenated ethoxy group, a halogenated isopropoxy group, a halogenated tert-butoxy group, a primary amide, a secondary amide, a tertiary amide, and a nitrile group; and R$^2$ is selected from the group consisting of a halogen, an alkyl group, a halogenated alkyl group, an aryl group, and a halogenated aryl group, or a pharmaceutically acceptable salt thereof.

In certain embodiments, the invention provides a compound of formula (I), in which R$^1$ is selected from the group consisting of: a halogenated alkyl group, a halogenated methoxy group, a primary amide, a secondary amide, a tertiary amide, and a nitrile group; and R$^2$ is selected from the group consisting of an alkyl group of 3 to 6 carbons, and a halogenated alkyl group of 3 to 6 carbons, or a pharmaceutically acceptable salt thereof.

In certain embodiments, the invention provides a compound of formula (I), in which R$^1$ is selected from the group consisting of: a difluoromethyl group, a trifluoromethyl group, a difluormethoxy group, a trifluormethoxy group, a primary amide, a secondary amide, a tertiary amide, and a nitrile group; and R$^2$ is selected from the group consisting of an alkyl group of 6 or fewer carbons and a halogenated alkyl group of 6 or fewer carbons, or a pharmaceutically acceptable salt thereof.

In other embodiments, the invention provides a compound of formula (II):

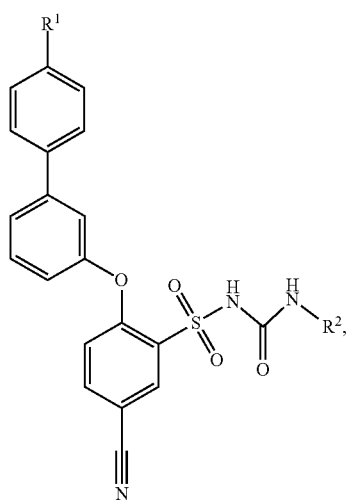

(II)

where $R^1$ is selected from the group consisting of: a halogen, an alkyl group, a cycloalkyl group, an aryl group, a heterocycloalkyl group, a halogenated alkyl group, a halogenated cycloalkyl group, a halogenated aryl group, a halogenated heterocycloalkyl group, a halogenated methoxy group, an ethoxy group, an isopropoxy group, a tert-butoxy group, a halogenated ethoxy group, a halogenated isopropoxy group, a halogenated tert-butoxy group, a primary amide, a secondary amide, a tertiary amide, OH, a halogen, $CO_2H$, methyl ketone, a nitrile group, a methyl ester group, an ethyl ester group, an isopropyl ester group, a tert-butyl ester group, a halogenated methyl ester group, a halogenated ethyl ester group, a halogenated isopropyl ester group, and a halogenated tert-butyl ester group; and $R^2$ is selected from the group consisting of a halogen, an alkyl group, a halogenated alkyl group, an aryl group, and a halogenated aryl group, or a pharmaceutically acceptable salt thereof.

In other embodiments, the invention provides a compound of formula (II), in which $R^1$ is selected from the group consisting of: a halogen, an alkyl group, a halogenated alkyl group, a halogenated cycloalkyl group, a halogenated aryl group, a halogenated heterocycloalkyl group, a halogenated methoxy group, an ethoxy group, an isopropoxy group, a tert-butoxy group, a halogenated ethoxy group, a halogenated isopropoxy group, a halogenated tert-butoxy group, a primary amide, a secondary amide, a tertiary amide, and a nitrile group; and $R^2$ is selected from the group consisting of an alkyl group of 2 to 6 carbons, and a halogenated alkyl group of 2 to 6 carbons, or a pharmaceutically acceptable salt thereof.

In other embodiments, the invention provides a compound of formula (II), in which $R^1$ is selected from the group consisting of: a halogenated alkyl group, a halogenated methoxy group, a primary amide, a secondary amide, a tertiary amide, and a nitrile group; and $R^2$ is an alkyl group of 3 to 6 carbons, or a pharmaceutically acceptable salt thereof.

In a much preferred embodiment, the invention provides a compound of formula (II), in which $R^1$ is selected from the group consisting of: a difluoromethyl group, a trifluoromethyl group, a difluormethoxy group, a trifluormethoxy group, a primary amide, a secondary amide, a tertiary amide, and a nitrile group; and $R^2$ is selected from the group consisting of an alkyl group of 3 to 5 carbons and a halogenated alkyl group of 3 to 5 carbons, or a pharmaceutically acceptable salt thereof.

In preferred embodiments, the invention provides a compound of formula (III):

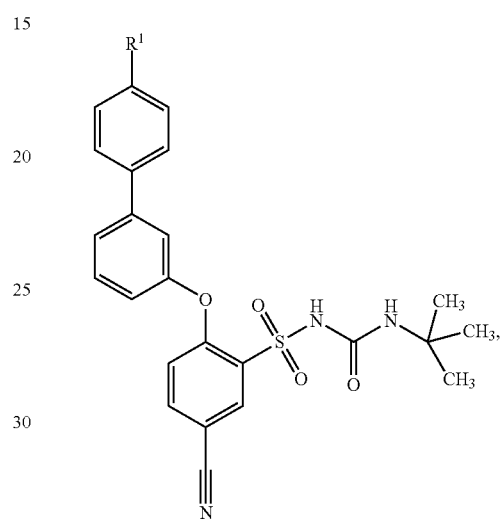

(III)

in which $R^1$ is selected from the group consisting of a difluoromethyl group, a trifluoromethyl group, a difluormethoxy group, a trifluormethoxy group, a primary amide, a secondary amide, a tertiary amide, and a nitrile group, or a pharmaceutically acceptable salt thereof. For example, the compound may be represented by formula (IV), (V), (VI), (VII), (VIII), (IX), (X), or (XI):

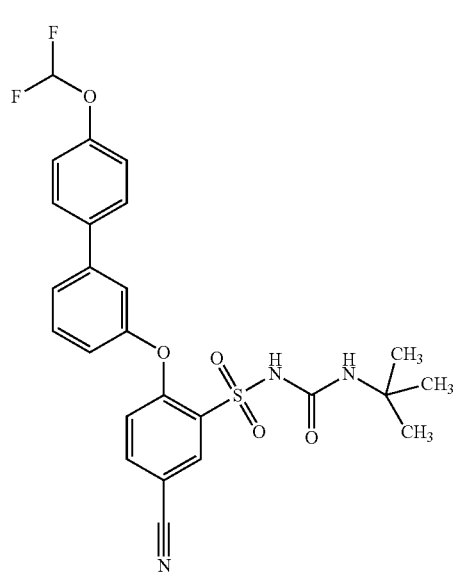

(IV)

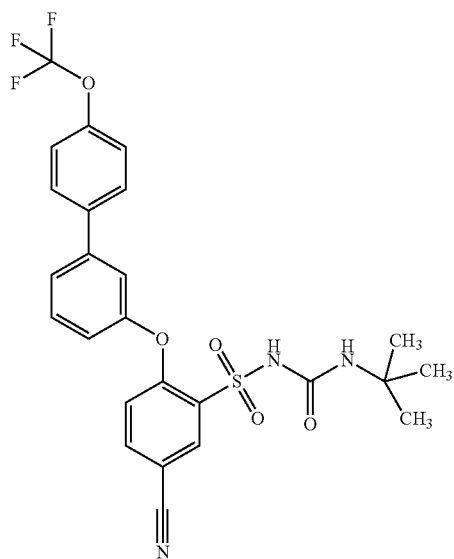
(V)
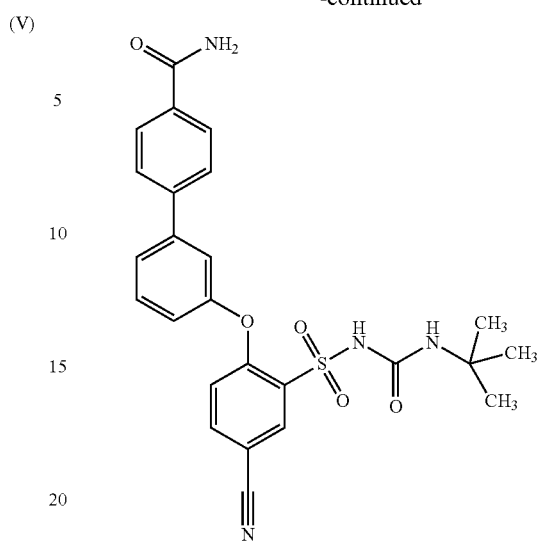
(VIII)
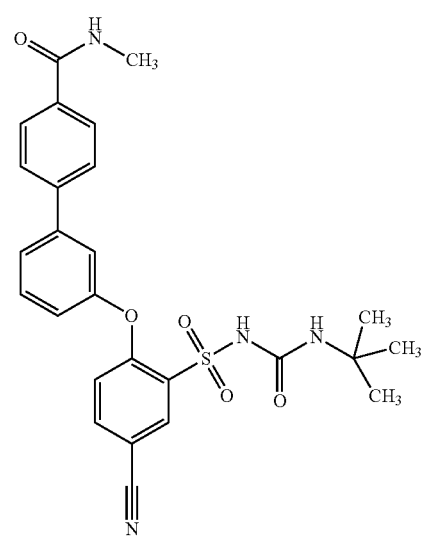
(VI)
(IX)
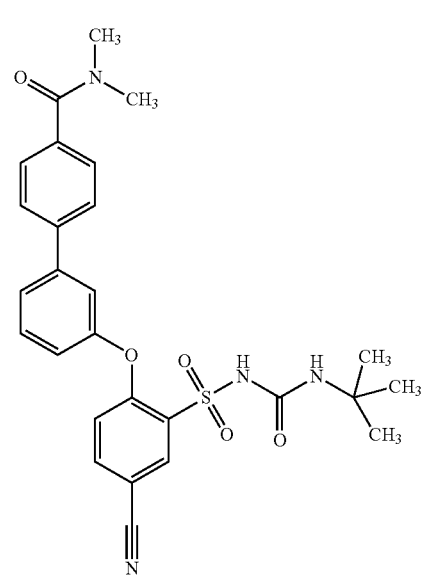
(VII)
(X)

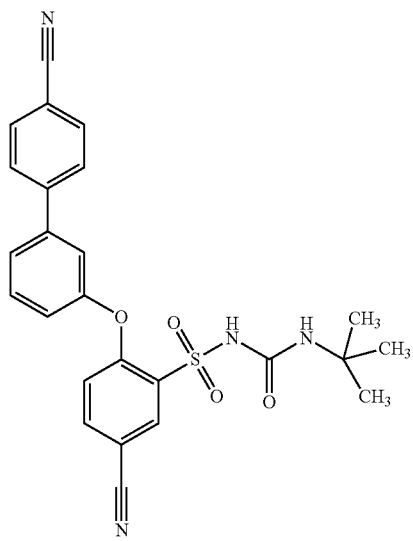

(XI)

or a pharmaceutically acceptable salt thereof.

In a much preferred embodiment, the invention provides a compound of formula (II) and more specifically as shown by formula (IV), (V), or (X):

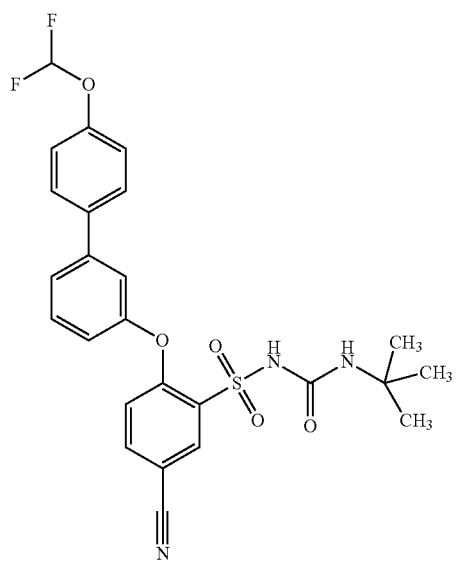

(IV)

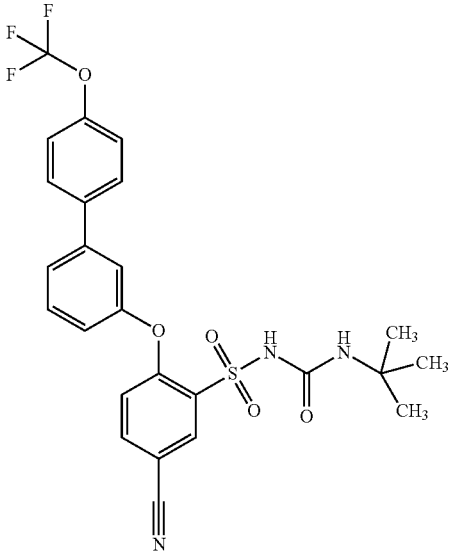

(V)

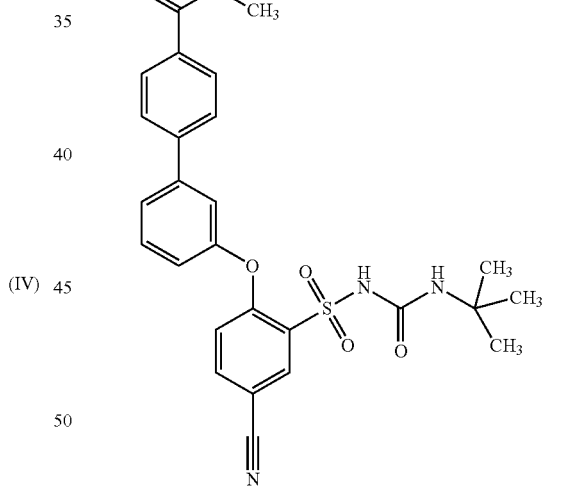

(X)

or a pharmaceutically acceptable salt thereof.

In one particular embodiment, in the invention provides a compound represented by formula (IV):

or a pharmaceutically acceptable salt thereof.

In a second particular embodiment, in the invention provides a compound represented by formula (V):

(V)

or a pharmaceutically acceptable salt thereof.

In a third particular embodiment, in the invention provides a compound represented by formula (X):

(X)

or a pharmaceutically acceptable salt thereof.

Compounds of the invention can be used to treat human diseases in which human thromboxane (TX) $A_2$ receptors/T Prostanoid receptors/TPs play a role.

Compounds of the invention can be used to treat human diseases where there is altered expression in the levels of the human TPs.

Compounds of the invention can be used to treat human diseases in which there are elevated levels of $TXA_2$ Compounds of the invention can be used to treat human diseases in which there are elevated levels of other bio-chemical entities/ligands (eg $PGG_2/PGH_2$, 20-HETE or isoprostanes including 8-iso $PGF_{2\alpha}$) that act through the human TPs.

Compounds of the invention can be used to treat human diseases in which there is elevated levels of non-enzymatic, free-radical derived isoprostanes that signal through the human TPs such as 8-iso-$PGF_{2\alpha}$.

Compounds of the invention can be administered by different routes of administration including oral, inhalation, nebulization, transdermal, intravenous, sub-cutaneous, transmusosal, implantable depot formulation Compounds of the invention can be used to antagonise the TP for use in the treatment of pulmonary arterial hypertension (PAH).

Compounds of the invention can be used to treat pulmonary arterial hypertension (PAH) when used in combination with other drugs approved to treat this disease.

Compounds of the invention can be used in combination with implantable sensors to measure pulmonary artery pressure, the therapeutic administration or therapeutic dosing of such compounds optimised or adjusted to changes in such measured pulmonary artery pressure.

Compounds of the invention can be used to treat thrombosis, either alone or in combination with other therapeutic agents.

Compounds of the invention can be used to treat microvessel thrombosis, either alone or in combination with other therapeutic agents Compounds of the invention can be used to treat other cardiovascular diseases, including those CVDs associated with types 1 and 2 diabetes mellitus. Examples of fields of application, but not limited to, include treatment of various cardiovascular diseases including prevention of excessive platelet aggregation associated atherothrombosis, ischemic stroke, transient ischemic attach (TIA), acute coronary syndrome. For these conditions, compounds of the invention can be used either alone or in combination with other therapeutics drugs.

Compounds of the invention can be used to treat other pulmonary diseases, including but not limited to asthma, and used either alone or in combination with other therapeutics drugs.

Compounds of the invention can be used to treat renal diseases and used either alone or in combination with other therapeutics drugs.

Compounds of the invention can be used to treat prostate diseases including, but not limited to benign prostate hyperplasia (BPH) and either alone or in combination with other therapeutics drugs.

Compounds of the invention can be used to treat inflammatory diseases, and either alone or in combination with other therapeutics drugs.

Compounds of the invention can be used to treat neoplastic diseases including cancers, and used either alone or in combination with other therapeutics drugs.

Compounds of the invention can be used to treat stroke and transient ischemic attack (TIA), and used either alone or in combination with other therapeutics drugs.

Compounds of the invention can be used in combination with immune modulators to treat cancers.

Compounds of the invention can be used to treat dysregulated smooth muscle cell function, such as but not limited to various types of hypertension and restenosis post-surgical stenting.

Compounds of the invention can be used to treat dysregulated endothelial cell function.

Compounds of the invention can be coated onto implantable medical devices for controlled or local delivery at sites of implantation of such medical devices including stents, balloons, stent grafts, prosthetic valves, shunts, abdominal aortic valves.

DETAILED DESCRIPTION

Figure 1:
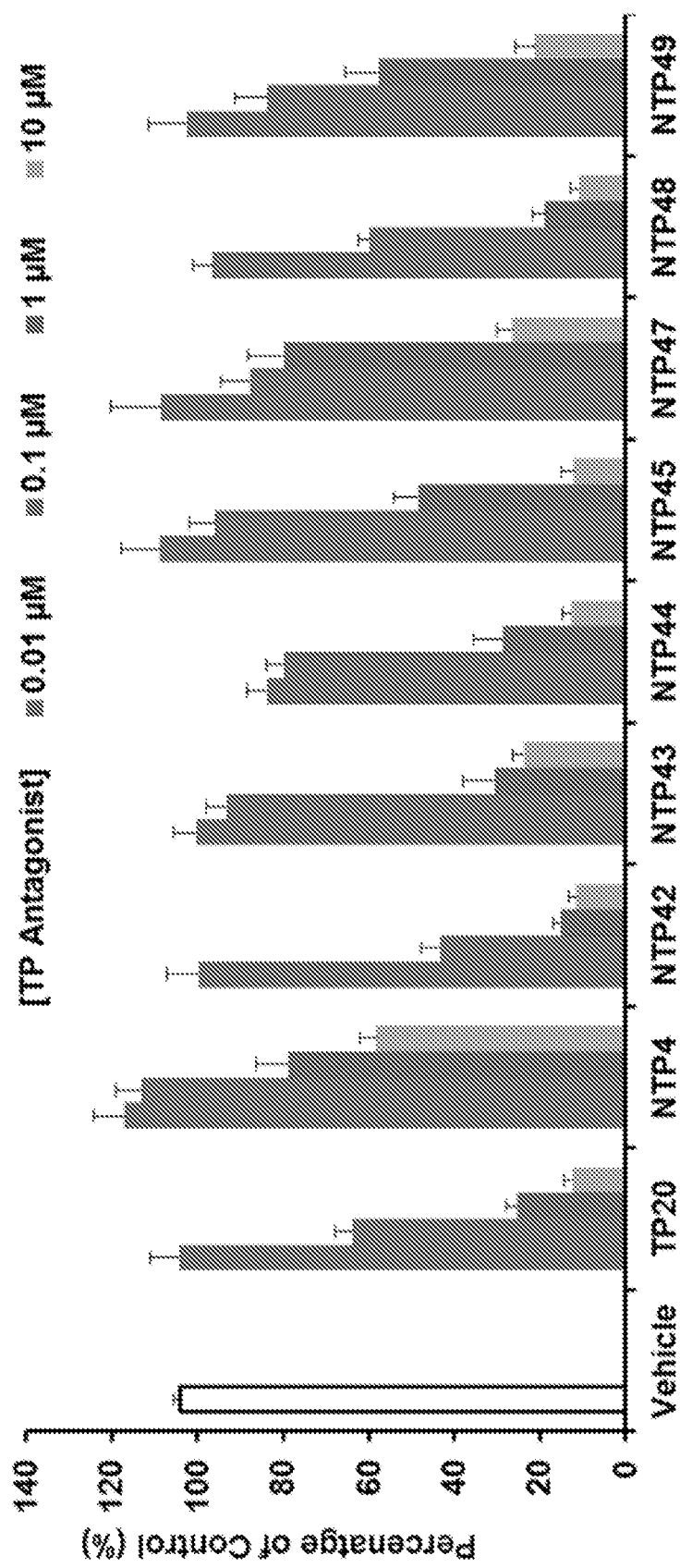
FIG. 1 shows the effect of compounds of the invention on U46619-mediated calcium mobilization in HEK TPα cells.

The invention relates to novel chemical entities that act as T prostanoid receptor (TP) antagonists and to their use in the treatment of human diseases in which thromboxane (TX) A and of all other agents that act as incidental ligands of the TP, including the endoperoxide prostaglandin (PG)G$_2$/PGH$_2$, 20-hydroxyeicosatetraenoic acid (20-HETE) and the free-radical derived isoprostanes (e.g 8-iso-prostaglandin (PG) F$_{2\alpha}$), play a role.

The invention generally relates to novel chemical entities/compounds that act as antagonists of the TP to prevent TXA$_2$, PGG$_2$/H$_2$, 20-HETE, isoprostanes including 8-iso-PGF$_{2\alpha}$ or any other incidental TP ligands binding to the TP expressed in humans. Compounds of the invention include those that exhibit preferential binding for either TPα and/or TPβ receptor subtype. As discussed herein, the invention provides small molecule compounds which, for example but not limited to, inhibit aggregation of human platelets, prevent pulmonary arterial hypertension (PAH) in a preclinical PAH model and-exhibit attractive ADME (absorption, distribution, metabolism, and excretion) properties. The invention further provides exemplary synthetic routes for the novel TP antagonist compounds by way of example but not exhaustive of all routes of synthesis. Exemplary compounds of the invention are disclosed.

In some embodiments, compounds of the invention display significant TP selectivity and antagonistic activity ex vivo in human platelets and are effective in preventing pulmonary arterial hypertension (PAH) in a pre-clinical disease model of PAH.

Compounds of the invention preferably inhibit TXA$_2$-induced platelet aggregation at a half-maximal inhibitory concentration (IC$_{50}$) below 100 nM. Compounds of the invention preferably inhibit TXA$_2$-induced platelet aggregation at a half-maximal inhibitory concentration (IC$_{50}$) below 50 nM. Compounds of the invention preferably inhibit TXA$_2$-induced platelet aggregation at a half-maximal inhibitory concentration (IC$_{50}$) below 20 nM. Compounds of the invention preferably inhibit TXA$_2$-induced platelet aggregation at a half-maximal inhibitory concentration (IC$_{50}$) below 5 nM. Compounds of the invention prevent PAH in a pre-clinical model of PAH when used below 5 mg/kg/day. In certain embodiments, compounds of the invention further inhibit TXA$_2$-induced platelet aggregation but not aggregation induced by other platelet agonists such as, for example, thrombin or adenosine diphosphate (ADP). Further, compounds of the invention preferably do not agonize or antagonize signaling by several other G-protein coupled receptors, kinases, phosphatases, or ion channels including human Ether-á-go-go related gene (hERG).

Compounds of the invention exhibit attractive ADME properties. Compounds of the invention may exhibit the ability to inhibit TP agonist-induced intracellular calcium mobilization and inhibit platelet aggregation in ex vivo assays. In some embodiments, compounds of the invention may show no effect on signaling through other prostanoid receptors (prostaglandin (PG) D$_2$ receptor, DP; PGE$_2$ receptors EP$_1$-EP$_4$; PGF$_{2\alpha}$ receptor, FP; PGI$_2$/Prostacyclin receptor, IP) and non-prostanoid receptors including the purinergic (ADP) and thrombin (PAR1) receptors, also involved in platelet activation similar to the TP isoforms. Further, compounds exhibit minimal toxicity and favorable cell permeability.

Shown below are exemplary methods of synthesis of compounds of the invention. For synthesis of the compounds, reference will be made to SM 8.

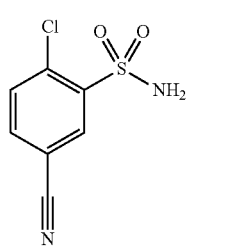

(SM 8)

Reference will also be made to intermediates i-1, i-2, i-3, i-4, i-5, i-6, and i-7.

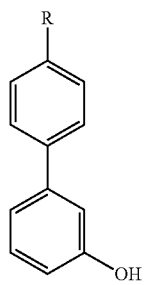

Where R=CHF2 (i-1), R=CF3 (i-2), R=CONH2 (i-3), R=CONHMe (i-4), R=CONMe2 (i-5), R=CN (i-6).

A synthetic route is outlined in Pathway 1.

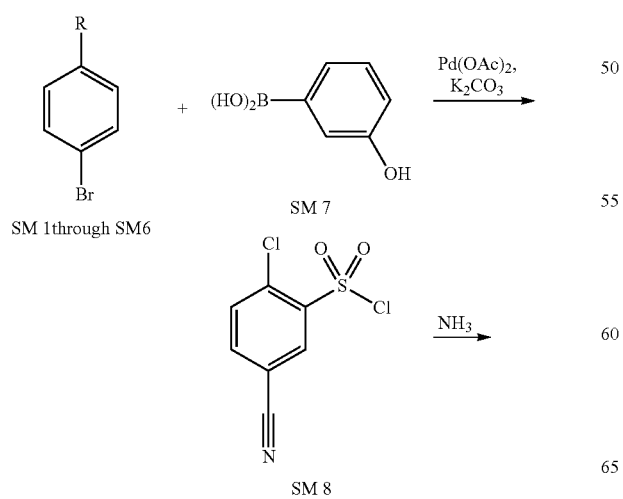

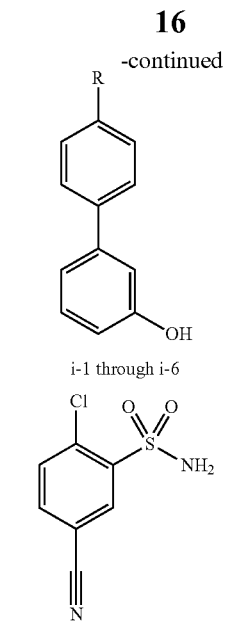

i-1 through i-6 i-7

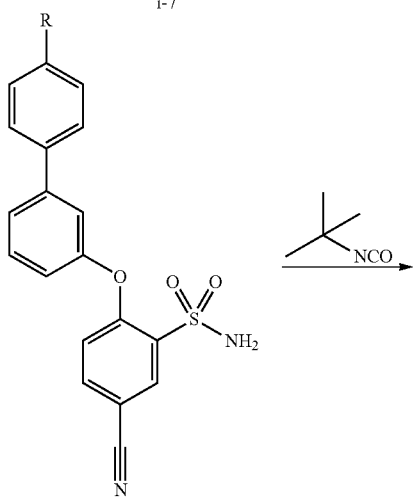

i-8 through i-13

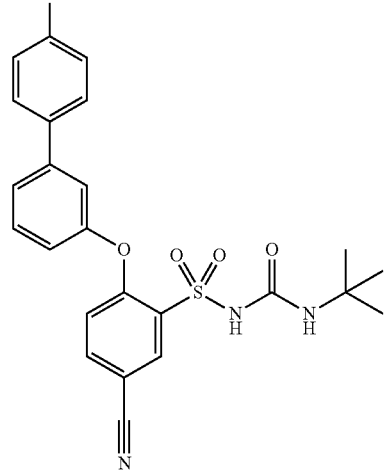

1-6

A range of aryl bromides (SM 1 to SM 6) undergoes palladium mediated coupling with 3-hydroxyphenylboronic acid (SM 7) to generate intermediates i-1 through i-6. The phenol intermediates i-1 to i-6 undergo ipso-substitution of the chlorine in i-7 (formed from SM 8) to give i-8 through i-14 which upon reaction with tert-butylisocyanate furnish compounds of the invention.

As shown in Scheme Pathway 2, the range of aryl bromides (SM 1 to SM 6) goes palladium mediated coupling with 3-hydroxyphenylboronic acid (SM 7) to generate intermediates i-1 through i-6, while i-7 is produced from SM 8.

Pathway 2

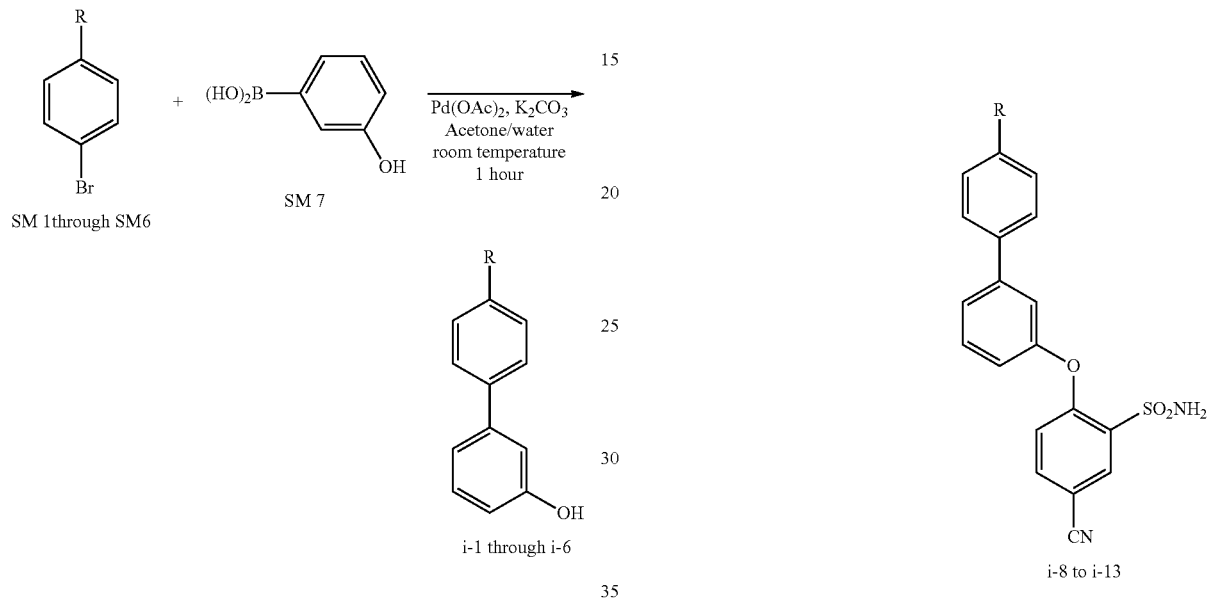

SM 8.1 is purchased and converted into the corresponding sulfonamide i-7.1 using Pathway 3.

Pathway 3

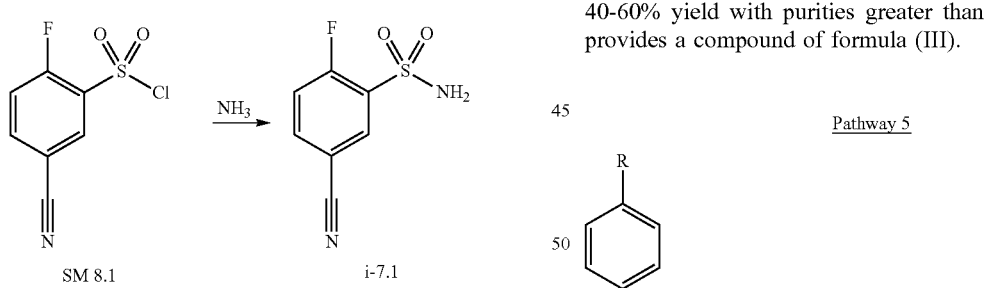

The fluoro intermediate i-7.1 is reacted with the six phenols i-1 through i-6 as shown in Pathway 4, which results in excellent conversions.

Pathway 4

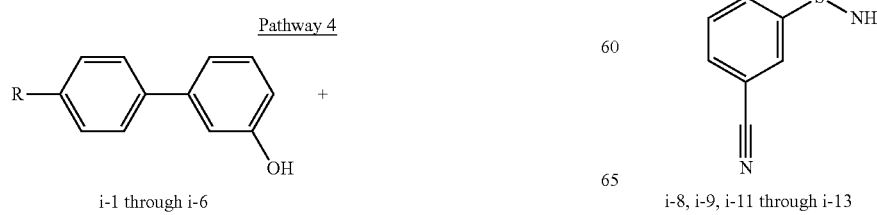

-continued

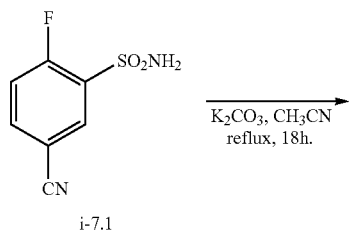

Intermediates i-8, i-9 and i-11 through i-13 undergo clean conversion with tert-butylisocyanate, Pathway 5, (>70% by LCMS) to furnish crude 1, 2, 4 to 6 which are purified by reverse phase preparative HPLC to furnish the targets in 40-60% yield with purities greater than 96%. Pathway 5 provides a compound of formula (III).

Pathway 5

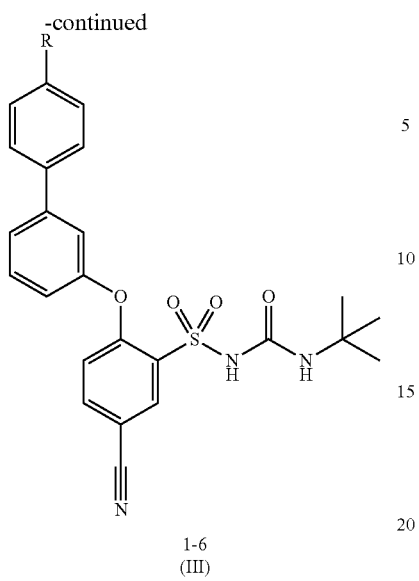

1-6
(III)

The preparation of 4-(3-hydroxyphenyl)benzonitrile (i-6) may include Pathway 6.

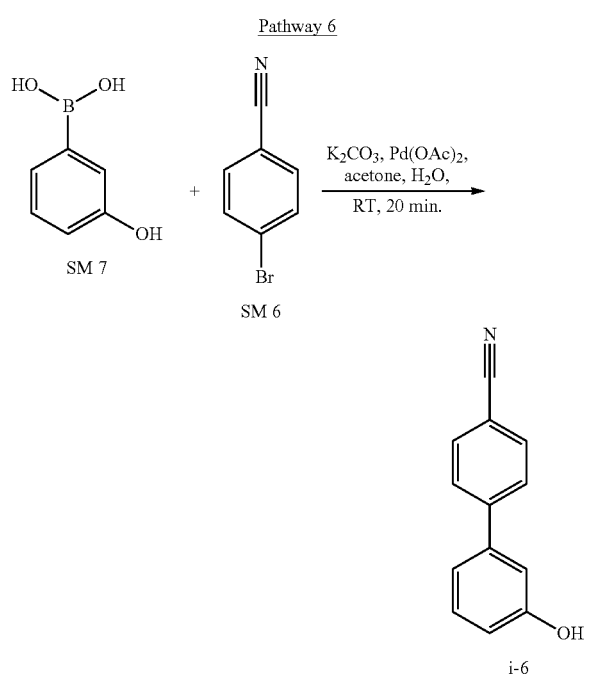

Nitrogen is bubbled through a mixture of 3-hydroxybenzeneboronic acid (SM 7, 2.00 g, 14.5 mmol), 4-bromobenzonitrile (SM 6, 2.90 g, 15.9 mmol) and potassium carbonate (2.20 g, 15.9 mmol) in acetone (65 mL) and H₂O (120 mL) for 5 minutes. Pd(OAc)2 (325 mg, 1.45 mmol) is added and the mixture is stirred under a nitrogen atmosphere at room temperature for 30 minutes, after which time LC-MS analysis shows the reaction to be complete. The reaction mixture is concentrated under vacuum, acidified with saturated aqueous NH₄Cl solution (50 ml) and extracted with DCM (200 ml then 2×75 mL). The combined organic phases are passed through a phase separator and concentrated to dryness under vacuum. The crude product is absorbed onto silica and purified by MPLC chromatography on a 100 g Biotage silica cartridge (eluting with DCM/EtOAc gradient 0 to 40%). The target compound, 4-(3-hydroxyphenyl)benzonitrile (i-6) is isolated as a white solid.

Compounds i-1 to i-5 are similarly prepared.

To arrive at 3-[4-(Difluoromethyl)phenyl]phenol (i-1) for use in the invention, SM (1, 1-bromo-4-(difluoromethyl)-benzene) may be used. (Eluting with iso-hexane/DCM gradient 0 to 100%). The target compound 3-[4-(difluoromethyl)phenyl]phenol (i-1) is isolated as a white solid.

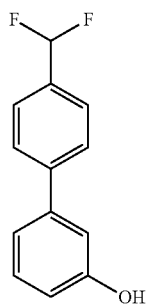

(i-1)

For 3-[4-(Trifluoromethyl)phenyl]phenol (i-2) for use in the invention, SM 2 (4-bromobenzotrifluoride) may be used. (Eluting with iso-hexane/DCM gradient 0 to 100%). The target compound 3-[4-(Trifluoromethyl)phenyl]phenol (i-2) is isolated as a white solid.

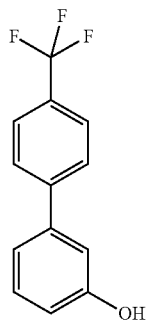

(i-2)

To make 4-(3-Hydroxyphenyl)benzamide (i-3) for use in the invention, SM-3 (4-Bromobenzamide) may be used. The generic procedure is modified and the crude reaction mixture is recrystallized from EtOAc). The target compound, 4-(3-hydroxyphenyl)benzamide (i-3) is isolated as a white solid.

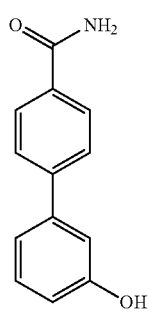

(i-3)

To make 4-(3-Hydroxyphenyl)-N-methyl-benzamide (i-4) for use in the invention, SM-4 (N-Methyl-4-bromobenzamide) may be used.

The target compound, 4-(3-hydroxyphenyl)-N-methyl-benzamide (i-4) is isolated as a white solid.

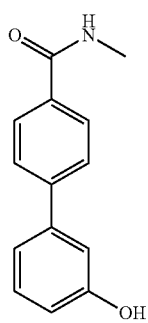

(i-4)

To make 4-(3-Hydroxyphenyl)-N,N-dimethyl-benzamide (i-5) for use in the invention, SM-5 (N,N-Dimethyl-4-bromobenzamide) may be used. The generic procedure is modified and the crude reaction mixture is recrystallized from EtOAc). The target compound, 4-(3-hydroxyphenyl)-N,N-dimethyl-benzamide (i-5) is isolated as a white solid.

(i-5)

Preparation of 5-cyano-2-fluoro-benzenesulfonamide (i-7.1) may include Pathway 7.

Pathway 7

SM 8.1    i-7.1

A solution of ammonia (7 M in MeOH, 4.5 mL, 31.5 mmol) is cooled in iced water and solution of 5-cyano-2-fluorobenzenesulfonyl chloride (SM 8.1, 0.99 g, 4.51 mmol) in THF (20 mL) is added drop wise. The reaction mixture is stirred for 30 minutes, after which time LC-MS analysis shows the reaction to be complete. The reaction mixture is concentrated under vacuum, water (40 ml) added and then extracted with DCM (100 ml then 2×50 mL). The organic phases are passed through a phase separator, combined and concentrated to dryness under vacuum to give 5-cyano-2-fluoro-benzenesulfonamide (i-7.1) as a white solid that is used without further purification.

Preparation of 4-[3-(4-cyano-2-sulfamoyl-phenoxy)phenyl]-N,N-dimethyl-benzamide (i-12) may include Pathway 8.

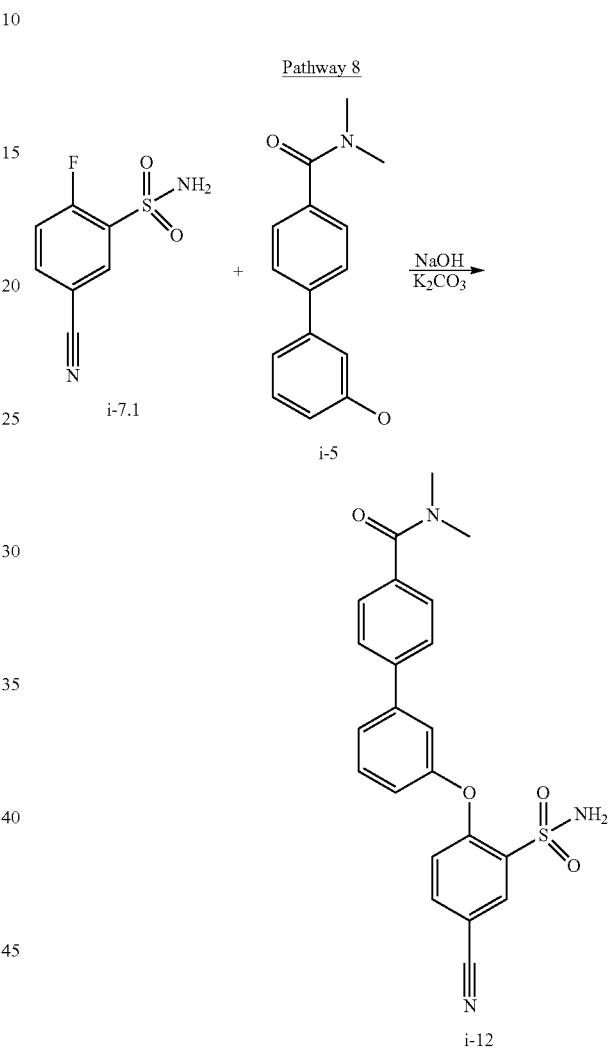

Here, 2.1M NaOH (0.55 mL, 1.15 mmol) is added to 4-(3-hydroxyphenyl)-N,N-dimethyl-benzamide (253 mg, 1.05 mmol) suspended in dioxan (7 mL) and stirred for 5 minutes. The mixture is concentrated to dryness under vacuum, dry acetonitrile (7 mL) added followed by 5-cyano-2-fluoro-benzenesulfonamide (126 mg, 0.63 mmol) and K2CO3 (609 mg, 4.41 mmol) and the reaction mixture is stirred at 85° C. overnight. LC-MS shows no sulphonamide remains. The reaction mixture is added to 2M HCl (10 mL), diluted with water (40 mL) and extracted with EtOAc (30 mL, 2×15 mL). The combined organic phases are washed with water (15 mL), dried (MgSO4) and concentrated to dryness under vacuum. The crude reaction is purified by MPLC chromatography on a 10 g Biotage silica cartridge (eluting with iso-hexane/EtOAc gradient 40 to 100%). The target compound, 4-[3-(4-cyano-2-sulfamoyl-phenoxy)phenyl]-N,N-dimethyl-benzamide (i-12) is isolated.

Similarly prepared were compounds i-8, i-9, i-11 and i-13 from phenols i-1, i-2, i-4 and i-6 respectively.

For 5-Cyano-2-[3-[4-(difluoromethyl)phenyl]phenoxy] benzenesulfonamide (i-8), i-1 (231 mg, 1.05 mmol) is used. (Eluting with iso-hexane/EtOAc gradient 5 to 45 100%). A compound, 5-cyano-2-[3-[4-(difluoromethyl)phenyl]phenoxy]benzenesulfonamide (i-8) is isolated.

For 4-[3-(4-Cyano-2-sulfamoyl-phenoxy)phenyl]-N-methyl-benzamide (i-11) i-4 (238 mg, 1.05 mmol) is used. (Eluting with iso-hexane/EtOAc gradient 40 to 100%). The compound 4-[3-(4-cyano-2-sulfamoylphenoxy)phenyl]-N-methyl-benzamide (i-11) is isolated.

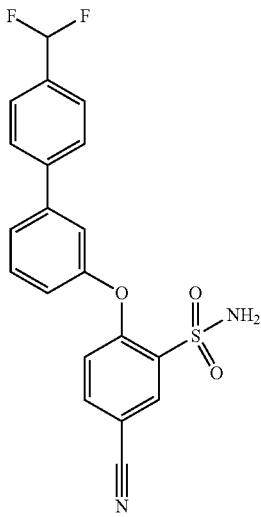

(i-8)

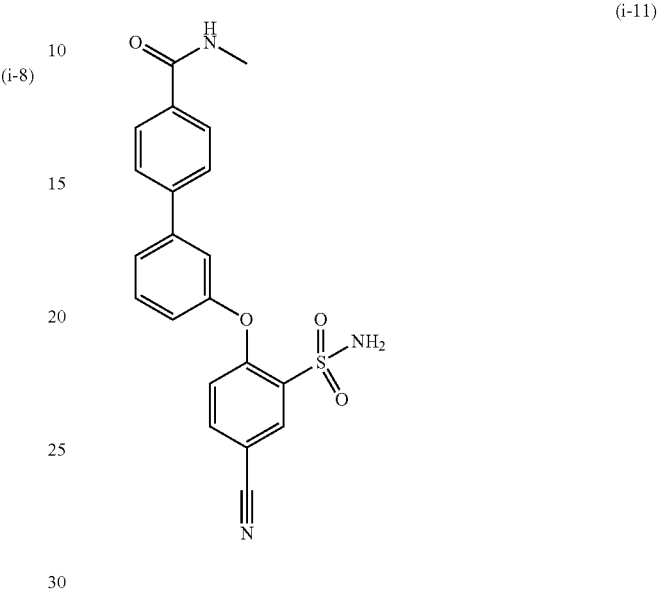

(i-11)

For 5-Cyano-2-[3-[4-(trifluoromethyl)phenyl]phenoxy] benzenesulfonamide (i-9) i-2 (250 mg, 1.05 mmol) is used. (Eluting with iso-hexane/EtOAc gradient 0 to 35%). The compound, 5-cyano-2-[3-[4-(trifluoromethyl)phenyl]phenoxy]benzenesulfonamide (i-9) is isolated.

For 5-Cyano-2-[3-(4-cyanophenyl)phenoxy]benzenesulfonamide (i-13), i-6 (205 mg, 1.05 mmol) is used. (Eluting with iso-hexane/EtOAc gradient 10 to 55%). The compound, 5-cyano-2-[3-(4-cyanophenyl)phenoxy] benzenesulfonamide (i-13) is isolated.

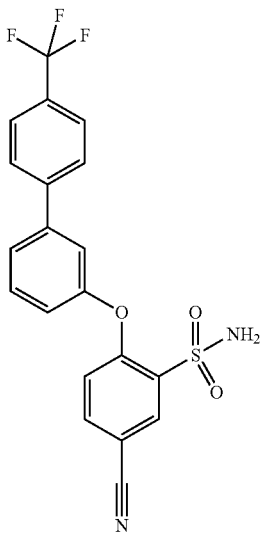

(i-9)

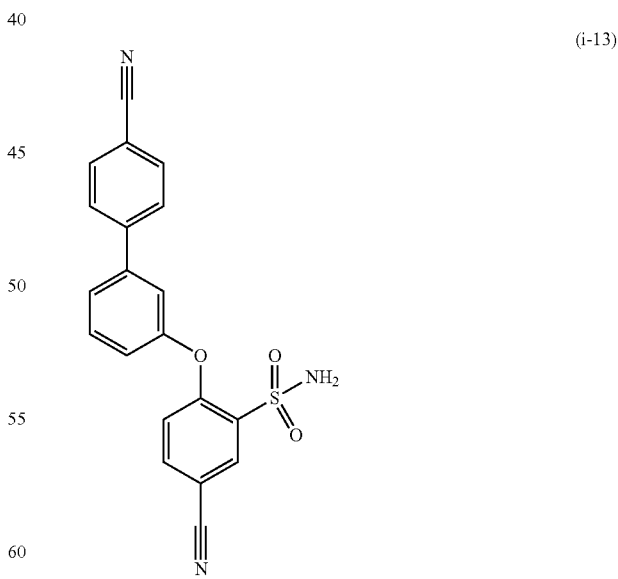

(i-13)

Compounds disclosed herein may be synthesized using the Pathway 9 for the generic preparation of N-(tert-Butyl-carbamoyl)-5-cyano-2-((4'-(substituted)-[1,1'-biphenyl]-3-yl)oxy)benzenesulfonamides (1 to 6).

Pathway 9

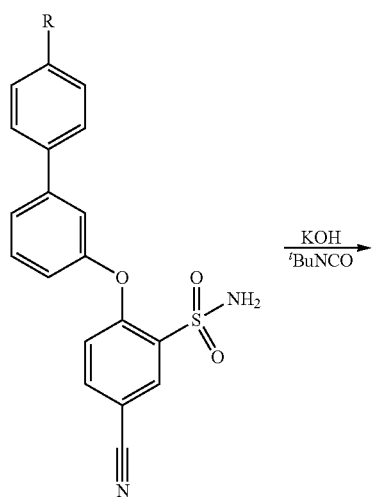

i-8: R = CF₂H
i-9: R = CF₃
i-11: R = CONHMe
i-12: R = CONMe₂
i-13: R = CN

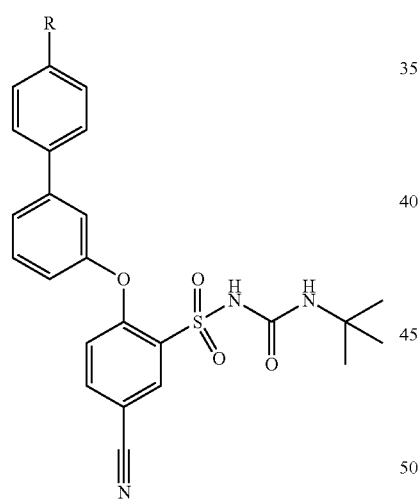

1: R = CF₂H
2: R = CF₃
4: R = CONHMe
5: R = CONMe₂
6: R = CN

The 5-cyano-2-((4'-(substituted)-[1,1'-biphenyl]-3-yl)oxy)benzenesulfonamides (i-8 to i-13) are stirred in dioxan (10 mL per mmol) and 3.1M KOH (1.1 eq.) added. The mixtures are stirred for 10 minutes then concentrated to dryness under vacuum. Dry DMF (7 mL per mmol) is added followed by tert-butyl isocyanate (2.5 eq.) and the reaction mixtures are stirred at room temperature for 18 hours. The reaction mixtures are concentrated under vacuum and 2M HCl (1.7 mL per mmol) added. This is then extracted with EtOAc (3×7 mL per mmol). The organic phases are combined and concentrated to dryness under vacuum. The residues are dissolved in DMSO and purified by reversed phase preparative HPLC. The target compounds are isolated as white solids in about 35-60% yields.

Methods of the invention may be used to produce 1-tert-Butyl-3-[5-cyano-2-[3-[4-(difluoromethyl)phenyl]phenoxy]phenyl]sulfonyl-urea (VI).

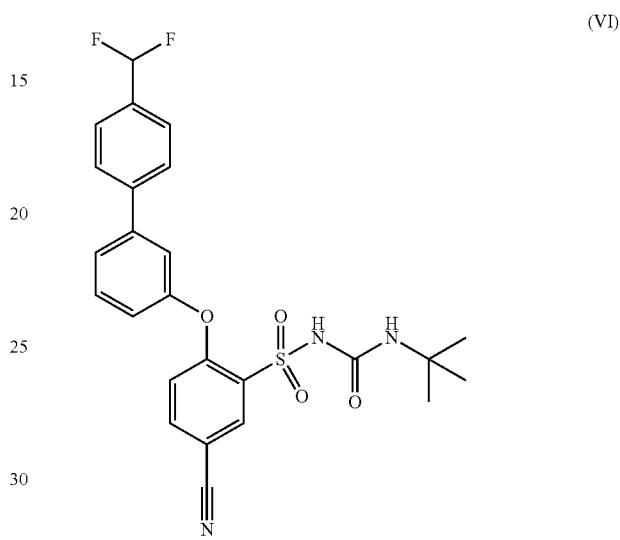

(VI)

Methods of the invention may be used to produce 1-tert-Butyl-3-[5-cyano-2-[3-[4-(trifluoromethyl)phenyl]phenoxy]phenyl]sulfonyl-urea (VII)

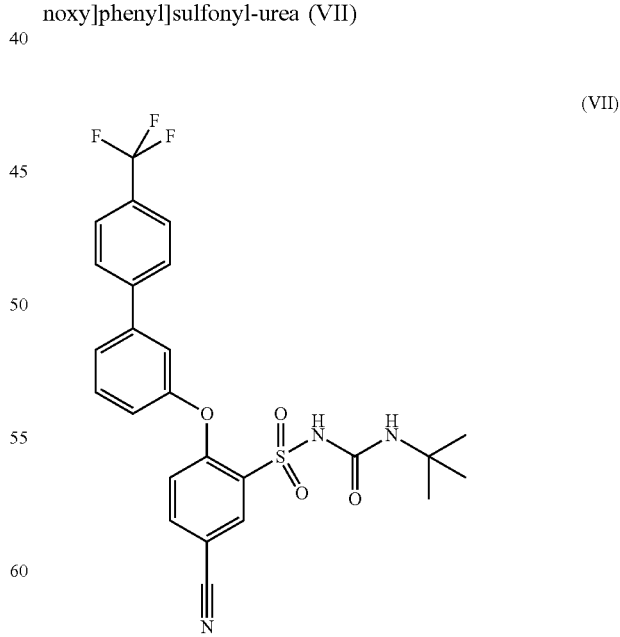

(VII)

Methods of the invention may be used to produce 4-[3-[2-(tert-Butylcarbamoylsulfamoyl)-4-cyano-phenoxy]phenyl]-N-methyl-benzamide (IX)

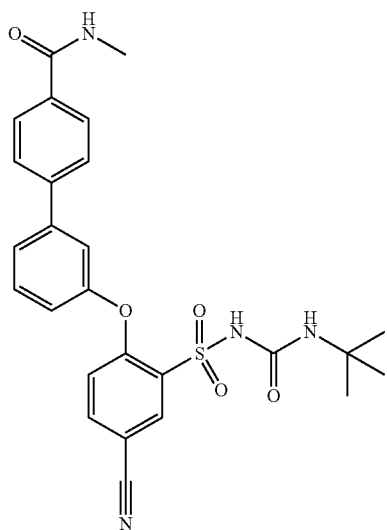

(IX)

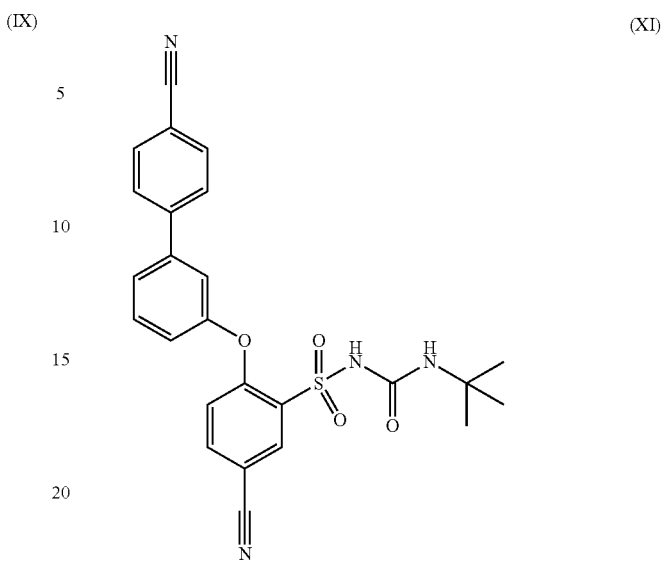

(XI)

Methods of the invention may be used to produce 4-[3-[2-(tert-Butylcarbamoylsulfamoyl)-4-cyano-phenoxy]phenyl]-N,N-dimethyl-benzamide (X)

Methods of the invention may be used in the production of a compound of formula (IV).

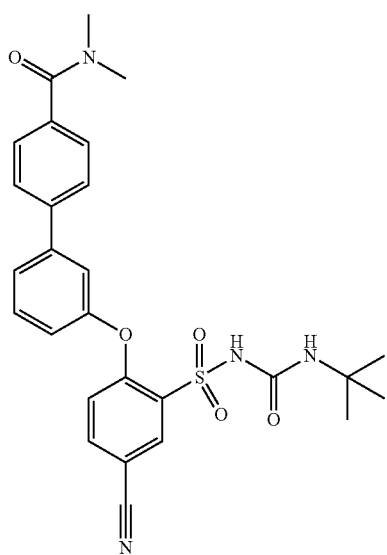

(X)

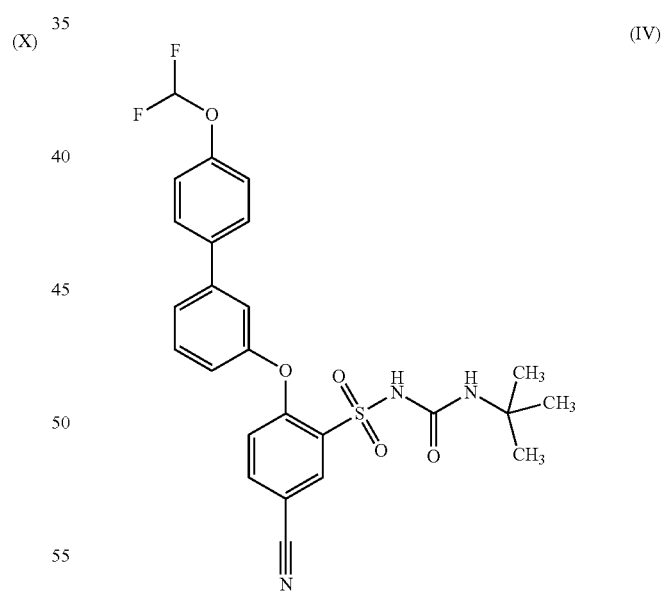

(IV)

Methods of the invention may be used to produce 1-tert-Butyl-3-[5-cyano-2-[3-(4-cyanophenyl)phenoxy]phenyl]sulfonyl-urea (XI).

Methods of the invention may be used in the production of a compound of formula (V).

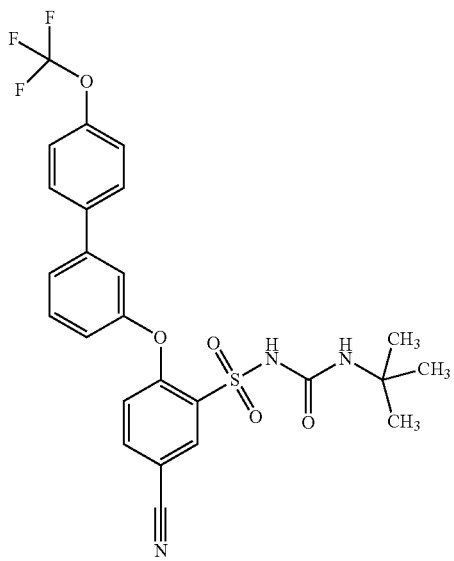

(V)

Methods of the invention may be used in the production of a compound of formula (VIII).

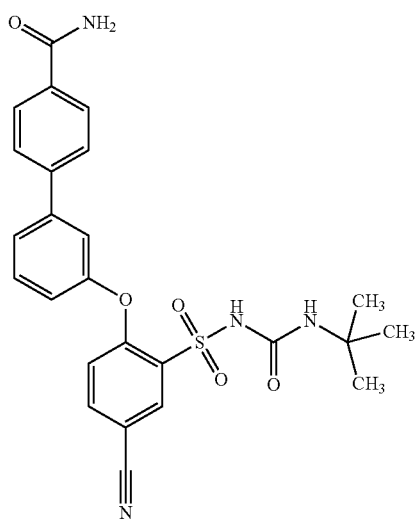

(VIII)

Thus it can be seen that methods of the invention may be used in the production of a compound of formula (II)

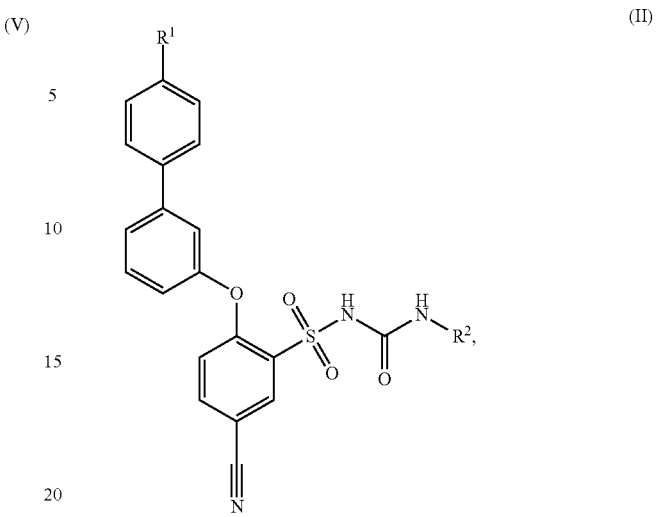

(II)

in which $R^1$ is a halogen, an alkyl group, a cycloalkyl group, an aryl group, a heterocycloalkyl group, a halogenated alkyl group, a halogenated cycloalkyl group, a halogenated aryl group, a halogenated heterocycloalkyl group, a halogenated methoxy group, an ethoxy group, an isopropoxy group, a tert-butoxy group, a halogenated ethoxy group, a halogenated isopropoxy group, a halogenated tert-butoxy group, a primary amide, a secondary amide, a tertiary amide, OH, a halogen, $CO_2H$, methyl ketone, a nitrile group, a methyl ester group, an ethyl ester group, an isopropyl ester group, a tert-butyl ester group, a halogenated methyl ester group, a halogenated ethyl ester group, a halogenated isopropyl ester group, or a halogenated tert-butyl ester group; and $R^2$ is a halogen, an alkyl group, a halogenated alkyl group, an aryl group, or a halogenated aryl group, or a pharmaceutically acceptable salt thereof.

Halogenated may be taken to mean substituted with one or more of F, CL, BR, I, and At, and preferably one or more of F and Cl.

Compounds of the invention can be in a pharmaceutically acceptable salt form or as the free base. Suitable routes of administration include oral, buccal, topical (including transdermal), injection, intravenous, nasal, pulmonary, and with or on an implantable medical device (e.g., stent or drug-eluting stent or balloon equivalents).

The effective dosage of each agent can readily be determined by a skilled person, having regard to typical factors such as the age, weight, sex and clinical history of the patient. A typical dosage could be, for example, 1-1,000 mg/kg, preferably 5-500 mg/kg per day, or less than about 5 mg/kg, for example administered once per day, every other day, every few days, once a week, once every two weeks, or once a month, or a limited number of times, such as just once, twice or three or more times.

A pharmaceutical composition containing each active ingredient may be in a form suitable for oral use, for example, as tablets, troches, lozenges, fast-melts, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from sweetening agents, flavoring agents, coloring agents and preserving agents, in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration in the stomach and absorption lower down in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,166,452 and 4,265,874, to form osmotic therapeutic tablets for control release. Preparation and administration of compounds is discussed in U.S. Pat. No. 6,214,841 and U.S. Pub. 2003/0232877, incorporate by reference herein in their entirety.

Formulations for oral use may also be presented as hard gelatin capsules in which the active ingredient is mixed with an inert solid diluent, for example calcium carbonate, calcium phosphate or kaolin, or as soft gelatin capsules in which the active ingredient is mixed with water or an oil medium, for example peanut oil, liquid paraffin or olive oil.

An alternative oral formulation, where control of gastrointestinal tract hydrolysis of the compound is sought, can be achieved using a controlled-release formulation, where a compound of the invention is encapsulated in an enteric coating.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents such as a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be in a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Each active agent, including the inventive compound, may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Examples of such materials are cocoa butter and polyethylene glycols.

For topical use, creams, ointments, jellies, fast melt tablets, solutions or suspensions are suitable as are nebulized forms for pulmonary delivery. Topical application includes the use of mouth washes and gargles.

The invention further also generally relates to devices such as implantable medical devices including an antithrombotic compound. In certain aspects, the invention provides a stent (e.g., a drug-eluting stent) or balloon comprising a compound of the invention or a compound of the invention along with other complementary drugs such as sirolimus, paclitaxel, tPA, urokinase etc. A device of the invention may be a drug-eluting aortic valve prosthesis or a drug-eluting mitral valve prosthesis. Accordingly, the invention provides administration of a compound of the invention via delivery from a stent, aortic valve, or mitral valve. In some embodiments, the invention provides a drug-eluting aortic valve or drug-eluting mitral valve.

In certain embodiments, the invention provides an implantable medical device or balloon comprising a compound of the invention for use in percutaneous cardiovascular intervention (PCI). A device of the invention can be a stent or a balloon. The invention also provides methods of using devices comprising antithrombotic compounds. Devices and methods of the invention can provide a TP antagonist compound in a stent (e.g., DES), balloon, implantable device, or surgical device or a compound of the invention along with other complementary drugs such as tPA, urokinase etc. Devices and antithrombotic compounds are discussed in U.S. Pat. Nos. 7,947,302; 7,618,949; and U.S. Pub. 2006/0122143, the contents of which are hereby incorporated by reference in their entirety.

A stent according to the invention can comprise a mesh tube-like structure, for example, to be used in conjunction with angioplasty to permanently hold open an artery at the narrowed site in the blood vessel, allowing for unrestricted blood flow, or to support a weakness or "aneurysm" in the blood vessel artery wall. Stents are discussed in U.S. Pat. Nos. 6,796,998; 6,352,552; U.S. Pub. 2005/0015136; U.S. Pub. 2005/0010279; and U.S. Pub. 2007/0168015, the contents of each of which are herein incorporated by reference in their entirety.

Compounds of the invention may provide coating agents for stents, drug-eluting stents (DESs), bifurcation stents, by-pass graft vessel stents, balloons, medical devices, or surgical devices used, for example, to treat stroke or other thrombotic events. By antagonizing the TP receptor on platelets and macrophages, these compounds will prevent platelet aggregation and secretion at sites of local vessel damage and counteract the inflammatory effects of elevated levels of $TXA_2$ at sites of local vessel damage. By antagonizing the TP on smooth muscle cells (SMCs), the compounds will prevent $TXA_2$-induced SMC proliferation, neo-intima thickening and restenosis. Furthermore, as the TP also mediates the adverse actions of the isoprostane 8-iso-prostaglandin $(PG)F_{2\alpha}$, generated in abundance from arachidonic acid non-enzymatically from free radicals in situations of oxidative stress/injury, including in ischemia, compounds of the invention may also inhibit the undesirable actions of 8-iso-$PGF_{2\alpha}$ within the damaged blood vessel. The combination of these compounds with very low levels of sirolimus and/or paclitaxel may be synergistic in further preventing restenosis while at the same time in eliminating or reducing the adverse effects associated with local, high levels of sirolimus or paxlitaxol. The combination of these compounds along with clot lysing drugs such as tPA, urokinase or related type of drug can both lyse clots at sites of occlusion and prevent new thrombus formation, such as in the treatment of atherothrombosis, ischemic or cerebral stroke etc. DESs are discussed in U.S. Pat. Nos. 7,135,038; 5,697,967; U.S. Pub. 2011/0099785; U.S. Pub. 2010/0023115; and U.S. Pub. 2005/0043788, the contents of each of which is herein incorporated by reference in their entirety. Coating of stents is discussed in U.S. Pat. No. 7,833,544 and U.S. Pub. 2009/0062904, the contents of which are herein incorporated by reference in their entirety.

In certain embodiments, the invention provides TP antagonists with novel applications as a coating or a component of a device either used alone or in combination with very low levels of sirolimus and/or paxlitaxol. The release profile and timing of the release profile of both the compound of the invention along with either sirolimus and/or paxlitaxol can be optimized to maximize the anti-thrombotic and anti-restenosis effects. This can result in the prevention of signaling by the elevated levels of $TXA_2$, and of the isoprostane 8-iso-$PGF_{2\alpha}$, found in vicinity of damaged blood vessels post angioplasty and stenting. Prevention of this signaling prevents or reduces the impairment of the host immune response which arise due to elevated levels of $TXA_2$, and the isoprostane 8-iso-$PGF_{2\alpha}$, in the vicinity of damaged blood vessels post angioplasty and stenting. Compounds of the invention may further prevent restenosis, for example, by antagonizing TP on smooth muscle cells. Compounds of the invention could also be coated onto aortic or mitral valves which are used in TAVI (trans-catheter aortic valve intervention) to treat aortic stenosis. Such coating with the compounds onto aortic or mitral valves may prevent thrombus or stroke occurrence after TAVI surgery.

The invention provide compounds which can be used as a coating on bare metal stents, interwoven stents, drug-eluting stents and balloons, bifurcation stents and by-pass graft stents, namely for use as: (a) an anti-restenosis agent, (b) an anti-thrombotic agent and (c) a pro re-endothelialization agent. Compounds of the invention would be released from such coated medical devices used in the treatment of various diseases of the vasculature including coronary arterial disease (CAD) and peripheral arterial disease (PAD) in a pre-defined manner including zero order release, first order release and/or a combination of initial burst release followed by controlled release over a defined time period (e.g., 12 months). Compounds of the invention may be particularly beneficial in Aspirin resistant patients (~30% of the general population) who are even more vulnerable to acute coronary stent thrombosis and who develop elevated levels of prostanoids such as $TXA_2$ post stenting (Ruef & Kranzhofer, 2006, J Inter. Cardiol. Vol 19, pages 507-509). Other applications of the new small molecule drug as a coating on medical devices include applications on (a) bifurcation stents or by-pass graft lesion stents, (b) clot dissolvers on medical devices used to treat stroke and further prevention of clot formation on medical devices for neurological applications, (c) as well as a coating on inferior vena cava filters (IVCFs) used to treat severe deep vein thrombosis (DVT) or pulmonary embolism (PE) in various types of patients including those subject to various surgical interventions such as bariatric surgery, orthopedic surgery, trauma patients and diabetic patients undergoing surgical intervention. Drug delivery from devices is discussed in U.S. Pat. No. 7,713,538; U.S. Pub. 2004/0213818 and U.S. Pub. 2009/0311299, incorporated by reference herein in their entirety.

Compounds of the invention as TP antagonists should act as therapeutic drugs for pulmonary arterial hypertension (PAH), not only inhibiting the excessive vasoconstriction but also preventing the micro-thrombosis and, potentially, limit the pulmonary artery remodeling, right ventricular (RV) hypertrophy, endothelial cell dysfunction and local inflammation found in PAH. Compounds of the invention may also directly suppress inflammation or proliferation pathways implicated in PAH. Added to this, as the TP also mediates the actions of 8-iso-$PGF_{2\alpha}$, a free-radical derived isoprostane generated in abundance in the clinical setting of PAH, as well as in other diseases involving oxidative stress or injury and which mediates similar actions to $TXA_2$, compounds of the invention will also antagonize these effects in PAH. In addition, as $TXA_2$ is a potent pro-inflammatory and mitogenic agent promoting vascular remodeling, restenosis and/or hypertrophy and is the main cyclo-oxygenase (COX)-derived constrictor prostanoid within the lung, compounds of the invention will antagonize these effects.

Hence, compounds of the invention would have added advantage over other PAH therapeutic agents used in that such compounds would not only inhibit $TXA_2$, the main vaso-constricting prostaglandin produced in the lung but also inhibit the adverse actions of the oxidative-stress derived isoprostane 8-iso-PGF2α, in addition to those of $TXA_2$ itself, its endoperoxide precursor $PGG_2/PGH_2$ and 20-HETE, for example. Besides PAH, in other diseases such as atherothrombosis replacing the standard-of-care Aspirin with compounds of the invention will offer several advantages as they will: (i) not only block the action of TXA$_2$ but also of Aspirin-insensitive TP agonists (e.g., 8-iso-PGF$_{2\alpha}$, generated in abundance by free-radicals during oxidative injury); (ii) also (unlike Aspirin), will inhibit the TP expressed in cells of the vascular bed and in circulating macrophages/monocytes, present during the inflammatory atherothrombosis; (iii) overcome Aspirin-resistance, estimated to occur in ~33% of the population.

As various compounds of the invention do not require liver metabolism to achieve an active therapeutic form, they provide the benefit of immediate therapeutic effect within the vasculature at the site of release or immediate local environment of the coated medical device. This drug coating on medical devices has applications as prophylaxis and/or as therapeutic treatment.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

The invention provides for the synthesis and biological evaluation of a range of compounds (new chemical entities, referred to as NTP42-NTP49) that act as antagonists of the TPα and/or TPβ (iso)forms of the human thromboxane (TX) A2 receptor, also referred to as the T prostanoid receptor or, in short, the TP. These TP antagonists will inhibit the actions (antagonize) of thromboxane (TX)A$_2$, and of the free radical derived isoprostane 8-iso-prostaglandin (PG)F$_2$, and of all other incidental agents (e.g the endoperoxide PGG$_2$/PGH$_2$ and 20-HETE) that activate (act as agonists or as partial agonists) of the TP. The TP is expressed in a range of cell types throughout the body and the compounds (TP antagonists) described herein target the TPs (including TPα and/or TPβ) expressed in all of those cell types. In addition, altered expression of the TPs occurs in a range of disease settings and the compounds (TP antagonists) described herein target the TPs (including TPα and/or TPβ) expressed in all of those cell types and in different disease settings including in inflammation and in cancer. Furthermore, the compounds can be used in any drug format (such as, but not limited to oral, i.v, i.p, dermal, transdermal delivery systems or on medical devices, such as stents of on drug eluting stents). Reference is made to compounds with formulas NTP4 and TP20, and also see Table 5, at the end.

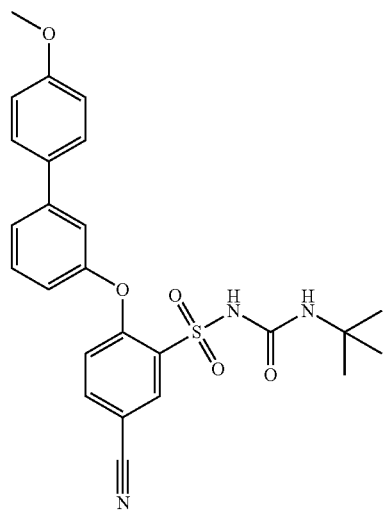

(NTP4)

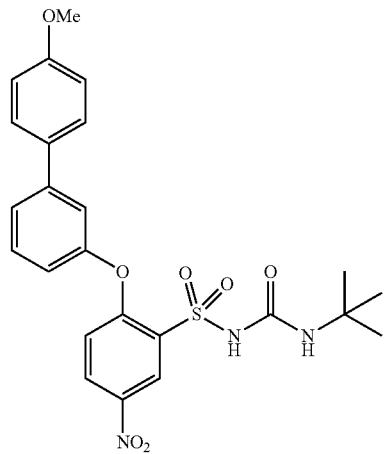

(TP20)

Here, we have successfully increased the efficacy of NTP4 by replacing a Methoxy group with difluoromethoxy (in NTP42), trifluoromethoxy (in NTP43), difluoro (NTP44), trifluoro (NTP45), secondary amide (—C(=O)NHMe; NTP47), tertiary amide (—C(=O)N(Me)2; NTP48) or nitrile (NTP49) group, from which we identified three new, highly potent, efficacious and desirable leads, NTP42, NTP43 & NTP48. These examples illustrate compounds that have been synthesized and screened for biological activity (e.g., NTP42-NTP49), where compounds NTP4 & TP20 served as reference or control compounds. We have carried out additional, highly focused medicinal chemistry to further improve the efficacy of NTP4 while retaining its specificity as a selective TP antagonist. Specificity of the lead compounds as TP-specific antagonists has been confirmed through their ability to inhibit agonist-induced intracellular calcium mobilization and in efficacy assays through their ability to inhibit platelet aggregation in ex vivo assays. More specifically, the results established that, like TP20 and NTP4, neither NTP42, NTP43 nor NTP48 exhibited any effect on signaling through other prostanoid (prostaglandin (PG) D$_2$ receptor, DP; PGE$_2$ receptors EP1, EP2, EP3 and EP4; PGF$_{2\alpha}$ receptor, FP; PGI$_2$/prostacyclin receptor, IP) and non-prostanoid receptors including the purinergic (ADP) and thrombin (PAR1) receptors, also involved in platelet activation similar to the TP isoforms. NTP42, NTP43 and NTP48, have each been confirmed not to exhibit any effect on DP-, EP1-EP4-, FP- or IP-mediated signaling. The data have confirmed that NTP42, and NTP43 and NTP48 exhibit minimal toxicity and favorable cell permeability.

We have developed a novel series of highly specific TP (TPα- and TPβ-selective) antagonists NTP42-NTP49 that have been subject to biological evaluation. Formula III shows a generic structures of the NTP42-NTP49 compounds, where R1 may be either a difluoromethoxy (in NTP42), trifluoromethoxy (in NTP43), difluoro (in NTP44), trifluoro (in NTP45), secondary amide (—C(═O)NHMe; in NTP47), tertiary amide (—C(═O)N(Me)2; in NTP48) or by a nitrile (in NTP49) groups to generate seven new, highly potent, efficacious and desirable leads.

In addition to the primary application of TP antagonists for the treatment of various CV diseases, there are numerous other disease indications, including diseases with orphan disease designations, for use or commercial development of our TP antagonist technology. For example: these TP antagonists will inhibit the actions of thromboxane (TX)$A_2$ and of the free-radical derived isoprostane 8-iso-prostaglandin (PG) $F_{2\alpha}$ and of all other incidental agents (e.g the endoperoxide $PGG_2/PGH_2$, 20-HETE) that activate (act as agonists or as partial agonists) of the TP. As stated, the TP is expressed in a range of cell types throughout the body and the compounds (TP antagonists) described herein target the TPs (including TPα and/or TPβ) expressed in all of those cell types. In addition, altered expression of the TPs occurs in a range of disease settings and the compounds (TP antagonists) described herein target the TPs (including TPα and/or TPβ) expressed in all of those cell types and in different disease settings including in inflammation and in cancer. Furthermore, the compounds can be used in any drug format (such as, but not limited to oral, i.v, i.p, dermal, transdermal delivery systems or on medical devices, such as stents of on drug eluting stents).

Example 1: Assessment of NTP42-NTP49

NTP42-NTP49, northern group variants of NTP4, were assessed through calcium mobilization assays using proprietary HEK 293 cells over-expressing the thromboxane (TX) $A_2$ receptor, α (TPα) and β (TPβ) isoforms, referred to as HEK.TPα and HEK.TPβ cells, respectively. The initial screening involved dose-responses assays (concentrations used 0.0001 (TPβ only), 0.001, 0.1, 1 & 10 μM; (TPα and TPβ)) followed by more focused, full dose response assays (concentration range: 0.00001 to 10 μM) for determination of $IC_{50}$ values where the effect of the compounds on calcium mobilized in response to the $TXA_2$ mimetic U46619 (1 μM) were performed in side-by-side comparison with the key lead compounds TP20 and NTP4. The results are shown in FIGS. 1-4 and Table 1 (n>4).

Conclusions:

(A) Initial Testing: Calcium Mobilization Assays: The new compounds NTP42-NTP49, potently inhibit TPα and TPβ-mediated calcium mobilization, where NTP42 and NTP48 exhibit greater potency than TP20, as determined in dose-response calcium mobilization assays. See FIGS. 1 to 4, and Table 1 for further details. The rank order of potency in the 2 cells lines is indicated below:

TPα: NTP48>NTP42>NTP43>TP20>>NTP4
TPβ: NTP48>NTP42>TP20>NTP43>NTP4

(B) Ex Vivo Platelet Aggregation Assays: In preliminary platelet aggregation assays, performed using the PAP-8E platelet aggregometer, NTP42, NTP43 & NTP48 have demonstrated potency in inhibiting U46619-mediated platelet aggregation, where the rank order is:

Platelets: NTP48>NTP42>TP20>NTP43>NTP4
See FIGS. 5 and 6, and Table 2 for further details.

(C) Specificity (see FIGS. 7, 8 and 11-17 for further details): In preliminary assays to determine specificity of the new compounds, NTP42-NTP49 have exhibited no effect on IP/cicaprost or $EP/PGE_2$-mediated calcium mobilization. Specifically, NTP42-NTP49 were found to have no effect on hIP/cicaprost- or $EP/PGE_2$-mediated calcium responses. To date, with the exception of NTP46, compounds NTP44-NTP49 have been tested for their effect on signaling by the $PGI_2$ receptor, IP and the $PGE_2$ receptors/EPs and, like TP20 and NTP4, the new compounds NTP42, NTP43 and NTP48 have been confirmed to exhibit no effect on IP-, EP-mediated signaling. The data have confirmed that the new lead compounds NTP42, NTP43 and NTP48 exhibit minimal toxicity and favorable cell permeability.

In addition, further specificity testing established that neither NTP42 nor NTP48 exhibited any effect on signaling through other prostanoid receptors (prostaglandin (PG) $D_2$ receptor, DP; $PGE_2$ receptors EP1, EP2, EP3 and EP4; $PGF_{2\alpha}$ receptor, FP; $PGI_2$/prostacyclin receptor, IP) and non-prostanoid receptors including the purinergic (ADP) and thrombin (PAR1) receptors, also involved in platelet activation similar to the TP isoforms. NTP42, NTP43 and NTP48, have each been confirmed not to exhibit any effect on DP-, EP1-EP4-, FP- or IP-mediated signaling. The data have confirmed that NTP42, and NTP43 and NTP48 exhibit minimal toxicity and favorable cell permeability.

(A) Initial Testing: Effect of NTP42-NTP49 on U46619-Mediated Calcium Mobilization As stated, NTP42-NTP49 were screened through calcium mobilization assays using HEK.TPα and HEK.TPβ cells over-expressing the thromboxane (TX)$A_2$ receptor, α (TPα) and β (TPβ) isoforms, respectively. The initial screening involved dose-response assays where the compounds, used at 0.0001 (TPβ only), 0.001, 0.1, 1 & 10 μM (TPα and TPβ), were assessed for their ability to inhibit the TXA2 mimetic U46619 (1 μM). The compounds were tested in side-by-side assays with the previously identified key lead compounds TP20 and NTP4. The results are shown below.

FIG. 1 shows the effect of the TP antagonists on U46619-mediated calcium mobilization in HEK TPα cells (Isolate HR #4). HEK.TPα (HR #4) cells, preloaded with Fluo-4, were incubated with the TP20, NTP4, NTP42, NTP43, NTP44, NTP45, NTP47, NTP48 & NTP49 where each antagonist was used at 0.001, 0.1, 1 & to 10 μM, as indicated, prior to stimulation with 1 μM U46619. Data is presented as the mean (±S.E.M.) percentage of the agonist-induced response in vehicle-treated cells (Percentage of Control; %) and represents data from at least 4 independent experiments were cells were treated in duplicate.

Figure 2:
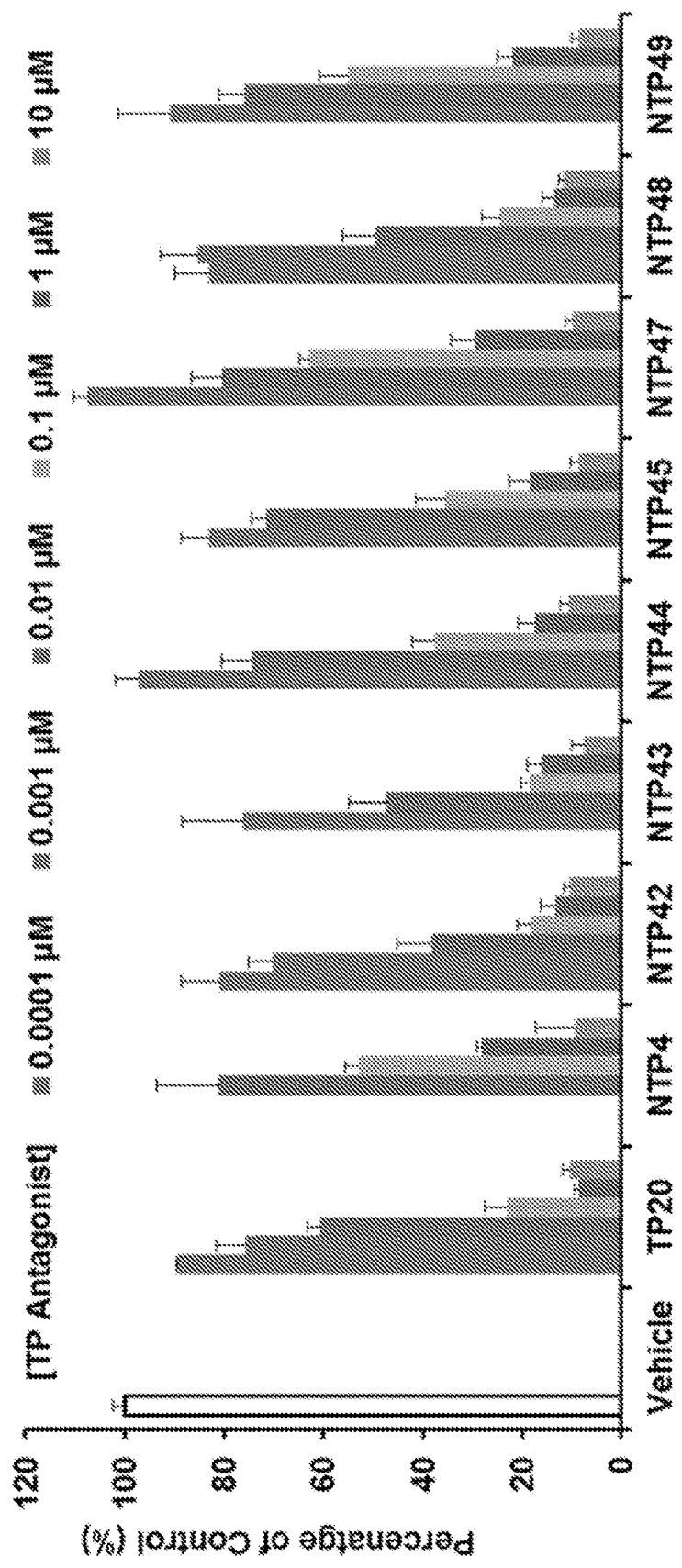
FIG. 2 shows the effect of compounds of the invention on U46619-mediated calcium mobilization in HEK TPβ cells.

FIG. 2 shows the effect of the TP antagonists on U46619-mediated calcium mobilization in HEK TPβ cells. HEK.TPβ (EM #8) cells, preloaded with Fluo-4, were incubated with the TP20, NTP4, NTP42, NTP43, NTP44, NTP45, NTP47, NTP48 & NTP49 where each antagonist was used at 0.0001, 0.001, 0.1, 1 & to 10 μM, as indicated, prior to stimulation with 1 μM U46619. Data is presented as the mean (±S.E.M.) percentage of the agonist-induced response in vehicle-treated cells (Percentage of Control; %) and represents data from at least 4 independent experiments were cells were treated in duplicate.

Comments:

Consistent with previous data, the reference compounds/leads TP20 and NTP4 inhibit the U46619-mediated calcium mobilization in HEK.TPα and HEK.TPβ cells. Likewise the new northern group variants (NTP42-NTP49) inhibit U46619-mediated responses in both cell lines albeit to varying degrees. Furthermore, in most cases the level of inhibition is greater than that observed for NTP4. From the above data the most active new compounds include NTP42, NTP43 & NTP48. These compounds were subject to further examination through full-dose response assays to determine IC 50 values for inhibition.

Figure 3:
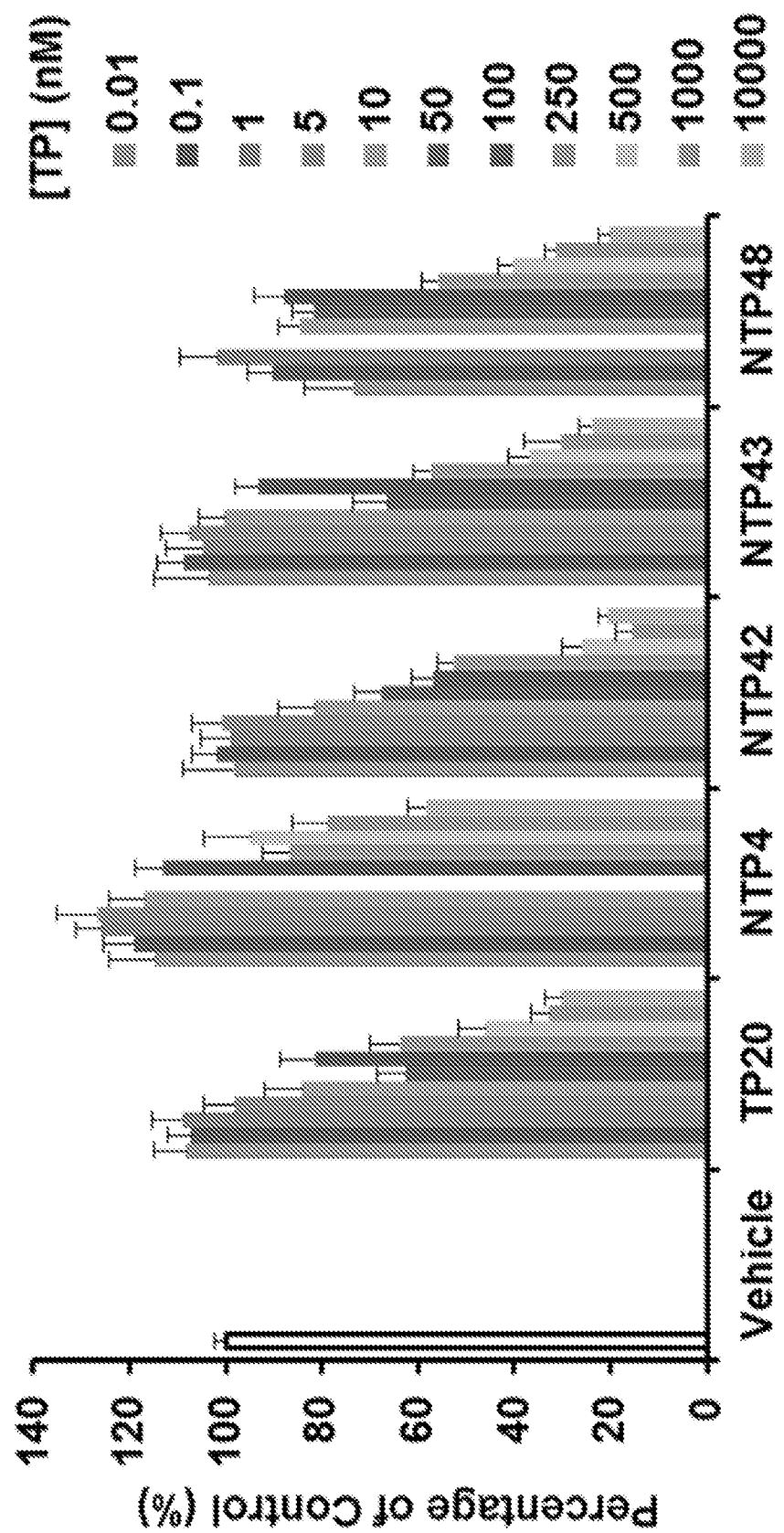
FIG. 3 shows the effect of compounds of the invention on U46619-mediated calcium mobilization in HEK TPα cells.

FIG. 3 shows the effect of the TP antagonists on U46619-mediated calcium mobilization in HEK TPα cells (Isolate HR #4).

HEK.TPα (HR #4) cells, preloaded with Fluo-4, were incubated with the TP20, NTP4, NTP42, NTP43 and NTP48 where each antagonist was used at 0.00001-10 µM, as indicated, prior to stimulation with 1 µM U46619. Data is presented as the mean (±S.E.M.) percentage of the agonist induced response in vehicle-treated cells (Percentage of Control; %) and represents data from at least 3 independent experiments were cells were treated in duplicate.

Figure 4:
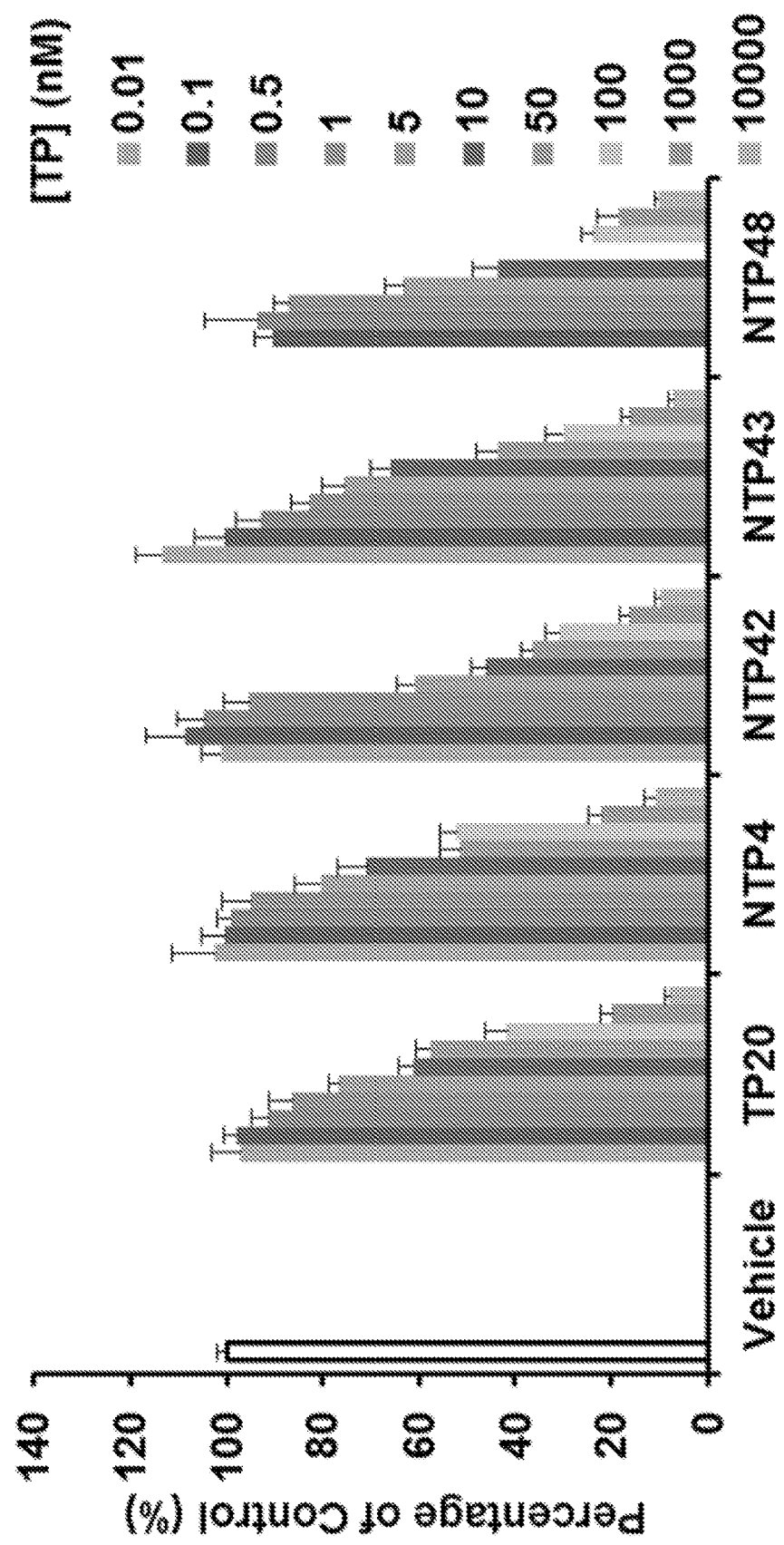
FIG. 4 shows the effect of compounds of the invention on U46619-mediated calcium mobilization in HEK TPβ cells.

FIG. 4 shows the effect of the TP antagonists on U46619-mediated calcium mobilization in HEK TPβ cells. HEK.TPβ (EM #8) cells, preloaded with Fluo-4, were incubated with the TP20, NTP4, NTP42, NTP43 and NTP48 where each antagonist was used at 0.00001-10 µM, as indicated, prior to stimulation with 1 µM U46619. Data is presented as the mean (±S.E.M.) percentage of the agonist-induced response in vehicle-treated cells (Percentage of Control; %) and represents data from at least 4 independent experiments were cells were treated in duplicate.

TABLE 1

Estimated $IC_{50}$ values for inhibition of U46619-mediated [Ca 2+ ]i mobilization in HEK.TPα and HEK.TPβ cells.

| TP Antagonist | $IC_{50}$ values for Inhibition of U46619-Mediated $[Ca^{2+}]i$ Mobilisation (nM) | |
| --- | --- | --- |
|  | TPα | TPβ |
| TP20 | 125 ± 11.4 (n = 5) | 9.61 ± 1.46 (n = 6) |
| NTP4 | 593 ± 83.6 (n = 5) | 60.4 ± 8.00 (n = 6) |
| NTP42 | 56.2 ± 4.84 (n = 6) | 8.25 ± 0.73 (n = 10) |
| NTP43 | 105 ± 7.95 (n = 6) | 18.4 ± 1.63 (n = 9) |
| NTP48 | 90.1 ± 6.43 (n = 4) | 5.06 ± 1.50 (n = 6) |

Comment:

From previous SAR studies, TP20 and NTP4 were identified as key lead compounds. Consistent with this, both TP20 and NTP4 potently inhibited U46619-mediated calcium mobilization in HEK.TPα and HEK.TPβ cells, where $IC_{50}$ values for inhibition of TPβ-mediated responses were determined to be in the nanomolar range (see Table 1 for specific figures for each compound in each cell line). Similarly, the compounds NTP42-NTP49 potently inhibited U46619-mediated responses in both cell lines. In particular, compounds NTP42, NTP43 and NTP48 were the most effective and were selected for more detailed analysis and determination of $IC_{50}$ values. The $IC_{50}$ values indicate that NTP42, NTP43 and NTP48 are more effective at antagonizing TPα and TPβ responses than NTP4, i.e., replacement of the methoxy group with a di-, tri-fluoromethoxy or a tertiary amide has improved efficacy. The three compounds, NTP42, NTP43 and NTP48, were subject to further characterization through both calcium and platelet aggregation assays.

(B) Effect of NTP42 to NTP49 on U46619-Mediated Platelet Aggregation:

In order to evaluate NTP42-NTP49 in a second independent assay, the effect of the compounds on U46619-mediated platelet aggregation assays was examined. Clearly, from an efficacy point of view, this is an important assay and, physiologically, the more relevant with respect to the therapeutic target.

The initial screening involved dose-response assays where the compounds, used at 7.8125, 15.625, 31.25, 62.5 & 125 nM, were assessed for their ability to inhibit the platelet aggregation induced by the TXA 2 mimetic U46619 (1 µM). The compounds were tested in side-by-side assays with the previously identified key lead compound TP20 using the PAP-8E platelet aggregometer. The results are shown below.

Figure 5:
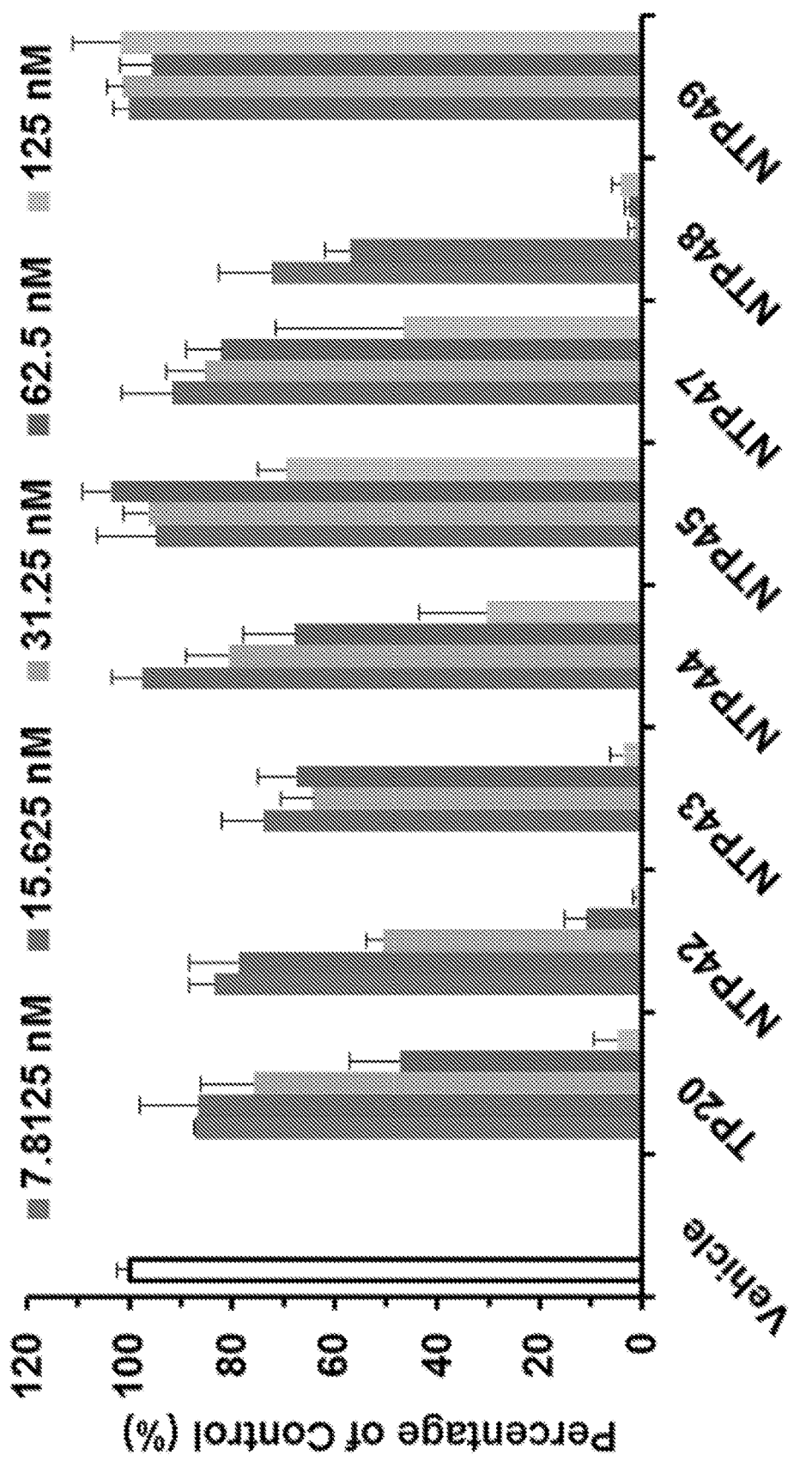
FIG. 5 shows the effect of compounds of the invention on U46619-mediated platelet aggregation.

FIG. 5 shows the effect of NTP42 to NTP49 on U46619-mediated platelet aggregation. PRP was prepared from blood taken from healthy volunteers into syringes containing 3.8% sodium citrate and 10 µM indomethacin such that the final ratio of anticoagulant to blood was 1:9. Aliquots of PRP (300 µl) were pre-incubated for 10 min with the TP antagonists, TP20, NTP42, NTP43, NTP44, NTP45, NTP47, NTP48 and NTP49, where 2-fold serial dilutions from 0.25 µM was prepared for each, prior to stimulating platelets with 1 µM U46619, incubated at 37° C., with stirring. The results are presented as Percentage Aggregation (mean±S.E.M.), as determined by changes in light transmission over time using the PAP-8E Platelet Aggregation Profiler and represents data from 4 independent experiments (n=4).

Comments:

Like the reference compound TP20, the new NTP42-NTP49 chemical entities potently inhibit U46619-mediated aggregation of human platelet ex vivo, where NTP42, NTP43 & NTP48 are the most efficacious. Hence, in subsequent assays, the effect of NTP42, NTP43 & NTP48 and, as reference compounds TP20 & NTP4, on U46619-mediated platelet aggregation in side-by-side comparisons was performed using the PAP-8E platelet aggregometer.

Figure 6:
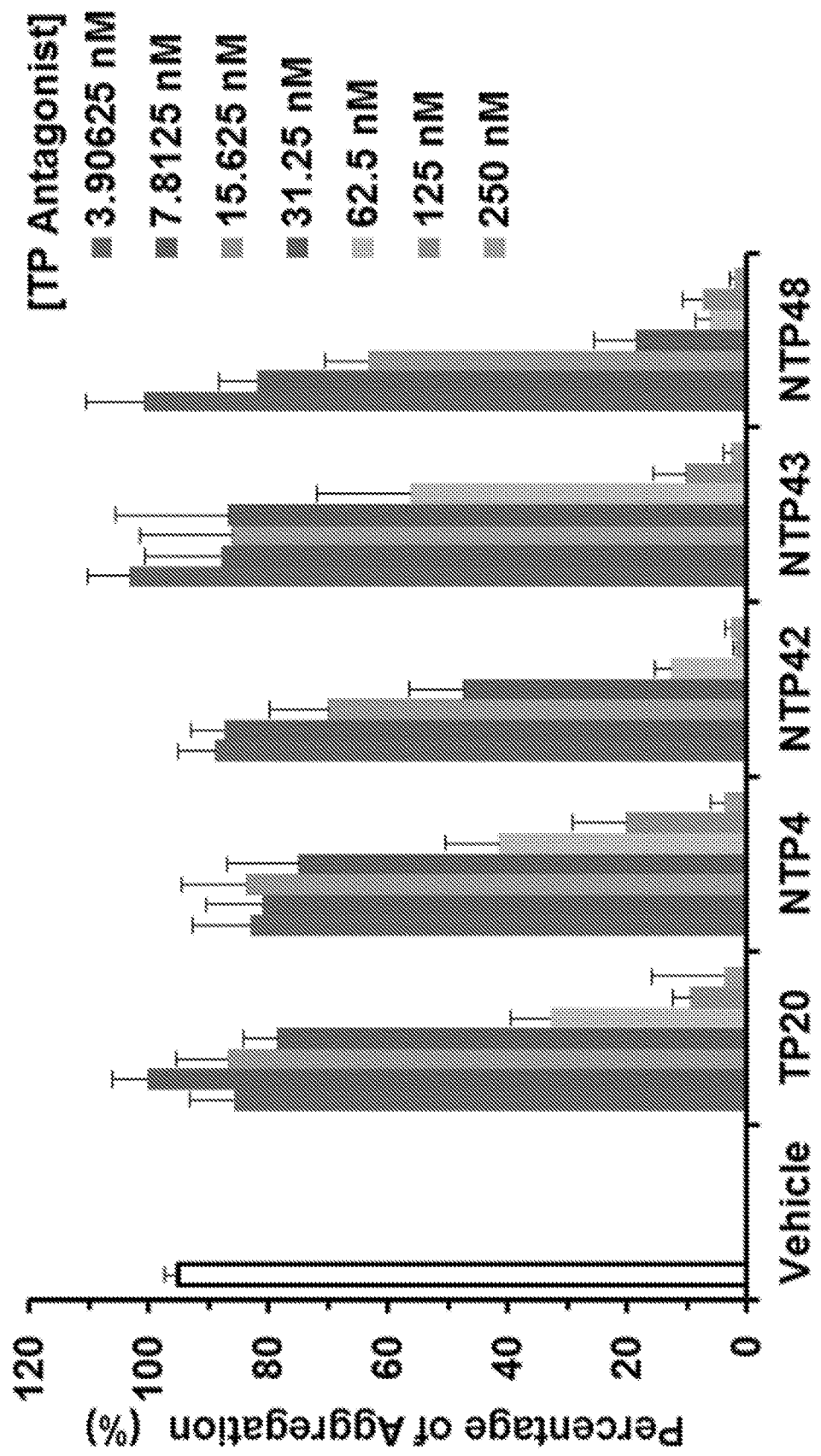
FIG. 6 shows the effect of compounds of the invention on U46619-mediated platelet aggregation.

FIG. 6 shows the effect of NTP42, NTP43 & NTP48 on U46619-mediated platelet aggregation. PRP was prepared from blood taken from healthy volunteers into syringes containing 3.8% sodium citrate and 10 µM indomethacin such that the final ratio of anticoagulant to blood was 1:9. Aliquots of PRP (300 µl) were pre-incubated for 10 min with the TP antagonists, TP20, NTP4, NTP42, NTP43 and NTP48, where 2-fold serial dilutions from 1 µM was prepared for each, prior to stimulating platelets with 1 µM U46619, incubated at 37° C., with stirring. The results are presented as Percentage Aggregation (mean±S.E.M.), as determined by changes in light transmission over time using the PAP-8E Platelet Aggregation Profiler and represents data from at least 3 independent experiments (n≥3).

TABLE 2

Estimated $IC_{50}$ values for inhibition of U46619-mediated platelet aggregation.

| TP Antagonist | $IC_{50}$ values for Inhibition of U46619-Mediated Platelet Aggregation (nM) |
| --- | --- |
| TP20 | 4.62 ± 0.72 (n = 6) |
| NTP4 | 21.3 ± 1.01 (n = 6) |
| NTP42 | 10.1 ± 1.07 (n = 6) |
| NTP43 | 22.0 ± 2.03 (n = 6) |
| NTP48 | 9.45 ± 1.38 (n = 3) |

Comments:

Compounds NTP42, NTP43 and NTP48 inhibited U46619-mediated responses, where both NTP42 and NTP48 were more potent than either TP20 or NTP4. NTP43 exhibited equivalent potency as NTP4 to inhibit U46619-mediated responses.

(C) Specificity Testing: Effect of NTP42 to NTP49 on hIP-& EP3-Mediated Calcium Mobilization To confirm the specificity of the new NTP42 to NTP49 compounds, their effect on hIP (Cicaprost)- and EP (PGE$_2$)-mediated responses were examined in HEK.hIP and HEL 92.1.7 cells, respectively. Compounds were tested at 10 µM, where results are shown below.

Figure 7:
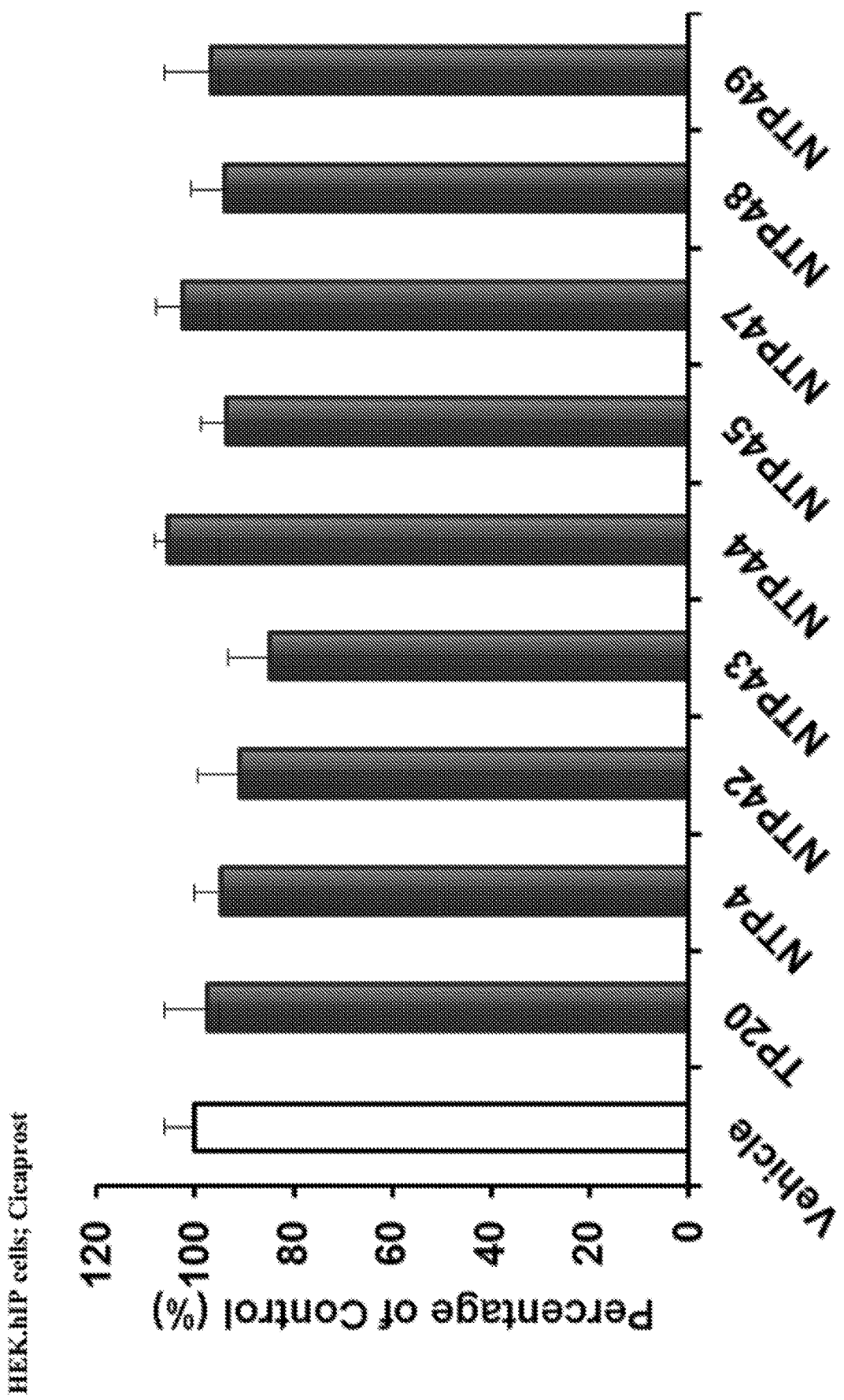
FIG. 7 shows the effect of compounds of the invention on Cicaprost-Mediated Calcium Mobilization in HEK.hIP cells.

FIG. 7 shows the effect of the TP antagonists on Cicaprost-Mediated Calcium Mobilization in HEK.hIP cells. HEK.hIP cells, preloaded with Fluo-4, were incubated with the TP20, NTP4, NTP42, NTP43, NTP45, NTP47, NTP48 and NTP49 where each antagonist was used at 10 µM, as indicated, prior to stimulation with 1 µM Cicaprost. Data is presented as the mean (±S.E.M.) percentage of the agonist-induced response in vehicle-treated cells (Percentage of Control; %) and represents data from at least 3 independent experiments were cells were treated in triplicate. HEK.hIP cells.

Figure 8:
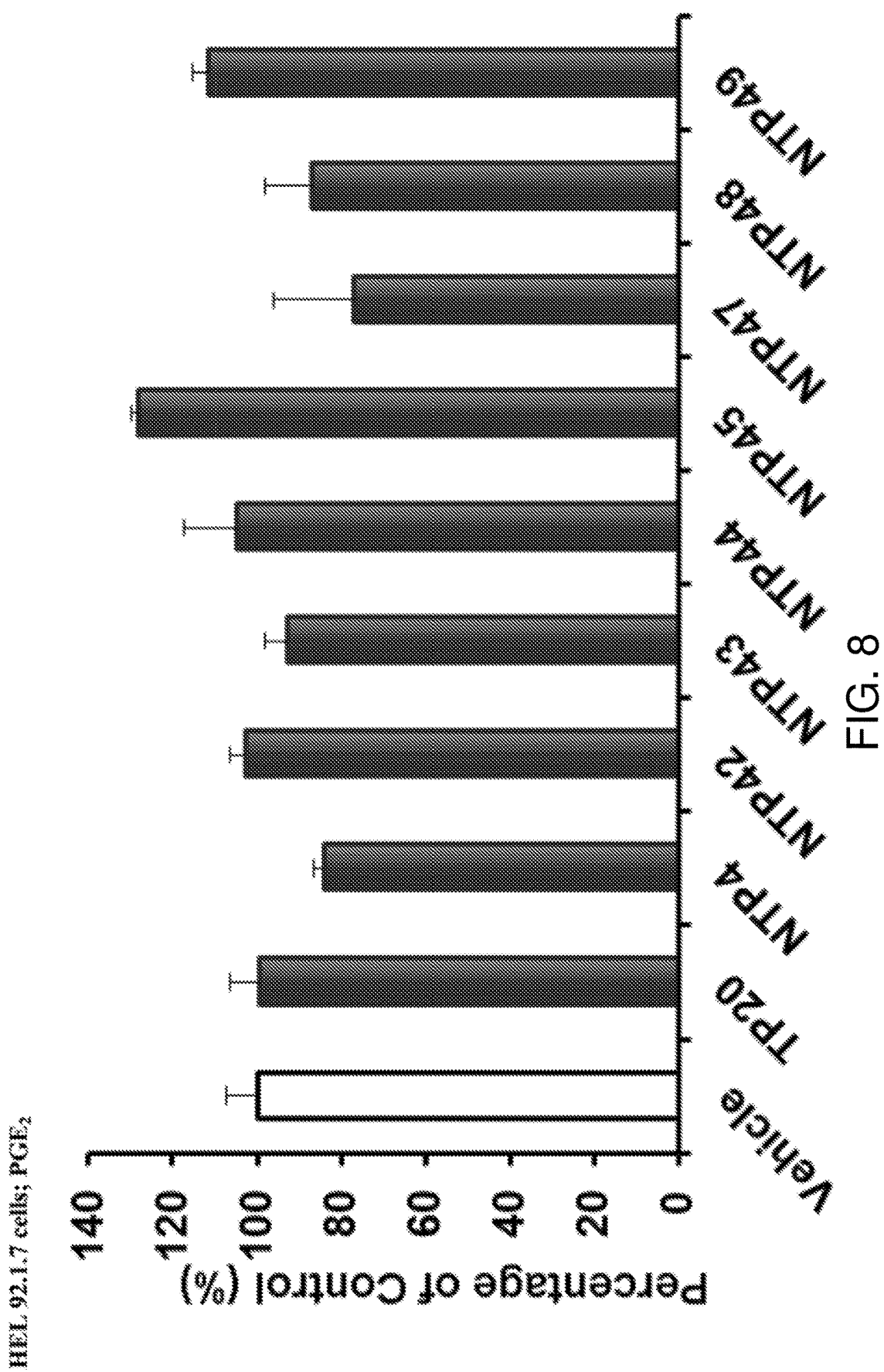
FIG. 8 shows the effect of compounds of the invention on EP3/PGE$_2$-Mediated Calcium Mobilization in HEL 92.1.7 cells.

FIG. 8 shows the effect of the TP antagonists on EP/PGE$_2$-Mediated Calcium Mobilization in HEL 92.1.7 cells. HEL 92.1.7 cells, preloaded with Fluo-4, were incubated with the TP20, NTP4, NTP42 and NTP43 where each antagonist was used at 10 µM, as indicated, prior to stimulation with 1 µM Cicaprost. Data is presented as the mean (±S.E.M.) percentage of the agonist induced response in vehicle-treated cells (Percentage of Control; %) and represents data from 3 independent experiments were cells were treated in triplicate. 1 µM PGE$_2$.

Comments: Herein, the data indicates that NTP42 to NTP49 have no issues with respect to specificity and have been demonstrated to be highly specific for antagonism of TP/U46619-mediated responses.

Example 2: (PG)F$_{2\alpha}$ Antagonism

Demonstration of the Ability of NTP42, NTP43 & NTP48 and, as a reference NTP4 and TP20, to Antagonize the Actions of the isoprostane 8-iso-Prostaglandin (PG)F$_{2\alpha}$.

Effect of NTP42-NTP48 on 8-iso-PGF2α-mediated Calcium Mobilization In addition, to assessment of the compounds to antagonise U46619-mediated responses, the ability of NTP42 & NTP43 to inhibit the partial TP agonist 8-iso-PGF$_{2\alpha}$ has been examined through calcium mobilization assays in HEK.TPα and HEK.TPβ cells.

Figure 9:
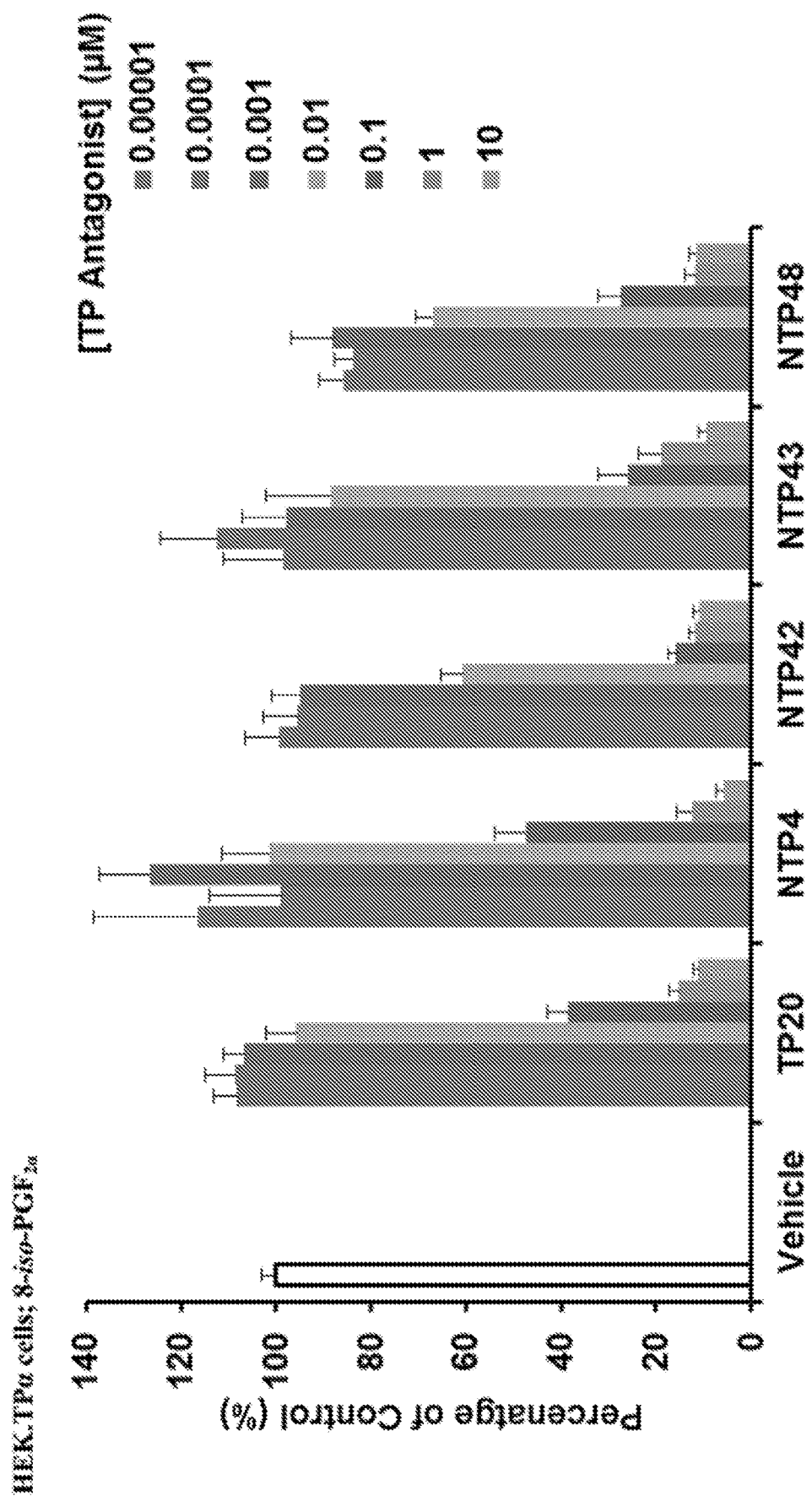
FIG. 9 shows the effect of compounds of the invention on 8-iso-PGF$_{2\alpha}$-mediated calcium mobilization in HEK TPα cells.
Figure 10:
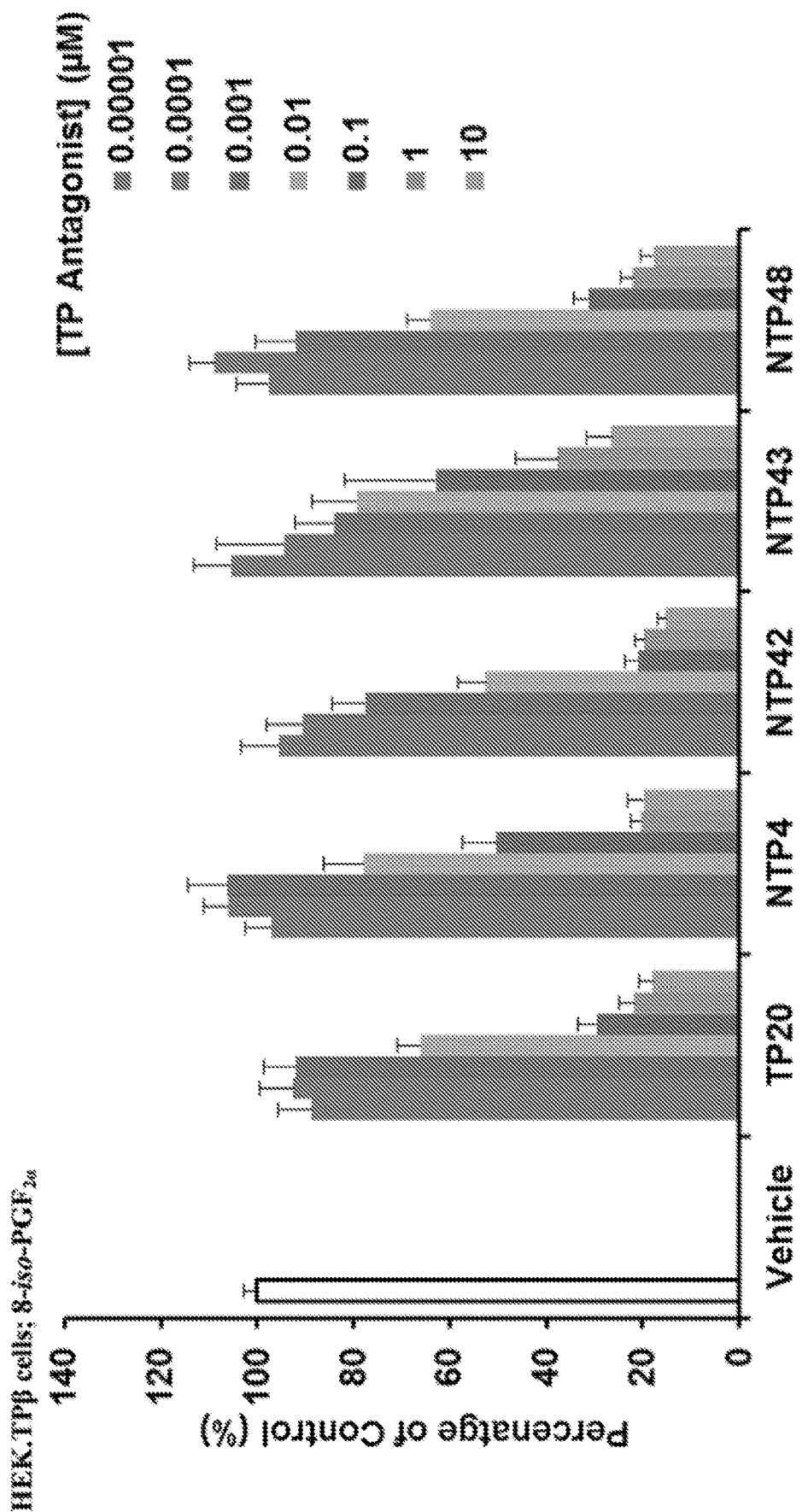
FIG. 10 shows the effect of compounds of the invention on 8-iso-PGF$_{2\alpha}$-mediated calcium mobilization in HEK TPβ cells.

FIGS. 9 and 10 show the effect of the TP antagonists on 8-iso-PGF$_{2\alpha}$-mediated calcium mobilization in HEK TPβ cells.

FIG. 9 shows results after HEK.TPα cells, preloaded with Fluo-4, were incubated with the TP20, NTP4, NTP42, NTP43 and NTP48 where each antagonist was used at 0.00001-10 µM, as indicated, prior to stimulation with 10 µM 8-iso-PGF$_{2\alpha}$.

FIG. 10 shows results after HEK.TPβ cells, preloaded with Fluo-4, were incubated with the TP20, NTP4, NTP42, NTP43 and NTP48 where each antagonist was used at 0.00001-10 µM, as indicated, prior to stimulation with 10 µM 8-iso-PGF$_{2\alpha}$. Data is presented as the mean (±S.E.M.) percentage of the agonist-induced response in vehicle-treated cells (Percentage of Control; %) and represents data from at least 3 independent experiments were cells were treated in duplicate, except NTP48.

Table 3 presents the estimated IC$_{50}$ values for inhibition of 8-iso-PGF$_{2\alpha}$-mediated calcium mobilization in HEK.TPα and HEK.TPβ cells, where the partial agonist in the absence of TP antagonist mediated 112±3.26 (n=12) and 96.1±2.52 (n=8) responses, respectively.

TABLE 3

Estimated IC$_{50}$ values for inhibition of 8-iso-PGF$_{2\alpha}$-mediated [Ca$^{2+}$]$_i$ mobilization in HEK.TPα and HEK.TPβ cells.

| TP Antagonist | IC$_{50}$ values for inhibition of 8-iso-PGF$_{2\alpha}$-mediated [Ca$^{2+}$]i mobilization (nM) | |
|---|---|---|
| | TPα | TPβ |
| TP20 | 46.4 ± 4.24 (n = 12) | 17.0 ± 2.12 (n = 8) |
| NTP4 | 103 ± 11.1 (n = 6) | 58.0 ± 6.31 (n = 6) |
| NTP42 | 12.8 ± 1.42 (n = 6) | 8.00 ± 1.00 (n = 6) |
| NTP43 | 30.7 ± 5.05 (n = 4) | 9.00 ± 1.60 (n = 3) |
| NTP48 | 29.3 ± 3.87 (n = 3) | 15.4 ± 2.16 (n = 4) |

Conclusion:

Data have confirmed that the new key lead compounds, namely NTP42, NTP43 & NTP48, are potent inhibitors of 8-iso-PGF$_{2\alpha}$-mediated calcium responses. Furthermore, the data (presented above) confirms that NTP42, NTP43 & NTP48 are more potent than TP20 and NTP4. The rank order for inhibition of 8-iso-PGF$_{2\alpha}$-mediated calcium mobilization by the TP antagonists in each cell line is as follows:

TPα: NTP42>NTP48>NTP43>TP20>NTP4
TPβ: NTP42>NTP43>NTP48>TP20>NTP4

Example 3: Specificity

FIGS. 11-17 are examples of further specificity testing and shows that neither NTP42 nor NTP48 exhibited any effect on signaling through the other prostanoid receptors (i.e the prostaglandin (PG) D$_2$ receptor, DP; PGE$_2$ receptors EP1, EP2, EP3 and EP4; PGF$_{2\alpha}$ receptor, FP; PGI$_2$/prostacyclin receptor, IP).

Figure 11:
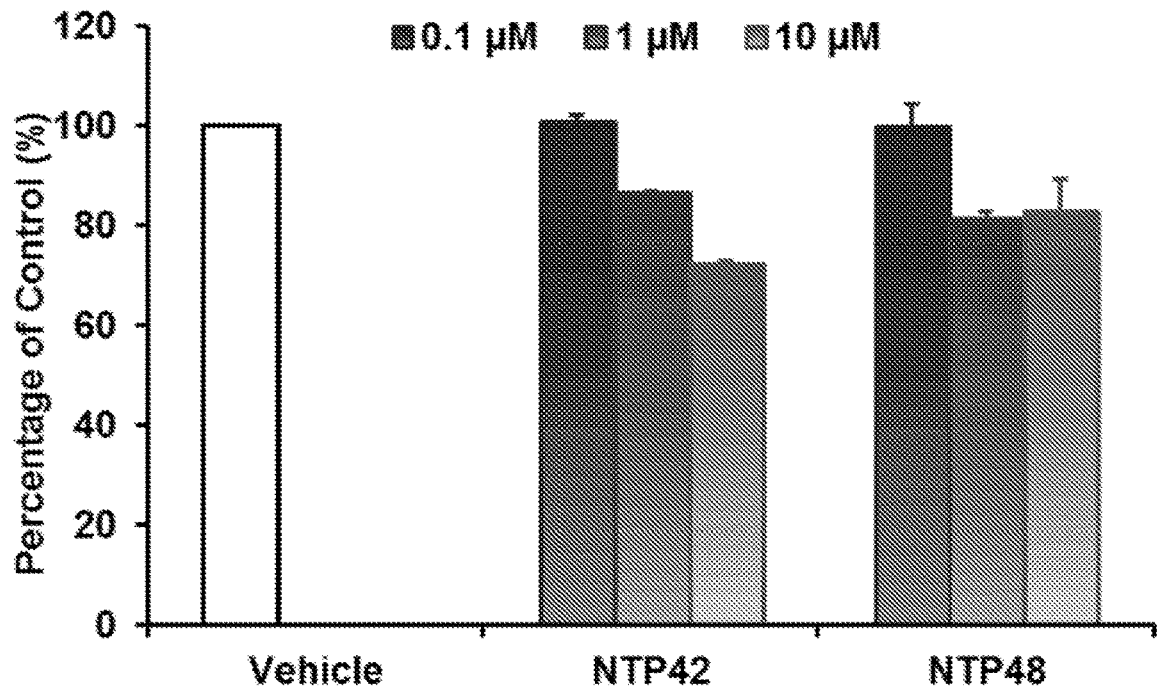
FIG. 11 shows that compounds of the invention exhibit no effect on the DP$_1$ receptor.

FIG. 11 shows that NTP42 and NTP48 exhibit no effect on the DP$_1$ receptor.

Figure 12:
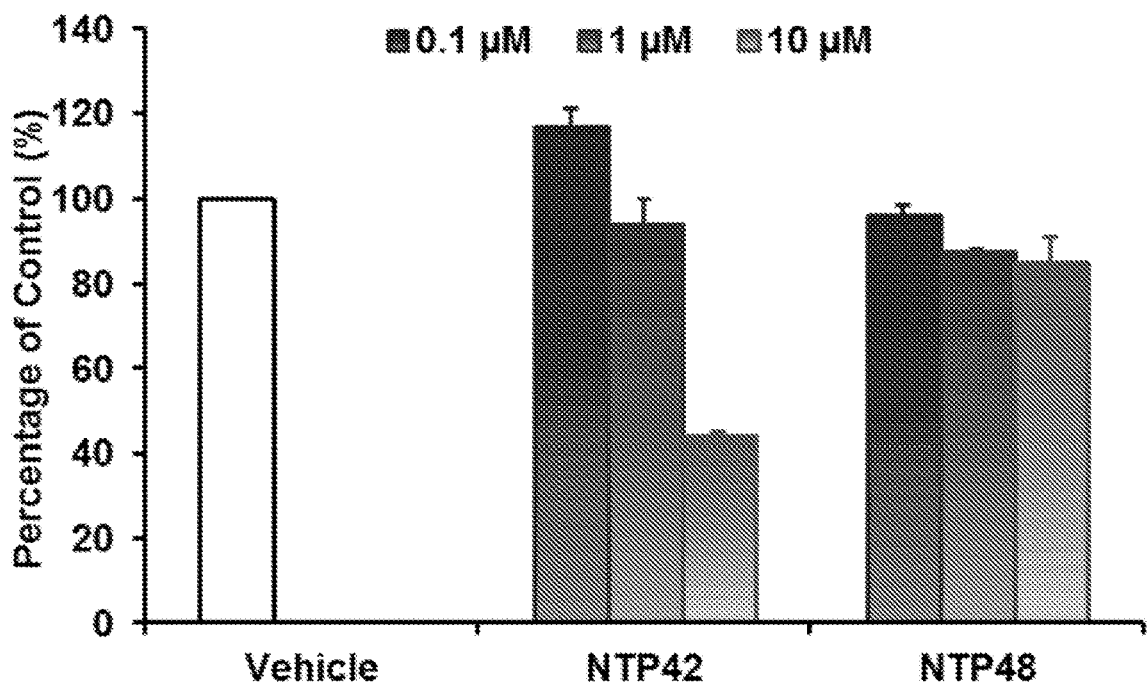
FIG. 12 shows that compounds of the invention exhibit no effect on the EP$_1$ receptor.

FIG. 12 shows that NTP42 and NTP48 exhibit no effect on the EP$_1$ receptor.

Figure 13:
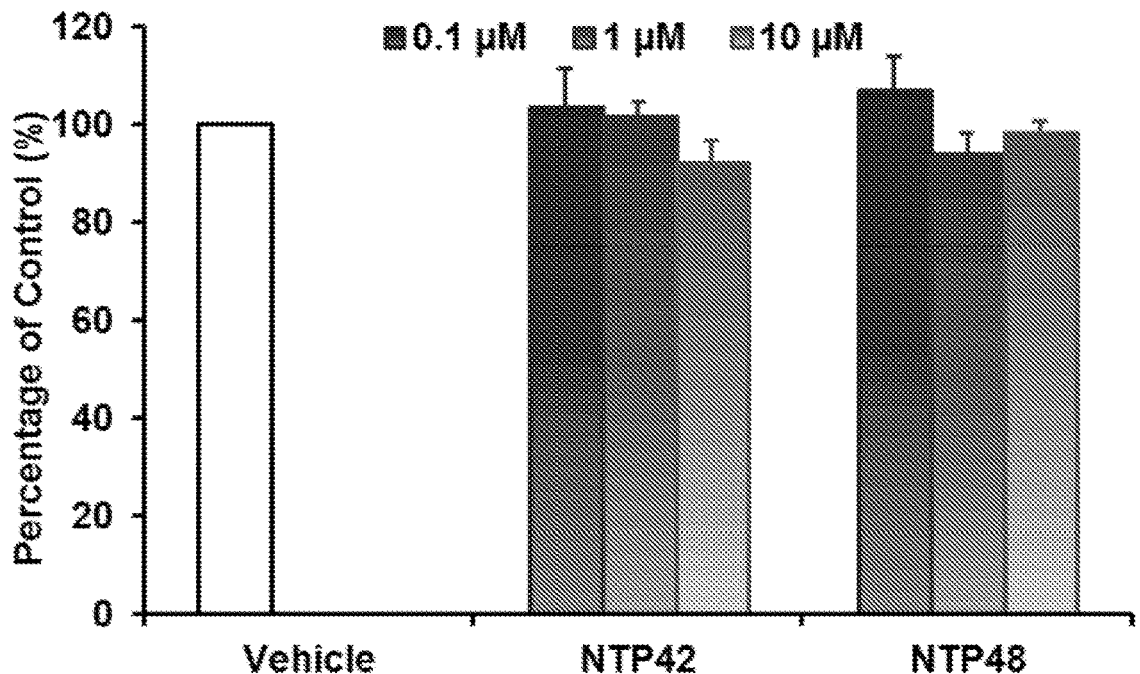
FIG. 13 shows that compounds of the invention exhibit no effect on the EP$_2$ receptor.

FIG. 13 shows that NTP42 and NTP48 exhibit no effect on the EP$_2$ receptor.

Figure 14:
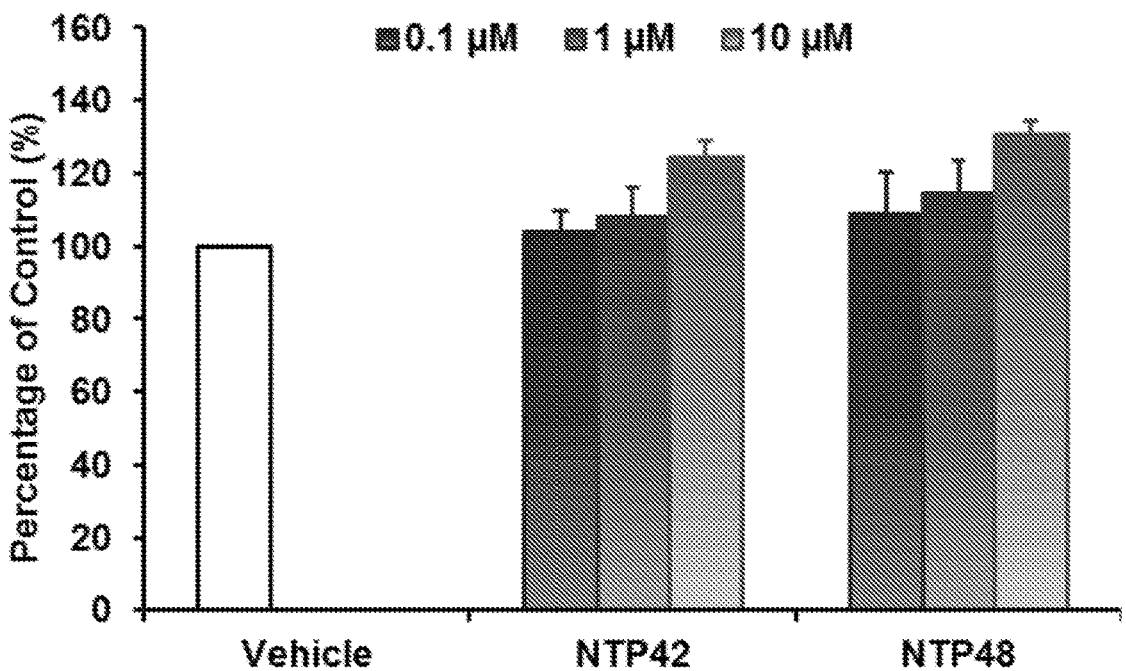
FIG. 14 shows that compounds of the invention exhibit no effect on the EP$_3$ receptor.

FIG. 14 shows that NTP42 and NTP48 exhibit no effect on the EP$_3$ receptor.

Figure 15:
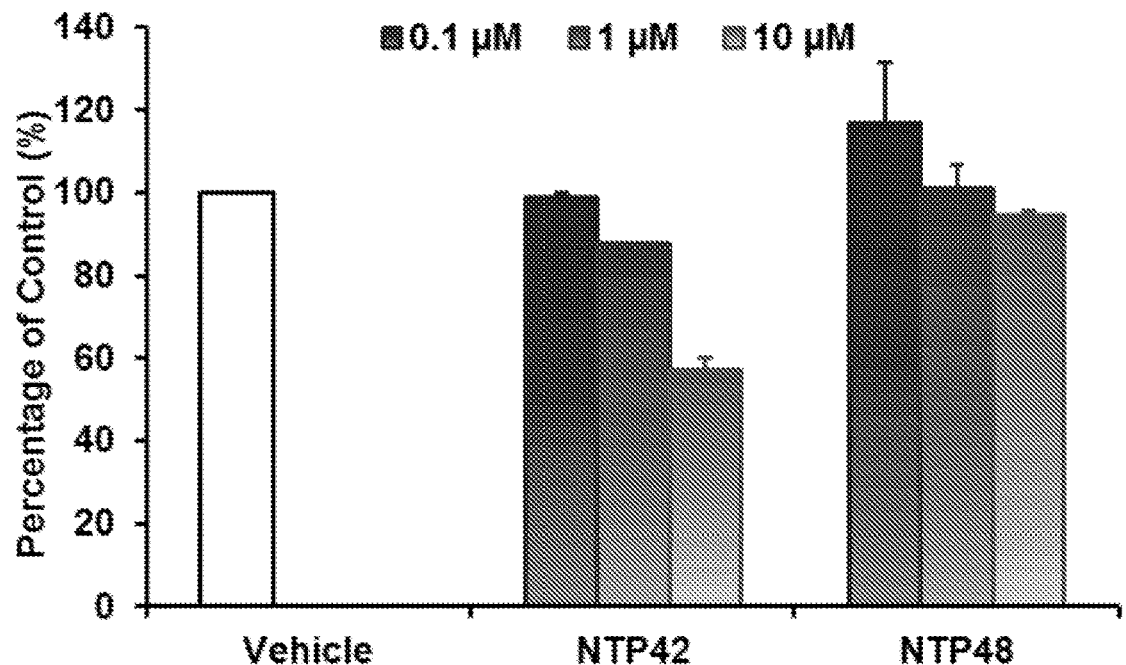
FIG. 15 shows that compounds of the invention exhibit no effect on the EP$_4$ receptor.

FIG. 15 shows that NTP42 and NTP48 exhibit no effect on the EP$_4$ receptor.

Figure 16:
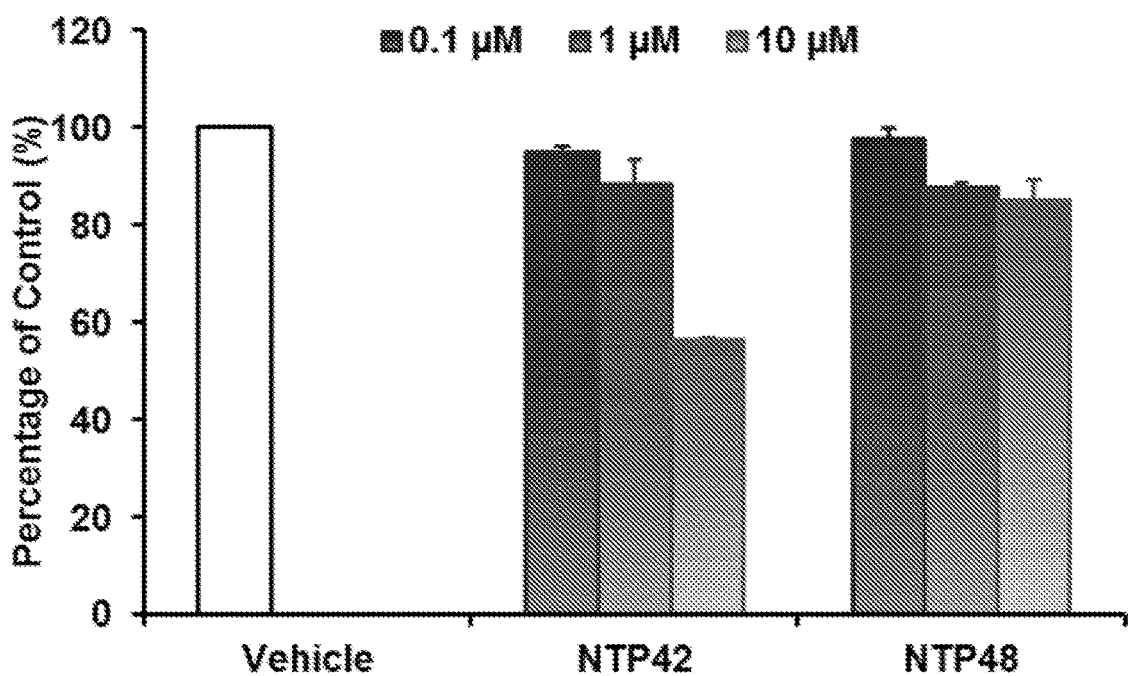
FIG. 16 shows that compounds of the invention exhibit no effect on the FP$_1$ receptor.

FIG. 16 shows that NTP42 and NTP48 exhibit no effect on the FP$_1$ receptor.

Figure 17:
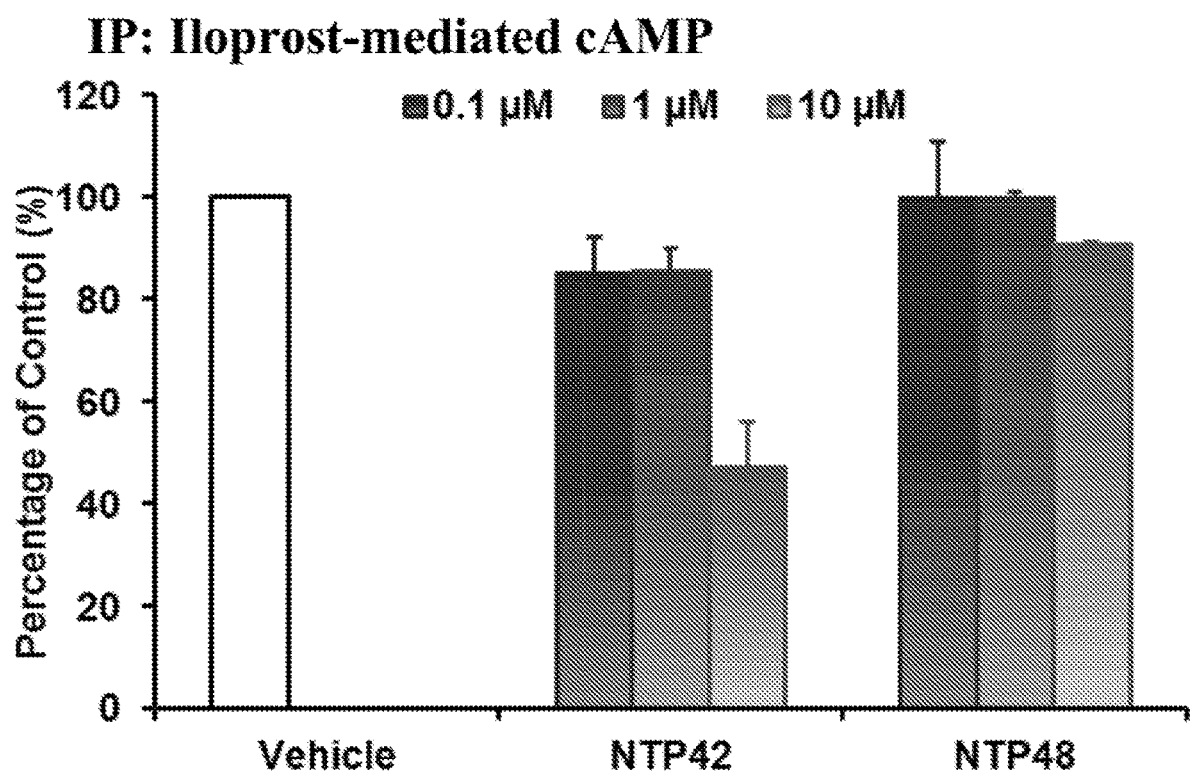
FIG. 17 shows that compounds of the invention exhibit no effect on the IP receptor.

FIG. 17 shows that NTP42 and NTP48 exhibit no effect on the IP receptor.

NTP42 and NTP48, have each been confirmed not to exhibit any effect on DP-, EP1-EP4-, FP- or IP-mediated signaling.

There is no or minimal inhibition of the majority of the non-TP-mediated signaling observed in the presence of either NTP42 & NTP48. Where there is inhibition of signaling, it is observed at the 10 µM concentration only. By way of example, NTP42, at 10 µM only exerts maximal inhibition of DP$_1$, EP$_1$, EP$_4$ & IP, where the percentage reduction in responses is <30%, ~55%, 40% & 50%, respectively. Compared to NTP42, NTP48 has less of an effect on the signaling of the non-TP prostanoid receptors and therefore, may be considered more favorable in this context.

Figure 18:
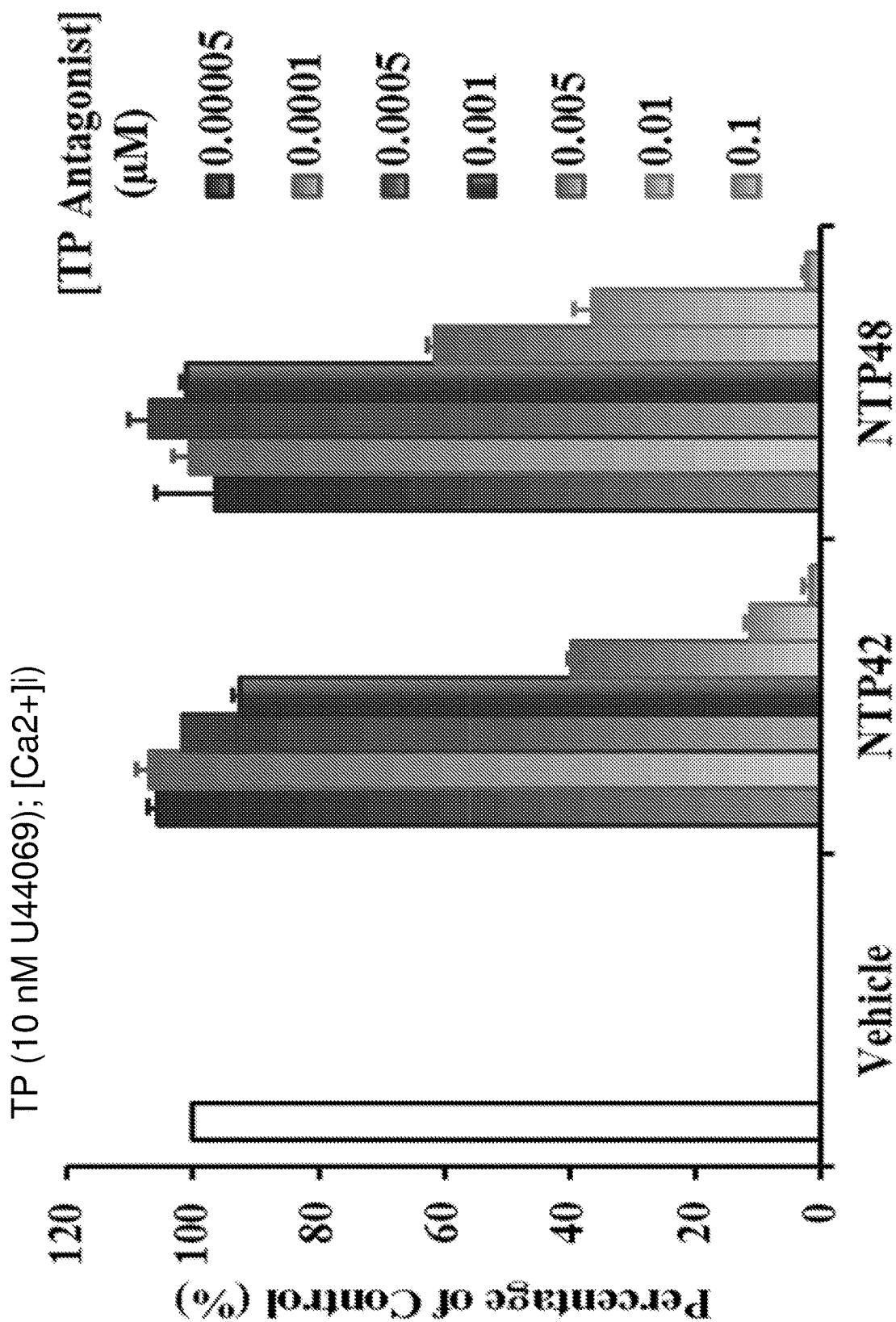
FIG. 18 presents the effect of compounds on TP- or U44069-mediated signaling.

FIG. 18 presents the effect of NTP42 and NTP48 on TP- or U44069-mediated signaling (CEREP use the related U44069 rather than U46619), including $IC_{50}$ values for inhibition (see also Table 4). Those effects indicate that NTP42 & NTP48 are potent antagonists of U46609 or TP. The differences in $IC_{50}$ values may be attributed to the differences in the particular conditions of the assay, including differences in cell type, agonist, calcium indicator, etc.

Table 4 is an example of the $IC_{50}$ values of NTP42 and NTP48 to antagonize TP-mediated $[Ca^{2+}]_i$ mobilization following stimulation of cells with the alternative TP agonist U46609.

TABLE 4

Comparison of $IC_{50}$ Values for Inhibition

| Compound | $IC_{50}$ Value for Inhibition of U44069-Mediated $[Ca^{2+}]_i$ Mobilization |
| --- | --- |
| NTP42 | 3.278 ± 0.34 nM |
| NTP48 | 7.712 ± 0.96 nM |

Example 4: Efficacy

FIGS. 19-23 show the efficacy of NTP42 in the monocrotoline (MCT)-induced model of pulmonary arterial hypertension (PAH) in rats. In brief, male Wistar/Kyoto rats were given a single dose of MCT (60 mg/kg, subcutaneously) and then treated with twice daily doses (oral dosing) for 28 days with either the drug vehicle, the test article NTP42 (0.25 mg/kg/dose, BID) or with the reference compounds Sildenafil (50 mg/kg/dose, BID) or TP20 (0.25 mg/kg/dose, BID). As a control, a group of rats were left untreated, i.e., no MCT or therapeutic drugs. At Day 28, post-MCT induction, rats were anaesthetised for cardiac surgery & hemodynamic parameters recorded. Thereafter, the trachea, heart & lungs were removed en masse, the wet weights of the heart & lungs recorded and then the lungs were harvested, fixed and processed for histopathology.

Figure 19:
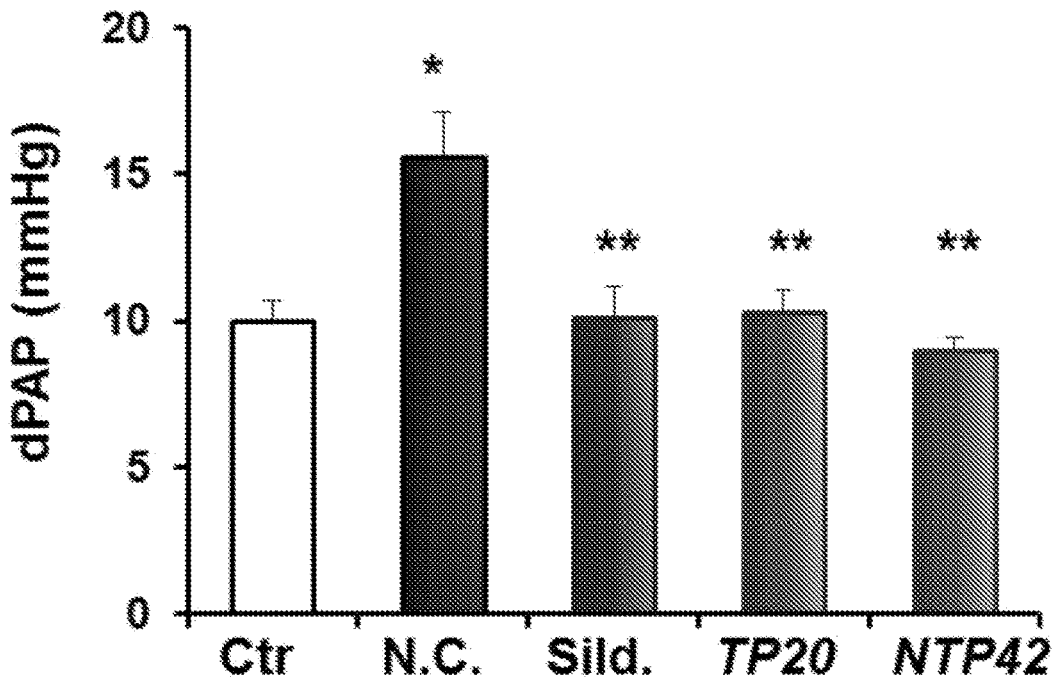
FIG. 19 shows the effect of compounds on diastolic pulmonary arterial pressure (dPAP).

FIG. 19 shows the effect of the test articles on diastolic pulmonary arterial pressure (dPAP).

Figure 20:
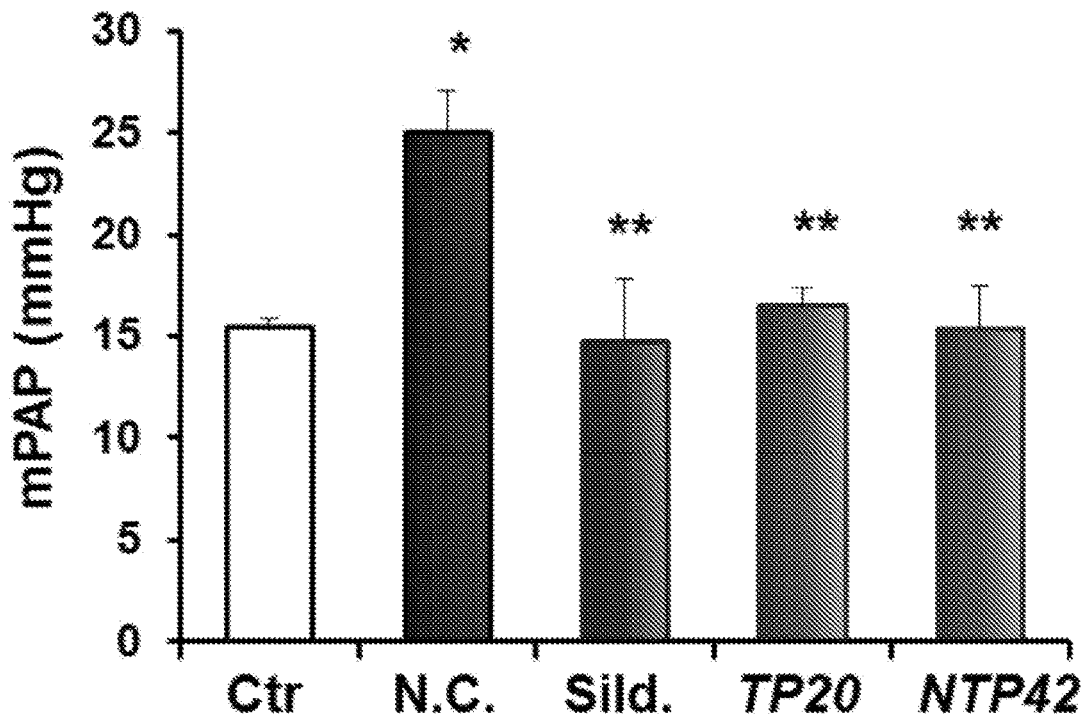
FIG. 20 shows the effect of compounds on mean pulmonary arterial pressure (mPAP).

FIG. 20 shows the effect of the test articles on mean pulmonary arterial pressure (mPAP).

Figure 21:
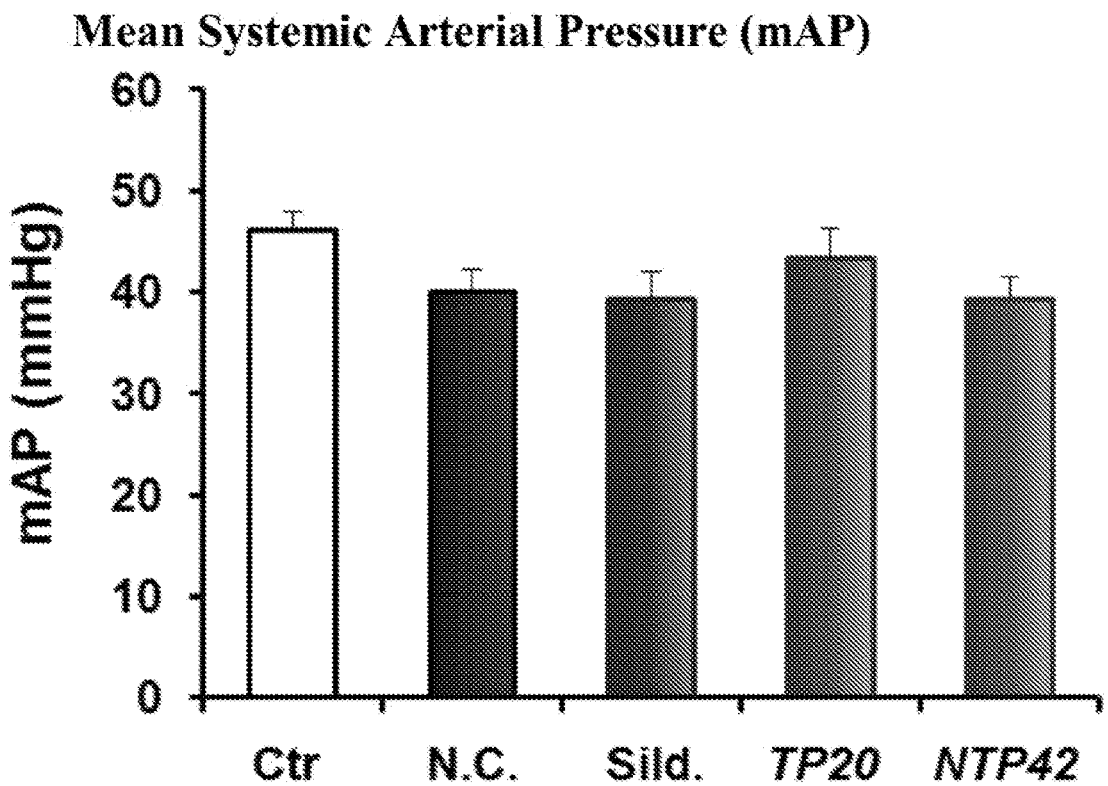
FIG. 21 shows the effect of compounds on mean systemic arterial pressure (mAP).

FIG. 21 shows the effect of the test articles on mean systemic arterial pressure (mAP).

Figure 22:
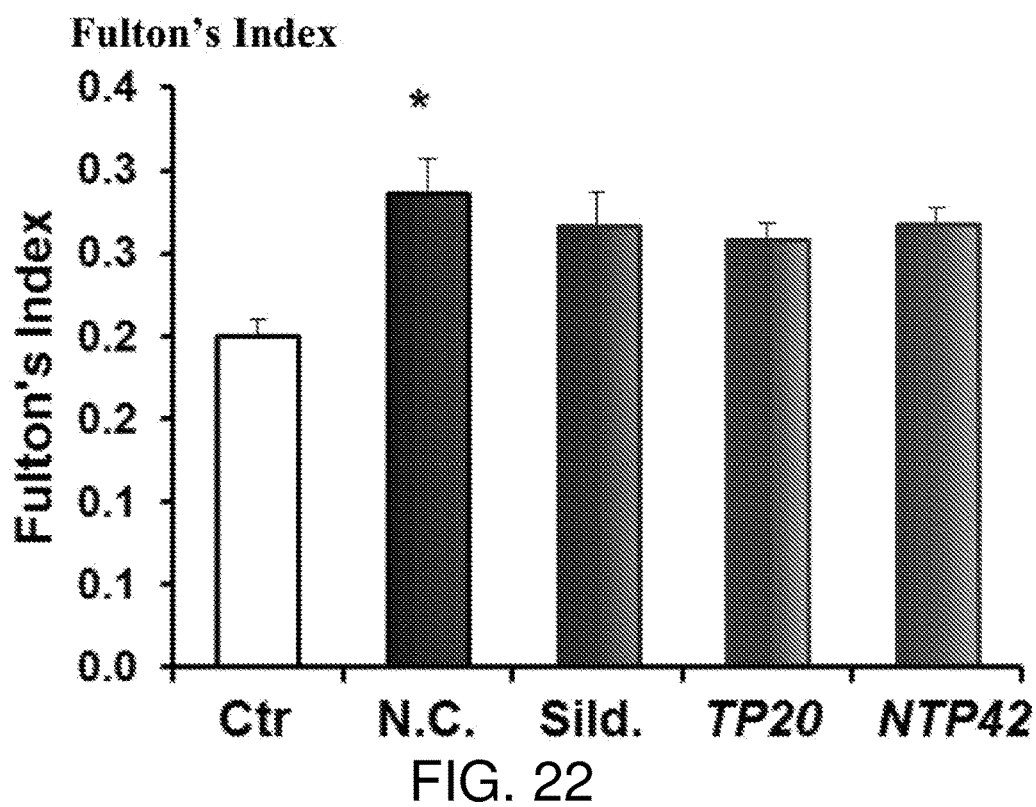
FIG. 22 shows the effect of compounds on Fulton's Index.

FIG. 22 shows the effect of the test articles on Fulton's Index.

For FIGS. 19-22, the control (Ctr) refers to animals not treated with MCT or test/reference compounds, while negative control (N.C.) refers to animals treated with MCT to induce PAH but not treated with test/reference compounds.

Figure 23:
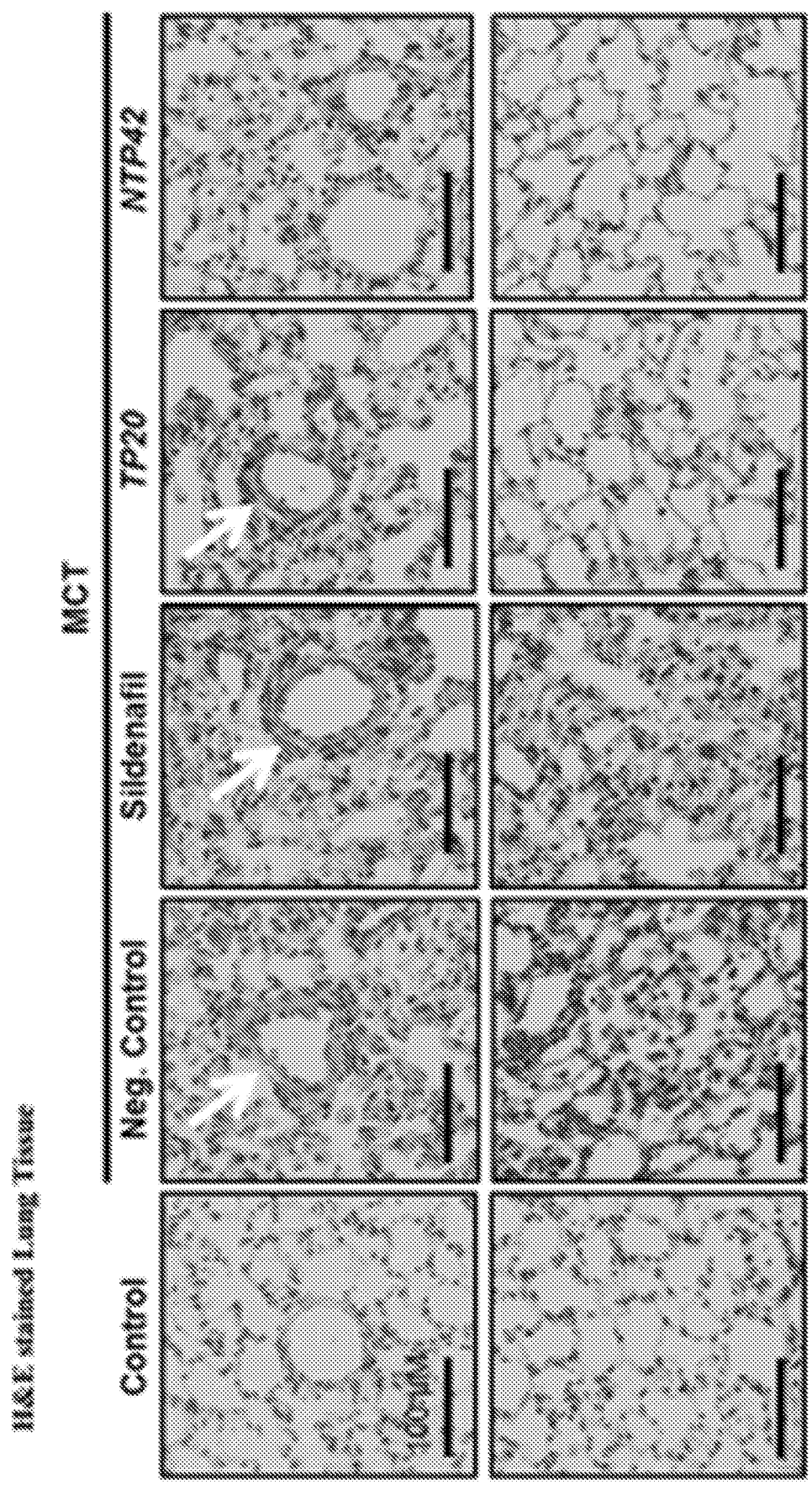
FIG. 23 shows lung tissue sections.

FIG. 23 shows formalin-fixed paraffin embedded (FFPE) lung tissue sections following staining with haematoxylin and eosin (H&E) and scanned using the Aperio image capture system. The representative images depict the extent of pulmonary vascular remodelling (upper panels, white arrows) and alveolar air-space (lower panels). The horizontal scale bar in each image corresponds to 100 μM and all images were captured at 20× magnification.

Aperio's ImageScope was used to analyze the digitally scanned H&E stained lung sections, where 10 random squares (approx. size or each square=1×10$^6$ μm$^2$) per lower, middle and upper section of lung tissue were selected for analysis. Within each square, all blood arterioles (complete arterioles within each square and those touching the right & bottom were assessed but not the left or top of the squares) were measured in ImageScope for luminal and total vessel diameter where the ratio of lumen to total vessel diameter was determined for each arteriole.

FIGS. 24-27 show the effect of the test articles on the mean (±S.E.M.) lumen: total vessel diameter ratio for all arterioles (Total) and the arterioles categorized by size: small, <50 μm total diameter; medium, 50-100 μm and large, >100 μm.

FIGS. 24-27 show morphometric Analysis of the effects of NTP42 on vascular remodeling in MCT-induced PAH.

Figure 24:
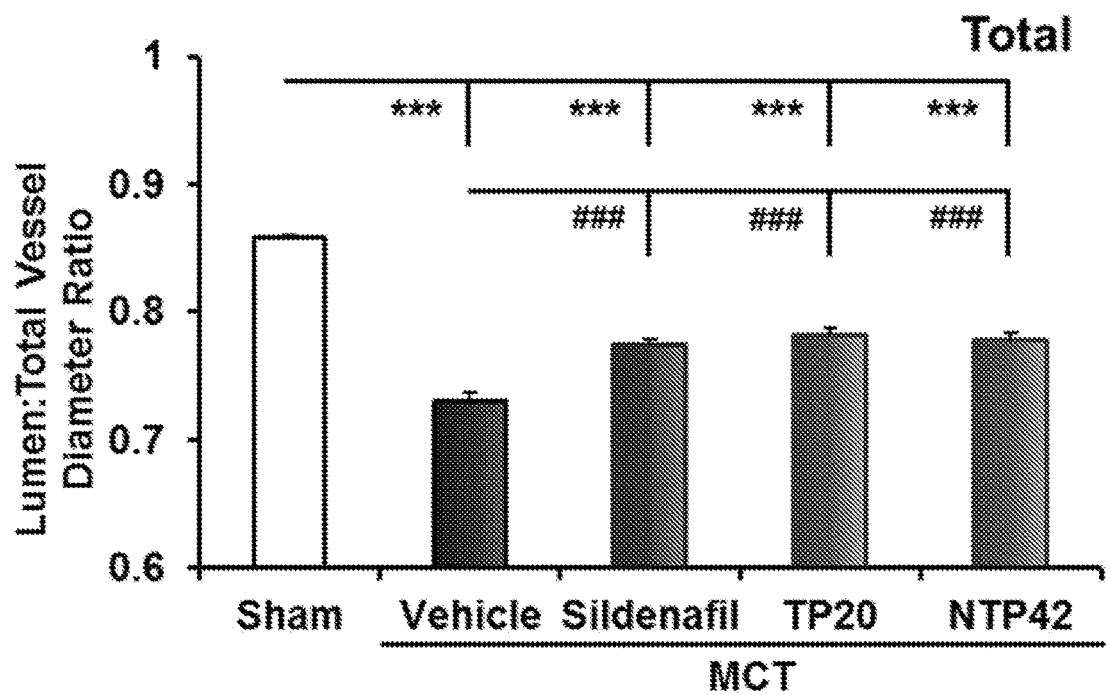
FIG. 24 show effects of compounds on the mean lumen: total vessel diameter ratio for total arterioles.

FIG. 24 presents data representing the mean (±SEM) lumen: total vessel diameter ratio for total arterioles.

Figure 25:
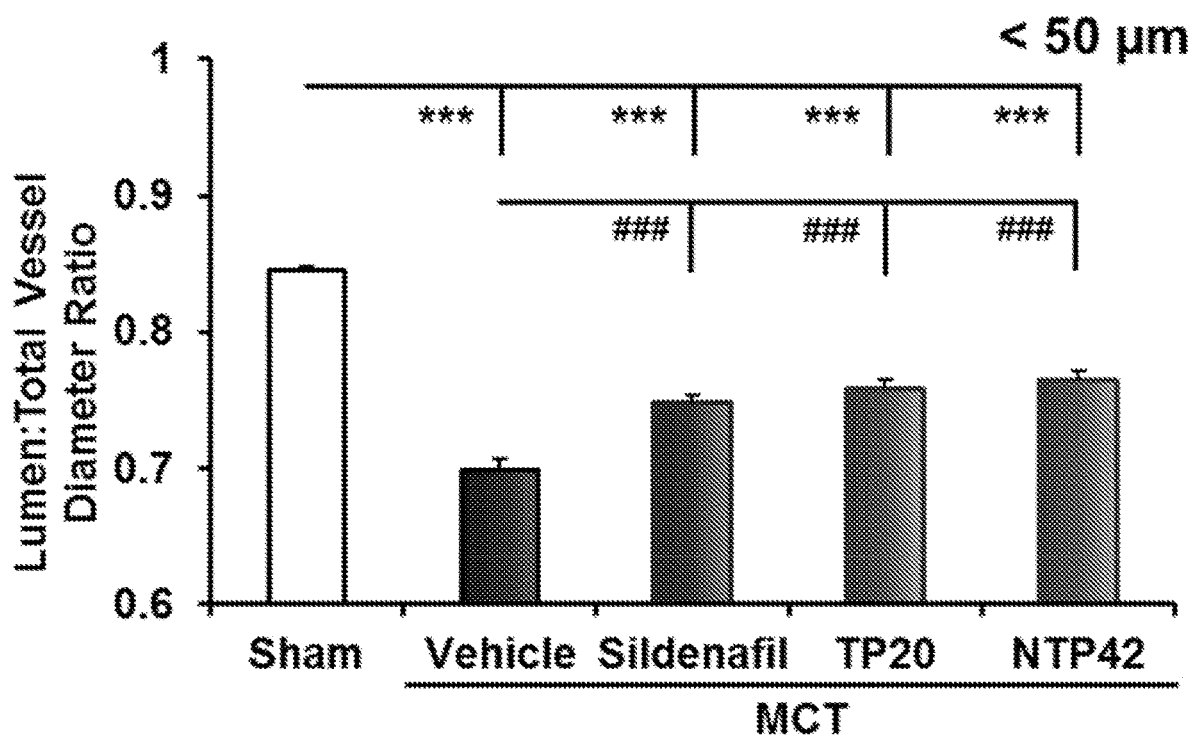
FIG. 25 show effects of compounds on the mean lumen: total vessel diameter ratio for small arterioles (<50 µm).

FIG. 25 presents data representing the mean (±SEM) lumen: total vessel diameter ratio for small arterioles (<50 μm).

Figure 26:
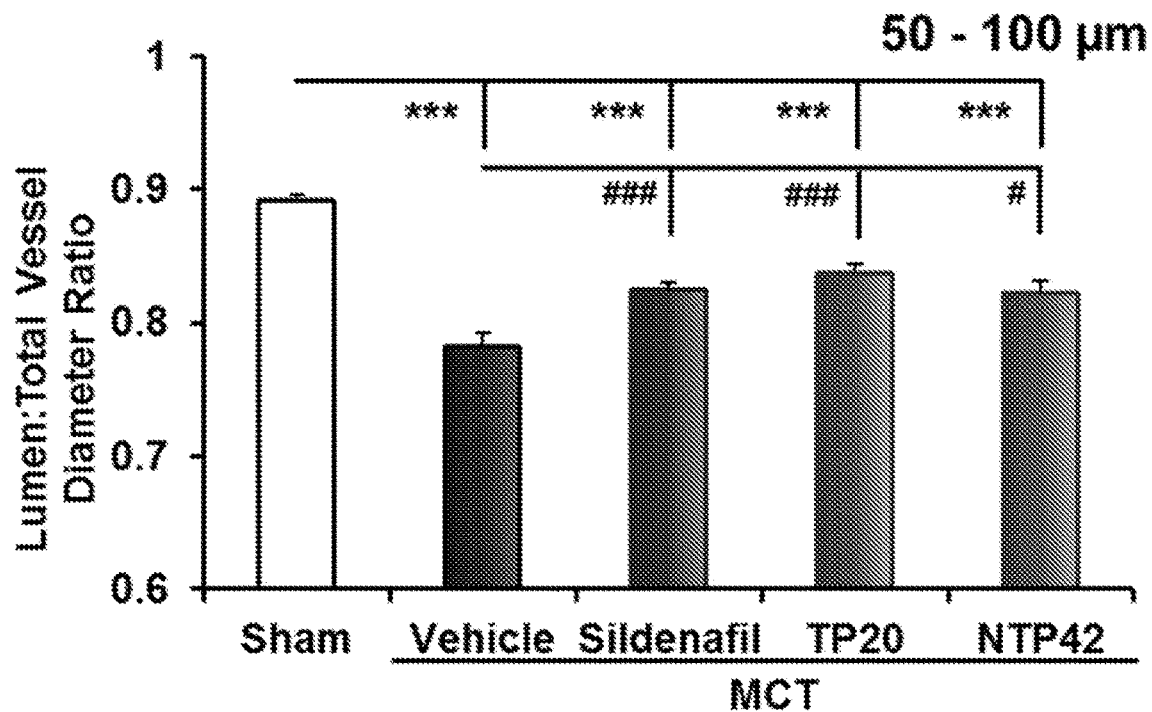
FIG. 26 show effects of compounds on the mean lumen: total vessel diameter ratio for medium arterioles (50-100 µm).

FIG. 26 presents data representing the mean (±SEM) lumen: total vessel diameter ratio for medium arterioles (50-100 μm).

Figure 27:
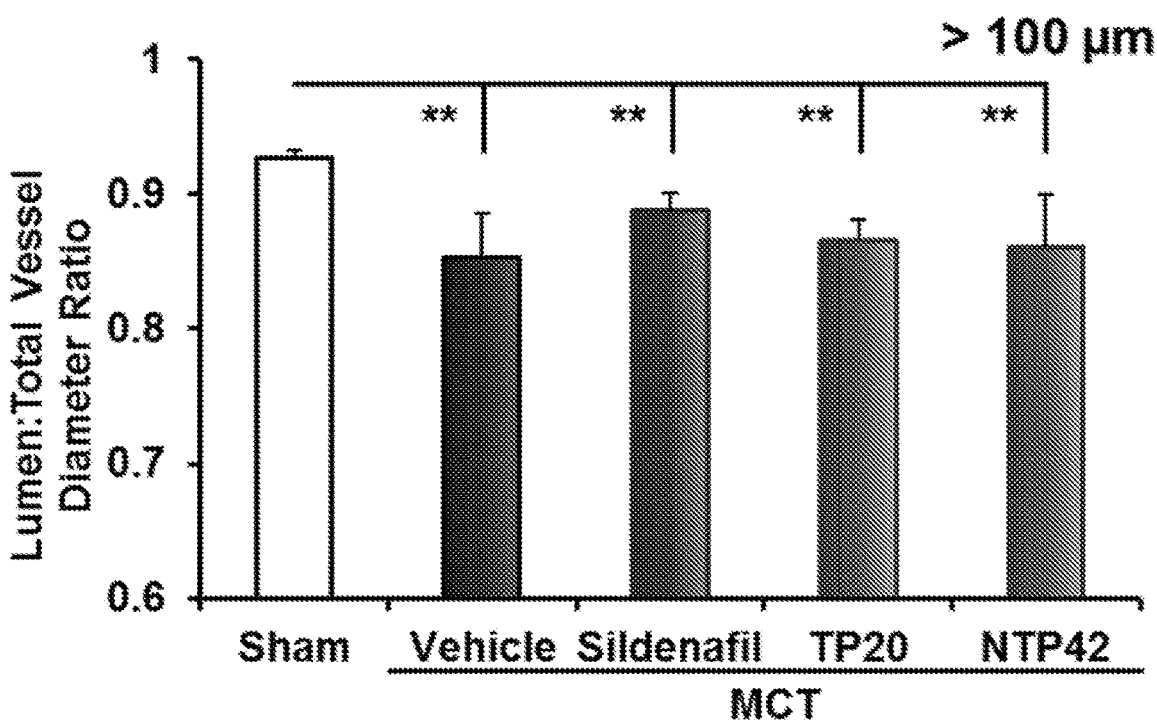
FIG. 27 show effects of compounds on the mean lumen: total vessel diameter ratio for large arterioles (>100 µm).

FIG. 27 presents data representing the mean (±SEM) lumen: total vessel diameter ratio for large arterioles (>100 μm). In FIGS. 24-27, asterisks indicate that the lumen: total vessel diameter ratio of the MCT-treated groups is statistically decreased from the Sham Control/no-MCT group and hash marks indicate that the lumen: total vessel diameter ratio of the Sildenafil, TP20 & NTP42-treated animals is significantly increased from animal-treated with MCT-alone, where */#, $p<0.05$; /##, $p<0.01$ and */###, $p<0.0001$.

Figure 28:
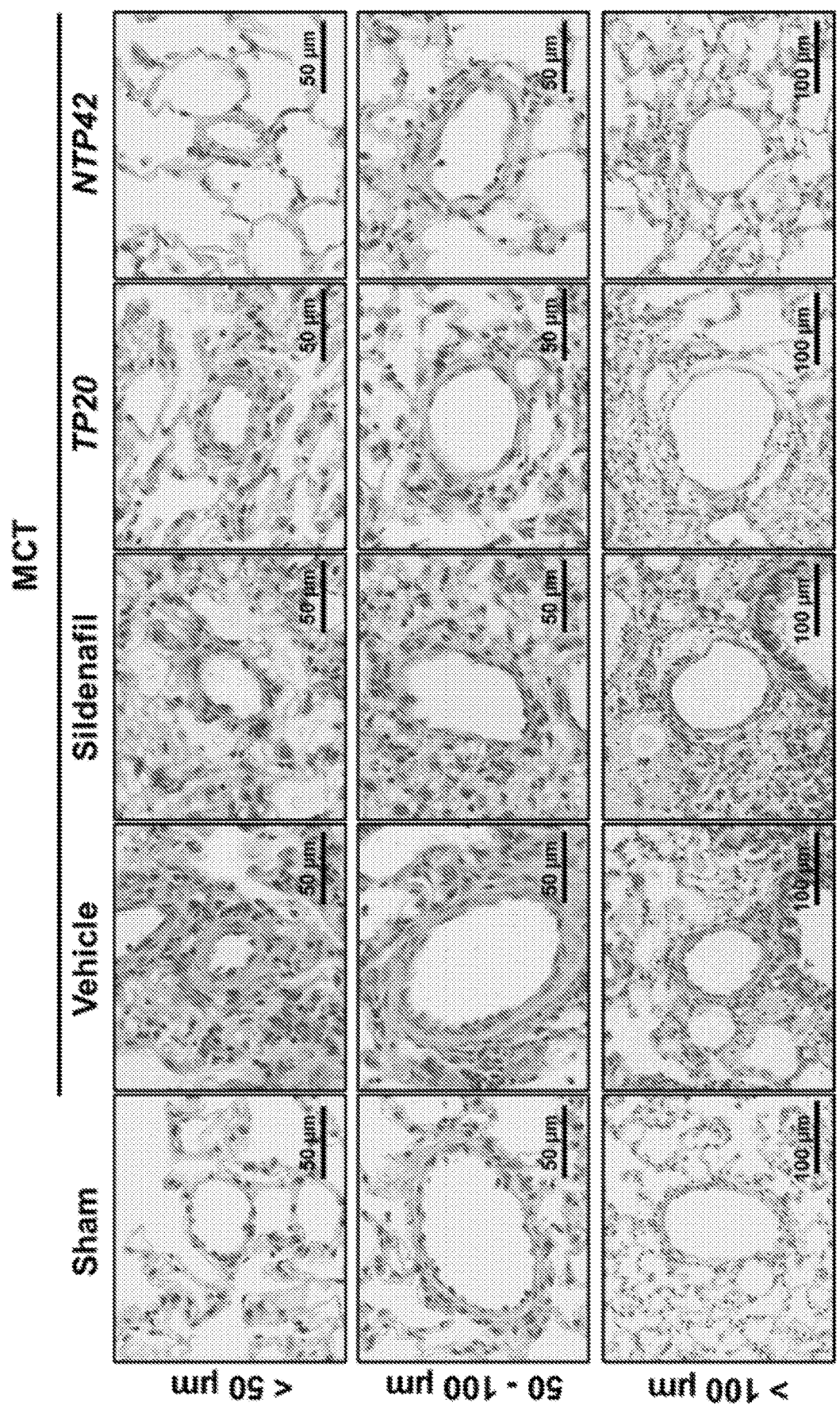
FIG. 28 shows FFPE lung tissue sections.

For FIG. 28, FFPE lung tissue sections were stained with H&E and digitally scanned (Aperio Slide Scanner). The representative images depict the extent of pulmonary vascular remodelling in small, medium and large arterioles. The horizontal scale bars correspond to 50 μm (small and medium arterioles) and 100 μm (large arterioles) were images were captured at 40× magnification. The representative images in FIG. 28 depict the extent of pulmonary vascular remodelling in small, medium and large vessels. The horizontal scale bar in each image corresponds to 50 μm (small and medium vessels) or 100 μm (large vessels) and all images were captured at 40× magnification.

FIG. 28 shows FFPE lung tissue sections following immunohistochemistry (IHC) using an anti-alpha smooth muscle actin antibody to detect smooth muscle cells in vessel walls, as an independent measure of assessing vessel remodeling or muscularization. The stained slides were scanned using the Aperio image capture system and the representative images in the upper panels depict the extent of pulmonary vascular remodelling in medium arterioles (50 to 100 μm diameter). The horizontal scale bar in each image corresponds to 50 μm and all images were captured at 20× magnification. The lower panels indicate intensity of positive (yellow to red) and negative (blue) staining as determined by ImageScope's Positive Pixel algorithm v 9.0.

In conclusion, the compounds of the invention, as exemplified by NTP42 in FIGS. 19-28, are efficacious in the MCT-induced PAH model as shown by measurement of the hemodynamic and histological features of the animals subject to MCT-PAH.

Example 5: Vascular Remodeling

Figure 29:
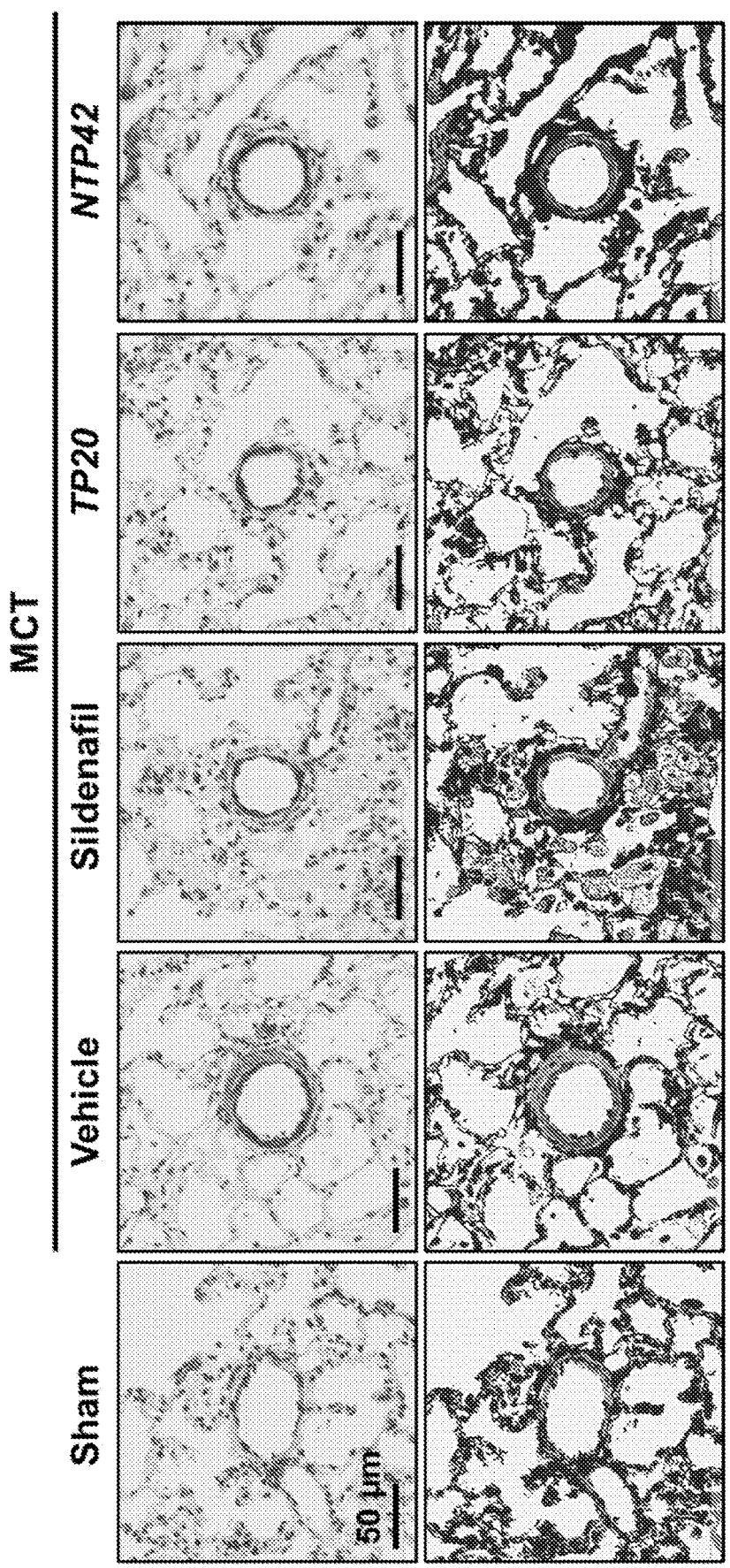
FIG. 29 shows effects of compounds on vascular remodeling.

FIG. 29 shows effects of NTP42 on vascular remodeling in MCT-induced PAH assessed by α-SMA IHC. FFPE lung tissue sections were immunostained with an anti-α smooth muscle actin (α-SMA; upper Figure, brown staining) antibody and nuclei counterstained with hematoxylin (upper Figure, blue nuclei) followed by digital scanning (Aperio Slide Scanner). The upper representative images depict α-SMA (brown) immunostaining of the smooth muscle layers around the arterioles and show the extent of pulmonary vascular remodeling in medium (50-100 μm diameter) arterioles. The lower Figures indicate negative (blue) or intensity of positive staining (yellow/red) as assessed using Aperio's ImageScope's Positive Pixel algorithm v 9.0. The horizontal scale bars correspond to 50 μm were images were captured at 20× magnification.

APPENDIX

Table 5 is a concordance of NTP references to formula numbers. Any entry in the left column is defined as the formula in the right column and vice-versa.

TABLE 5

Correspondence between NTP references an formula numbers

| NTP # | Formula # |
|---|---|
| NTP42 | (IV) |
| NTP43 | (V) |
| NTP44 | (VI) |
| NTP45 | (VII) |
| NTP46 | (VIII) |
| NTP47 | (IX) |
| NTP48 | (X) |
| NTP49 | (XI) |

What is claimed is:

1. A compound represented by formula (I):

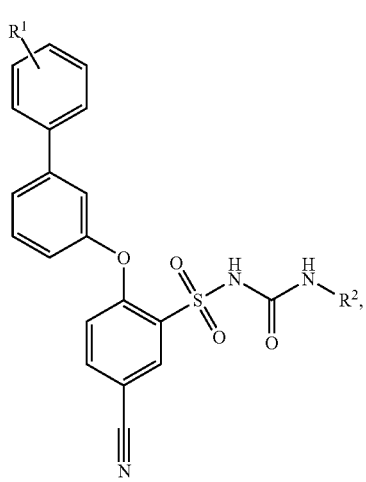

(I)

wherein:

$R^1$ is selected from the group consisting of a difluoromethoxy group, a trifluoromethoxy group, a difluoromethyl group, a primary amide group, a secondary amide group, a tertiary amide group, and a nitrile group; and $R^2$ is selected from the group consisting of an alkyl group of 6 or fewer carbons and a halogenated alkyl group of 6 or fewer carbons, wherein $R^2$ is not tert-butyl, or a pharmaceutically acceptable salt thereof.

2. The compound of claim 1, wherein $R^1$ is a difluoromethoxy group; and $R^2$ is selected from the group consisting of an alkyl group of 3 to 6 carbons and a halogenated alkyl group of 3 to 6 carbons.

3. The compound of claim 2, wherein the compound is represented by formula (II):

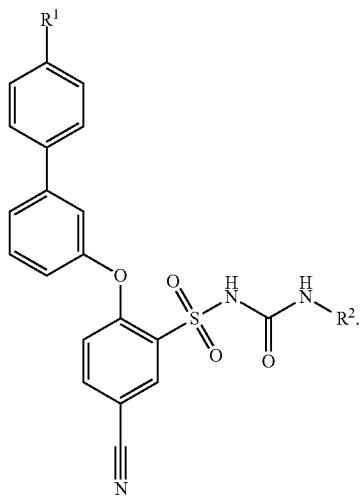

(II)

4. The compound of claim 3, wherein $R^2$ is selected from the group consisting of propyl, isopropyl, butyl, isobutyl, and sec-butyl.

5. The compound of claim 1, wherein $R^1$ is a trifluoromethoxy group; and $R^2$ is selected from the group consisting of an alkyl group of 3 to 6 carbons and a halogenated alkyl group of 3 to 6 carbons.

6. The compound of claim 5, wherein the compound is represented by formula (II):

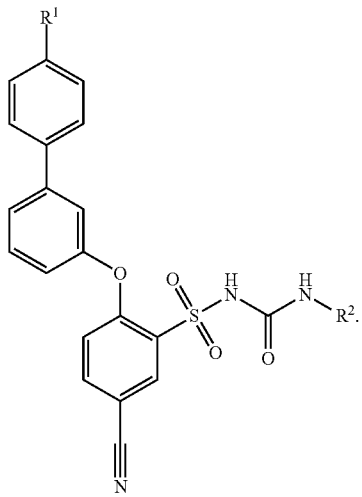

(II)

7. The compound of claim 6, wherein R² is selected from the group consisting of propyl, isopropyl, butyl, isobutyl, and sec-butyl.

8. The compound of claim 1, wherein R¹ is a difluoromethyl group; and

R² is selected from the group consisting of an alkyl group of 3 to 6 carbons and a halogenated alkyl group of 3 to 6 carbons.

9. The compound of claim 8, wherein the compound is represented by formula (II):

(II)

10. The compound of claim 9, wherein R² is selected from the group consisting of propyl, isopropyl, butyl, isobutyl, and sec-butyl.

11. The compound of claim 1, wherein R¹ is a primary amide group; and

R² is selected from the group consisting of an alkyl group of 3 to 6 carbons and a halogenated alkyl group of 3 to 6 carbons.

12. The compound of claim 11, wherein the compound is represented by formula (II):

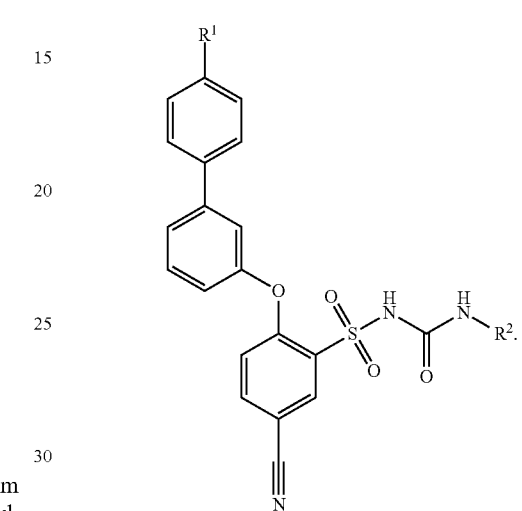

(II)

13. The compound of claim 12, wherein R² is selected from the group consisting of propyl, isopropyl, butyl, isobutyl, and sec-butyl.

14. The compound of claim 1, wherein R¹ is a secondary amide group; and

R² is selected from the group consisting of an alkyl group of 3 to 6 carbons and a halogenated alkyl group of 3 to 6 carbons.

15. The compound of claim 14, wherein the compound is represented by formula (II):

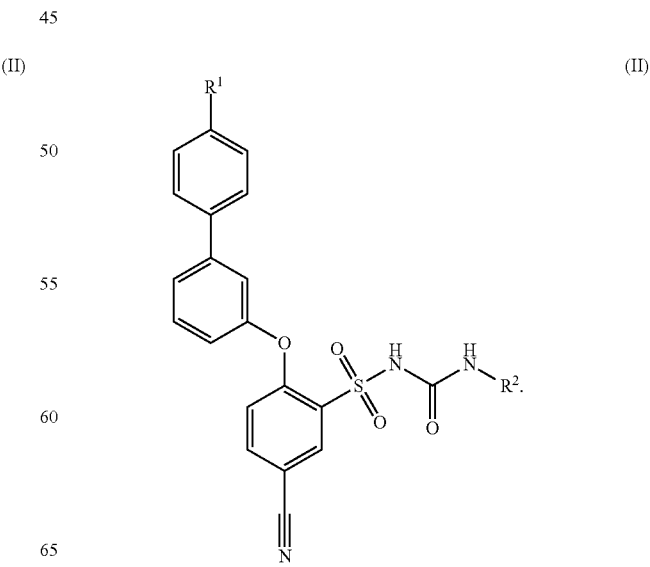

(II)

16. The compound of claim 15, wherein $R^2$ is selected from the group consisting of propyl, isopropyl, butyl, isobutyl, and sec-butyl.

17. The compound of claim 1, wherein $R^1$ is a tertiary amide group; and $R^2$ is selected from the group consisting of an alkyl group of 3 to 6 carbons and a halogenated alkyl group of 3 to 6 carbons.

18. The compound of claim 17, wherein the compound is represented by formula (II):

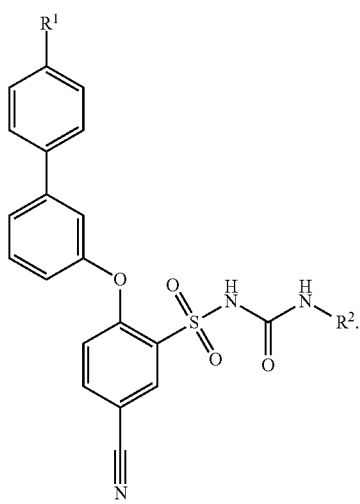

(II)

19. The compound of claim 18, wherein $R^2$ is selected from the group consisting of propyl, isopropyl, butyl, isobutyl, and sec-butyl.

20. The compound of claim 1, wherein $R^1$ is a nitrile group; and $R^2$ is selected from the group consisting of an alkyl group of 3 to 6 carbons and a halogenated alkyl group of 3 to 6 carbons.

21. The compound of claim 20, wherein the compound is represented by formula (II):

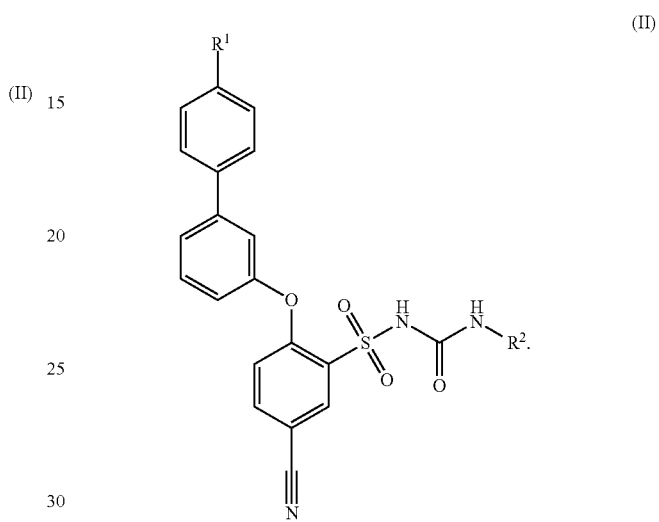

(II)

22. The compound of claim 21, wherein $R^2$ is selected from the group consisting of propyl, isopropyl, butyl, isobutyl, and sec-butyl.

* * * * *